United States Patent
Li et al.

(10) Patent No.: US 11,702,643 B2
(45) Date of Patent: Jul. 18, 2023

(54) SYSTEM AND METHOD FOR GENOME EDITING

(71) Applicant: INSTITUTE OF ZOOLOGY, CHINESE ACADEMY OF SCIENCES, Beijing (CN)

(72) Inventors: Wei Li, Beijing (CN); Qi Zhou, Beijing (CN); Fei Teng, Beijing (CN)

(73) Assignee: INSTITUTE OF ZOOLOGY, CHINESE ACADEMY OF SCIENCES, Beijing (CN)

( * ) Notice: Subject to any disclaimer, the term of this patent is extended or adjusted under 35 U.S.C. 154(b) by 746 days.

(21) Appl. No.: 16/603,975

(22) PCT Filed: Apr. 10, 2018

(86) PCT No.: PCT/CN2018/082446
§ 371 (c)(1),
(2) Date: Oct. 9, 2019

(87) PCT Pub. No.: WO2018/188571
PCT Pub. Date: Oct. 18, 2018

(65) Prior Publication Data
US 2020/0149021 A1 May 14, 2020

(30) Foreign Application Priority Data
Apr. 10, 2017 (CN) .................. 201710228595.X

(51) Int. Cl.
C12N 9/22 (2006.01)
C12N 15/113 (2010.01)
C12N 15/63 (2006.01)
C12N 15/90 (2006.01)
C12N 15/10 (2006.01)

(52) U.S. Cl.
CPC .............. *C12N 9/22* (2013.01); *C12N 15/113* (2013.01); *C12N 15/63* (2013.01); *C12N 15/90* (2013.01); C12N 2310/20 (2017.05); C12N 2800/80 (2013.01)

(58) Field of Classification Search
None
See application file for complete search history.

(56) References Cited

FOREIGN PATENT DOCUMENTS

| CN | 105907785 | 8/2016 |
|---|---|---|
| WO | 2016/186946 | 11/2016 |

OTHER PUBLICATIONS

Kleinstiver et al. "Genome-wide specificities of CRISPR-Cas Cpf1 nucleases in human cells." Nature biotechnology. Aug. 2016;34(8):869-74.
Dong et al. "The crystal structure of Cpf1 in complex with CRISPR RNA." Nature. Apr. 2016;532(7600):522-6.
Yamano et al. "Crystal structure of Cpf1 in complex with guide RNA and target DNA." Cell. May 5, 2016;165(4):949-62.
Supplementary European Search Report for Int'l Appl. No. EP 18783675 dated Mar. 27, 2020.
GenPept (full) "type V CRISPR-associated protein Cas12a/Cpf1 [Helcococcus kunzii]" NCBI Reference Sequence: WP_005398606.1. 2019. 1 sheet.
GenPept "type V CRISPR-associated protein Cas12a/Cpf1 [Bacteroidetes oral taxon 274]" NCBI Reference Sequence: WP_009217842.1. 2019. 1 sheet.
GenPept (full) "type V CRISPR-associated protein Cas12a/Cpf1 [Pseudobutyrivibrio ruminis]" NCBI Reference Sequence: WP_028248456.1. 2019. 2 sheets.
GenPept (full) "type V CRISPR-associated protein Cas12a/Cpf1 [Proteocatella sphenisci]" NCBI Reference Sequence: WP_028830240.1. 2019. 1 sheet.
GenPept (full) "type V CRISPR-associated protein Cas12a/Cpf1 [*Butyrivibrio* sp. NC3005]" NCBI Reference Sequence: WP_035798880.1. 2019. 1 sheet.
GenPept (full) "type V CRISPR-associated protein Cas12a/Cpf1 [*Oribacterium* sp. NK2B42]" NCBI Reference Sequence: WP_049895985.1. 2019. 1 sheet.
GenPept (full) "type V CRISPR-associated protein Cas12a/Cpf1 [Arcobacter butzleri]" NCBI Reference Sequence: WP_052943011.1. 2019. 1 sheet.
GenPept (full) "type V CRISPR-associated protein Cas12a/Cpf1 [[Eubacterium] rectale]" NCBI Reference Sequence: WP_055272206.1. 2019. 1 sheet.
GenPept (full) "hypothetical protein VC03_02970 [Sneathia amnii]" GenBank: AKC95493.1. 2015. 2 sheets.
Gao P, et al. "Type V CRISPR-Cas Cpf1 endonuclease employs a unique mechanism for crRNA-mediated target DNA recognition," Cell Res. Aug. 2016;26(8):901-13.
GenPept (full) "hypothetical protein US52_C0007G0008 [candidate division WS6 bacterium GW2011_GWA2_37_6]" GenBank: KKQ36153.1. 2015. 2 sheets.
GenPept (full) "CRISPR-associated protein Cpf1, subtype PREFRAN [Pseudobutyrivibrio xylanivorans]" GenBank: SCZ76797.1. 2016. 1 sheet.

*Primary Examiner* — Suzanne M Noakes
*Assistant Examiner* — Jae W Lee
(74) *Attorney, Agent, or Firm* — Robin L. Teskin; Baker, Donelson, Bearman, Caldwell & Berkowitz PC

(57) ABSTRACT

The invention relates to the field of genetic engineering. In particular, the present invention relates to a novel eukaryotic genome editing system and method. More specifically, the present invention relates to a CRISPR-Cpf1 system capable of efficiently editing a genome of a eukaryotic cell and the use thereof.

19 Claims, 16 Drawing Sheets
Specification includes a Sequence Listing.

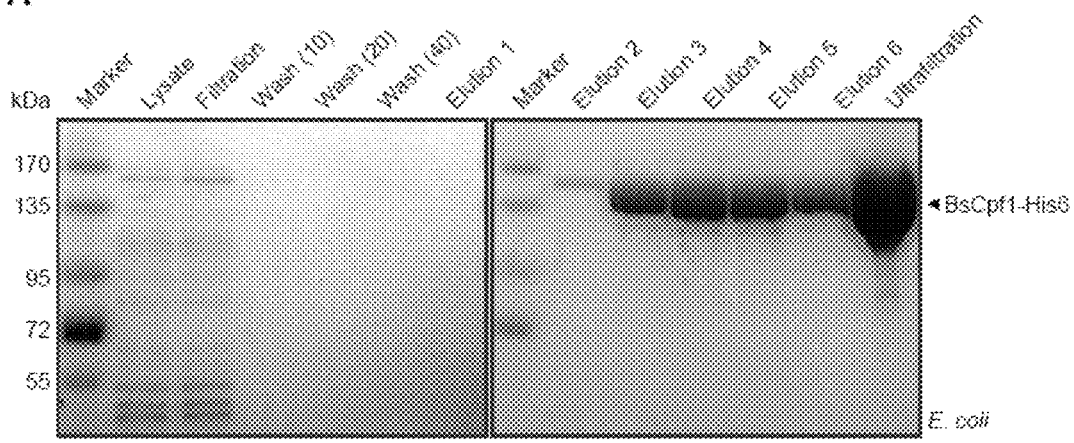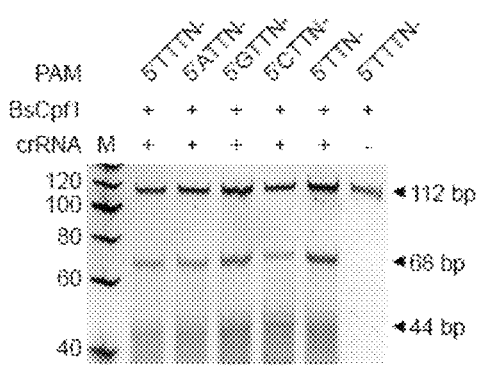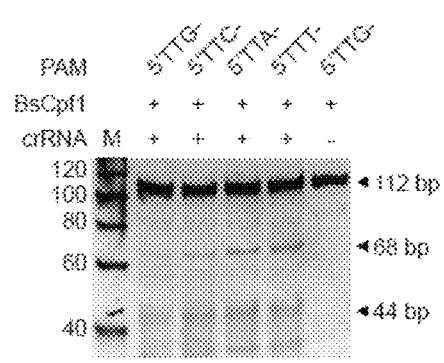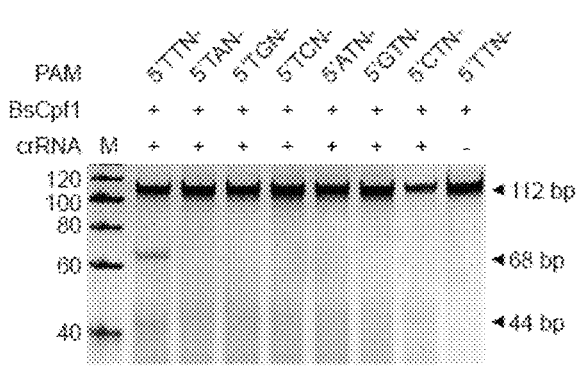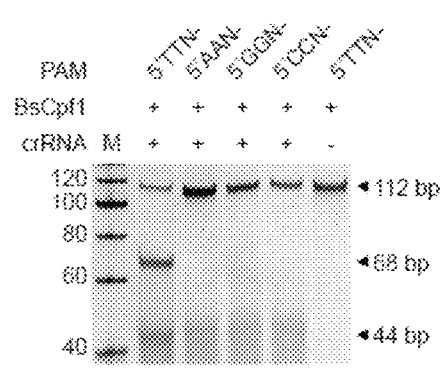
Figure 6

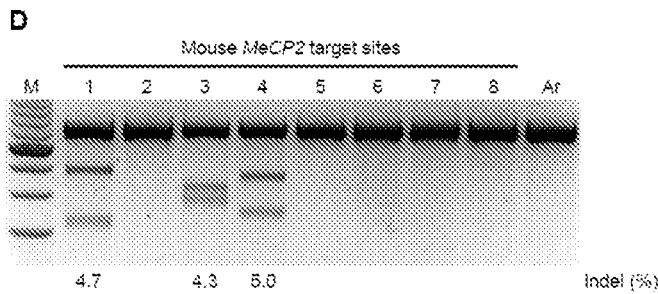

E

Mouse *MeCP2* target site 1

| SEQ ID NO:198 | GAGCCACTACAACCTTCAGCCCACCATTCTGCAGAGCCAGCAGAGGCAGGCAAAGCAGAAACATCAGAAAGCTCAGG |
| SEQ ID NO:199 | GAGCTACTACAACCTTCAGCCTAC············································CAGAGGCAGGCAAAGCAGAAACATCAGAAAGCTCAGG |
| SEQ ID NO:200 | GAGCTACTACAACCTTCAGCCCA············································GCAGAGGCAGGCAAAGCAGAAACATCAGAAAGCTCAGG |
| SEQ ID NO:201 | GAGCTA············································aAGAGCCAGCAGAGGCAGGCAAAGCAGAAACATCAGAAAGCTCAGG |

Mouse *MeCP2* target site 3

| SEQ ID NO:202 | GCAGGCAAAGCAGAAACATCAGAAAGCTCAGGCTCTGCCCCAGCAGTGCCAGAAGCCTCGGCTTCCCCAAACAGCG |
| SEQ ID NO:203 | GCAGGCAAAGCAGAAACATCAGAAAGCTCAGGCTtt·····tugacascatagugAGCCTCGGCTTCCCCAAACAGCG |
| SEQ ID NO:204 | GCAGGGCAAAGCAGAAACATCAGAAAGCTCAGGCTCTGCCCAGCAGTC·····AAGCCTCGGCTTCCCCAAACAGGG |
| SEQ ID NO:205 | GCAGGGCAAAGCAGAAACATCAGAAAGCTCAGGCTCTGCCCAGCAG·········AAGCCTCGGCTTCCCCAAACAGGG |
| SEQ ID NO:206 | GCAGGGCAAAGCAGAAACATCAGAAAGCTCAGGCTCTGCCCAGC·············GAAGCCTCGGCTTCCCCAAACAGGG |
| SEQ ID NO:207 | GCAGGGCAAAGCAGAAACATCAGAAAGCTCAGGCTCTGCCC·····AGCCTCGGCTTCCCCAAACAGGG |
| SEQ ID NO:208 | GCAGGCAAAGCAGAAACATCAGAAAGCTCAGGCTC·················AGAAGCCTCGGCTTCCCCAAACAGCG |

Mouse *MeCP2* target site 4

| SEQ ID NO:209 | ATCCGTGACCGGGGACCTATGTATGATGACCCTGCCTTGCTGAAGGTTGGACACGAAAGCTTAAACAAAGGAAGTC |
| SEQ ID NO:210 | ATCCGTGACCGGGGACCTATGTATGATGACC················ACGAAAGCTTAAACAAAGGAAGTC |

F

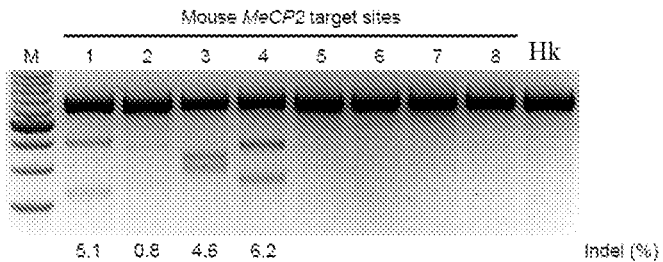

G

Mouse *MeCP2* target site 1

| SEQ ID NO:211 | GAGCCACTACAACCTTCAGCCCACCATTCTGCAGAGCCAGCAGCCAGGCAAAGCAGAAACATCAGAAAGCTCAGG |
| SEQ ID NO:212 | GAGCCACTACAACCTTCAGCCCA······TCTGCAGAGCCAGCAGCCAGGCAAAGCAGAAACATCAGAAAGCTCAGG |
| SEQ ID NO:213 | GAGCCACTACAACCTT···················CAGCAGAGGCAGGCAAAGCAGAAACATCAGAAAGCTCAGG |

Mouse *MeCP2* target site 2

| SEQ ID NO:214 | TGAGCCACTACAACCTTCAGCCCATCATTCTGCAGAGCCAGCAGAGGCAGGCAAAGCAGAAACATCAGAAAGCTTAG |
| SEQ ID NO:215 | TGAGCCACTACAACCTTCAGCCCATCATTCTGCAGAGCCAGCAGA··········AACATCAGAAAGCTTAG |

Mouse *MeCP2* target site 3

| SEQ ID NO:216 | CATCAGAAAGCTCAGGCTCTGCCCTAGCA---------------GTGCCAGAAGCCTGGCTTCCCCTAAACAGCG |
| SEQ ID NO:217 | CATCAGAAAGCTCAGGCTCTGCCCTAcgacacacacattgtacacattgcaCTGCCTGGCTTCCCCTAAACAGCG |
| SEQ ID NO:218 | CATCAGAAAGCTCAGGCTCTGCCCTAGCA---------------CAGAAGCCTGGCTTCCCCTAAACAGCG |

Mouse *MeCP2* target site 4

| SEQ ID NO:219 | ATCCGTGACCGGGGACCTATGTATGATGACCCACCTTGCCTGAAGGTTGGACACGAAAGCTTAAACAAAGGAAGTC |
| SEQ ID NO:220 | ATCCGTGACCGGGGACCTATGTATGATGACCC·······TGCCTGAAGGTTGGACACGAAAGCTTAAACAAAGGAAGTC |
| SEQ ID NO:221 | ATCCGTGACCGGGGACCTATGTATG··············GGTTGGACACGAAAGCTTAAACAAAGGAAGTC |
| SEQ ID NO:222 | ATCCGTGACCGGG················GCCTGAAGGTTGGACACGAAAGCTTAAACAAAGGAAGTC |

Figure 10

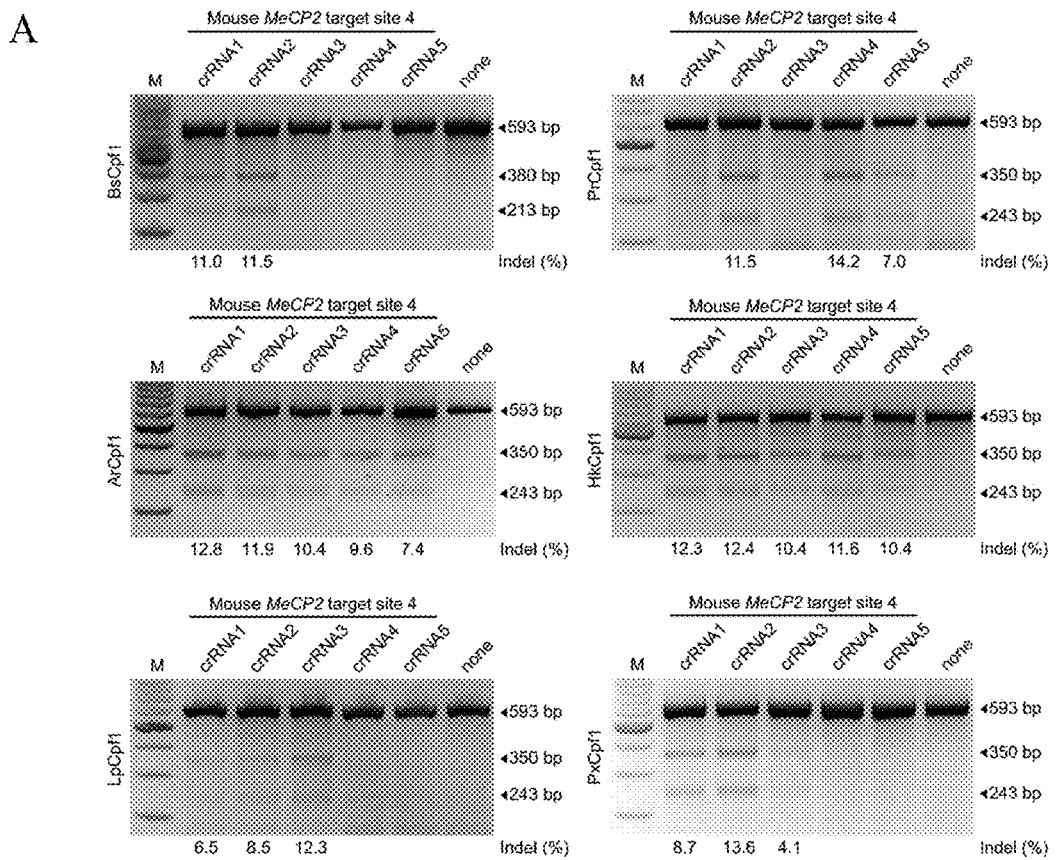
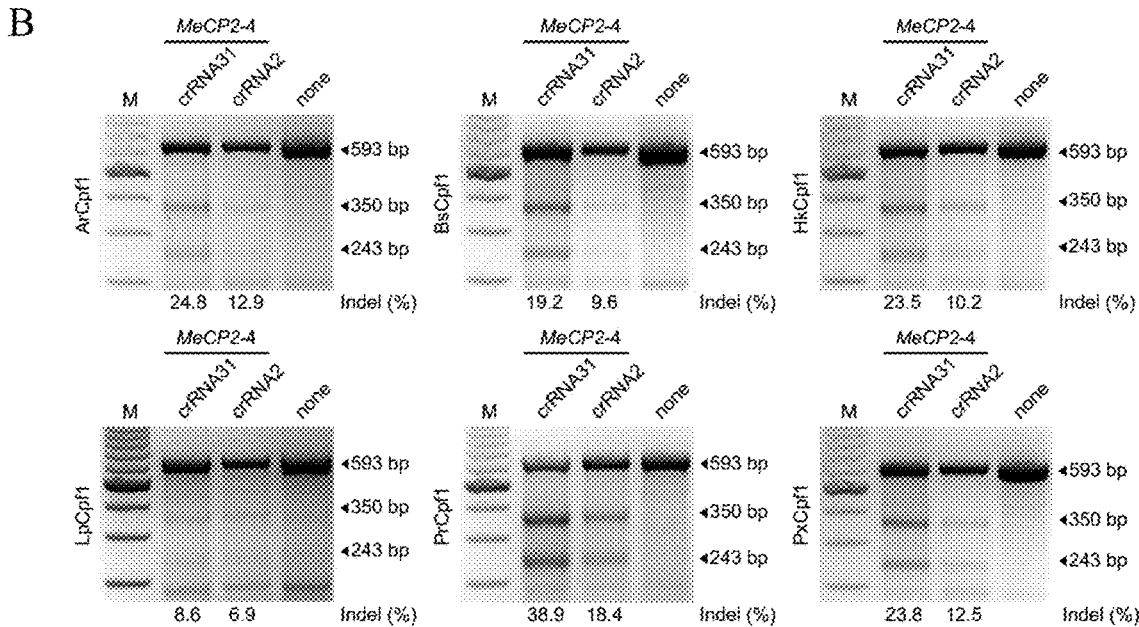
Figure 13

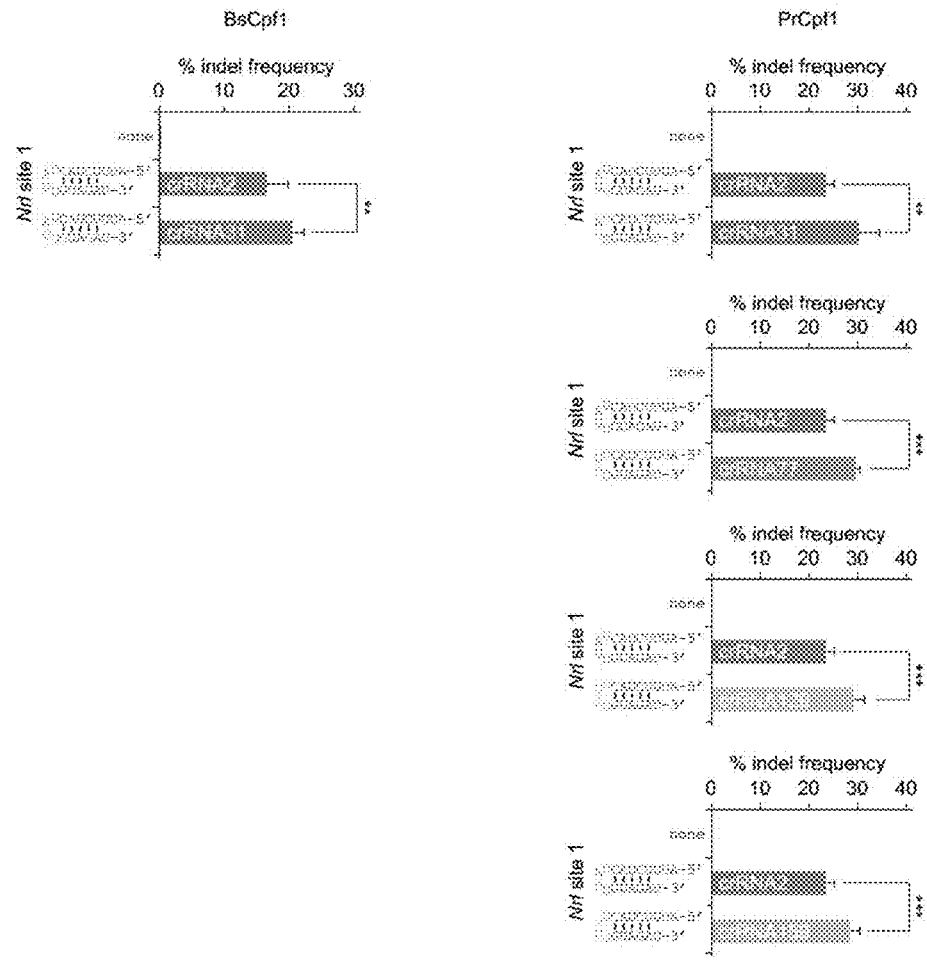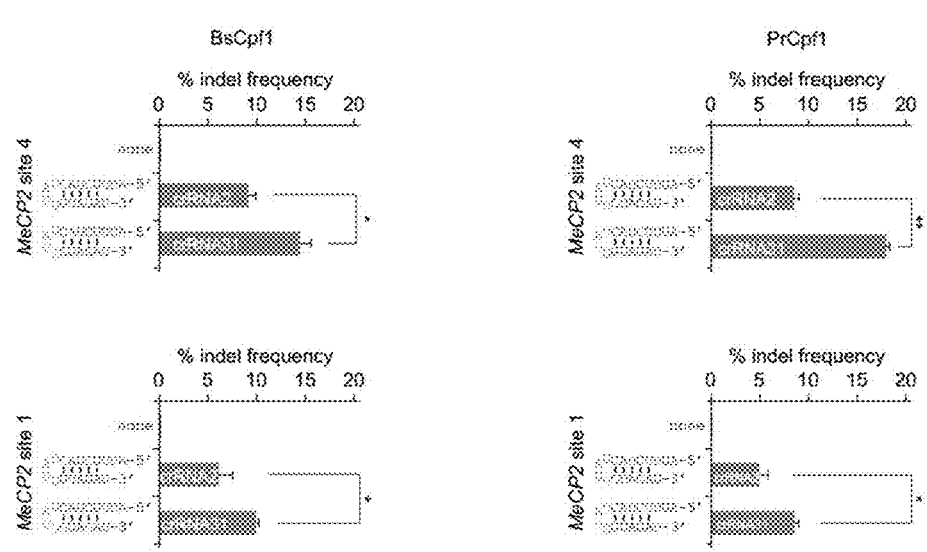
Figure 14

SEQUENCE LISTING

<160> NUMBER OF SEQ ID NOS: 258

<210> SEQ ID NO 1
<211> LENGTH: 1263
<212> TYPE: PRT
<213> ORGANISM: Agathobacter rectalis

<400> SEQUENCE: 1

Met Asn Asn Gly Thr Asn Asn Phe Gln Asn Phe Ile Gly Ile Ser Ser
1               5                   10                  15

Leu Gln Lys Thr Leu Arg Asn Ala Leu Thr Pro Thr Glu Thr Thr Gln
            20                  25                  30

Gln Phe Ile Val Lys Asn Gly Ile Ile Lys Glu Asp Glu Leu Arg Gly
        35                  40                  45

Glu Asn Arg Gln Ile Leu Lys Asp Ile Met Asp Asp Tyr Tyr Arg Gly
    50                  55                  60

Phe Ile Ser Glu Thr Leu Ser Ser Ile Asp Asp Ile Asp Trp Thr Ser
65                  70                  75                  80

Leu Phe Glu Lys Met Glu Ile Gln Leu Lys Asn Gly Asp Asn Lys Asp
                85                  90                  95

Thr Leu Ile Lys Glu Gln Ala Glu Lys Arg Lys Ala Ile Tyr Lys Lys
            100                 105                 110

Phe Ala Asp Asp Asp Arg Phe Lys Asn Met Phe Ser Ala Lys Leu Ile

-continued

```
            115                 120                 125
Ser Asp Ile Leu Pro Glu Phe Val Ile His Asn Asn Tyr Ser Ala
130                 135                 140

Ser Glu Lys Glu Glu Lys Thr Gln Val Ile Lys Leu Phe Ser Arg Phe
145                 150                 155                 160

Ala Thr Ser Phe Lys Asp Tyr Phe Lys Asn Arg Ala Asn Cys Phe Ser
                165                 170                 175

Ala Asp Asp Ile Ser Ser Ser Cys His Arg Ile Val Asn Asp Asn
            180                 185                 190

Ala Glu Ile Phe Phe Ser Asn Ala Leu Val Tyr Arg Arg Ile Val Lys
            195                 200                 205

Asn Leu Ser Asn Asp Asp Ile Asn Lys Ile Ser Gly Asp Met Lys Asp
210                 215                 220

Ser Leu Lys Lys Met Ser Leu Glu Lys Ile Tyr Ser Tyr Glu Lys Tyr
225                 230                 235                 240

Gly Glu Phe Ile Thr Gln Glu Gly Ile Ser Phe Tyr Asn Asp Ile Cys
                245                 250                 255

Gly Lys Val Asn Ser Phe Met Asn Leu Tyr Cys Gln Lys Asn Lys Glu
                260                 265                 270

Asn Lys Asn Leu Tyr Lys Leu Arg Lys Leu His Lys Gln Ile Leu Cys
            275                 280                 285

Ile Ala Asp Thr Ser Tyr Glu Val Pro Tyr Lys Phe Glu Ser Asp Glu
290                 295                 300

Glu Val Tyr Gln Ser Val Asn Gly Phe Leu Asp Asn Ile Ser Ser Lys
305                 310                 315                 320

His Ile Val Glu Arg Leu Arg Lys Ile Gly Asp Asn Tyr Asn Gly Tyr
                325                 330                 335

Asn Leu Asp Lys Ile Tyr Ile Val Ser Lys Phe Tyr Glu Ser Val Ser
            340                 345                 350

Gln Lys Thr Tyr Arg Asp Trp Glu Thr Ile Asn Thr Ala Leu Glu Ile
            355                 360                 365

His Tyr Asn Asn Ile Leu Pro Gly Asn Gly Lys Ser Lys Ala Asp Lys
            370                 375                 380

Val Lys Lys Ala Val Lys Asn Asp Leu Gln Lys Ser Ile Thr Glu Ile
385                 390                 395                 400

Asn Glu Leu Val Ser Asn Tyr Lys Leu Cys Pro Asp Asp Asn Ile Lys
                405                 410                 415

Ala Glu Thr Tyr Ile His Glu Ile Ser His Ile Leu Asn Asn Phe Glu
                420                 425                 430

Ala Gln Glu Leu Lys Tyr Asn Pro Glu Ile His Leu Val Glu Ser Glu
            435                 440                 445

Leu Lys Ala Ser Glu Leu Lys Asn Val Leu Asp Val Ile Met Asn Ala
            450                 455                 460

Phe His Trp Cys Ser Val Phe Met Thr Glu Glu Leu Val Asp Lys Asp
465                 470                 475                 480

Asn Asn Phe Tyr Ala Glu Leu Glu Glu Ile Tyr Asp Glu Ile Tyr Pro
                485                 490                 495

Val Ile Ser Leu Tyr Asn Leu Val Arg Asn Tyr Val Thr Gln Lys Pro
                500                 505                 510

Tyr Ser Thr Lys Lys Ile Lys Leu Asn Phe Gly Ile Pro Thr Leu Ala
            515                 520                 525

Asp Gly Trp Ser Lys Ser Lys Glu Tyr Ser Asn Asn Ala Ile Ile Leu
530                 535                 540
```

```
Met Arg Asp Asn Leu Tyr Tyr Leu Gly Ile Phe Asn Ala Lys Asn Lys
545                 550                 555                 560

Pro Glu Lys Lys Ile Glu Gly Asn Thr Ser Glu Asn Lys Gly Asp
            565                 570                 575

Tyr Lys Lys Met Ile Tyr Asn Leu Leu Pro Gly Pro Asn Lys Met Ile
            580                 585                 590

Pro Lys Val Phe Leu Ser Ser Lys Thr Gly Val Glu Thr Tyr Lys Pro
            595                 600                 605

Ser Ala Tyr Ile Leu Glu Gly Tyr Lys Gln Asn Lys His Leu Lys Ser
            610                 615                 620

Ser Lys Asp Phe Asp Ile Thr Phe Cys Arg Asp Leu Ile Asp Tyr Phe
625                 630                 635                 640

Lys Asn Cys Ile Ala Ile His Pro Glu Trp Lys Asn Phe Gly Phe Asp
                645                 650                 655

Phe Ser Asp Thr Ser Thr Tyr Glu Asp Ile Ser Gly Phe Tyr Arg Glu
            660                 665                 670

Val Glu Leu Gln Gly Tyr Lys Ile Asp Trp Thr Tyr Ile Ser Glu Lys
            675                 680                 685

Asp Ile Asp Leu Leu Gln Glu Lys Gly Gln Leu Tyr Leu Phe Gln Ile
690                 695                 700

Tyr Asn Lys Asp Phe Ser Lys Lys Ser Thr Gly Asn Asp Asn Leu His
705                 710                 715                 720

Thr Met Tyr Leu Lys Asn Leu Phe Ser Glu Glu Asn Leu Lys Asp Val
                725                 730                 735

Val Leu Lys Leu Asn Gly Glu Ala Glu Ile Phe Phe Arg Lys Ser Ser
                740                 745                 750

Ile Lys Asn Pro Ile Ile His Lys Lys Gly Ser Ile Leu Val Asn Arg
            755                 760                 765

Thr Tyr Glu Ala Glu Glu Lys Asp Gln Phe Gly Asn Ile Gln Ile Val
            770                 775                 780

Arg Lys Thr Ile Pro Glu Asn Ile Tyr Gln Glu Leu Tyr Lys Tyr Phe
785                 790                 795                 800

Asn Asp Lys Ser Asp Lys Glu Leu Ser Asp Glu Ala Ala Lys Leu Lys
                805                 810                 815

Asn Ala Val Gly His His Glu Ala Ala Thr Asn Ile Val Lys Asp Tyr
                820                 825                 830

Arg Tyr Thr Tyr Asp Lys Tyr Phe Leu His Met Pro Ile Thr Ile Asn
            835                 840                 845

Phe Lys Ala Asn Lys Thr Ser Phe Ile Asn Asp Arg Ile Leu Gln Tyr
            850                 855                 860

Ile Ala Lys Glu Lys Asp Leu His Val Ile Gly Ile Asp Arg Gly Glu
865                 870                 875                 880

Arg Asn Leu Ile Tyr Val Ser Val Ile Asp Thr Cys Gly Asn Ile Val
                885                 890                 895

Glu Gln Lys Ser Phe Asn Ile Val Asn Gly Tyr Asp Tyr Gln Ile Lys
            900                 905                 910

Leu Lys Gln Gln Glu Gly Ala Arg Gln Ile Ala Arg Lys Glu Trp Lys
            915                 920                 925

Glu Ile Gly Lys Ile Lys Glu Ile Lys Glu Gly Tyr Leu Ser Leu Val
            930                 935                 940

Ile His Glu Ile Ser Lys Met Val Ile Lys Tyr Asn Ala Ile Ile Ala
945                 950                 955                 960
```

```
Met Glu Asp Leu Ser Tyr Gly Phe Lys Lys Gly Arg Phe Lys Val Glu
            965                 970                 975

Arg Gln Val Tyr Gln Lys Phe Glu Thr Met Leu Ile Asn Lys Leu Asn
        980                 985                 990

Tyr Leu Val Phe Lys Asp Ile Ser Ile Thr Glu Asn Gly Gly Leu Leu
    995                 1000                1005

Lys Gly Tyr Gln Leu Thr Tyr Ile Pro Glu Lys Leu Lys Asn Val
   1010                1015                1020

Gly His Gln Cys Gly Cys Ile Phe Tyr Val Pro Ala Ala Tyr Thr
   1025                1030                1035

Ser Lys Ile Asp Pro Thr Thr Gly Phe Val Asn Ile Phe Lys Phe
   1040                1045                1050

Lys Asp Leu Thr Val Asp Ala Lys Arg Glu Phe Ile Lys Lys Phe
   1055                1060                1065

Asp Ser Ile Arg Tyr Asp Ser Asp Lys Asn Leu Phe Cys Phe Thr
   1070                1075                1080

Phe Asp Tyr Asn Asn Phe Ile Thr Gln Asn Thr Val Met Ser Lys
   1085                1090                1095

Ser Ser Trp Ser Val Tyr Thr Tyr Gly Val Arg Ile Lys Arg Arg
   1100                1105                1110

Phe Val Asn Gly Arg Phe Ser Asn Glu Ser Asp Thr Ile Asp Ile
   1115                1120                1125

Thr Lys Asp Met Glu Lys Thr Leu Glu Met Thr Asp Ile Asn Trp
   1130                1135                1140

Arg Asp Gly His Asp Leu Arg Gln Asp Ile Ile Asp Tyr Glu Ile
   1145                1150                1155

Val Gln His Ile Phe Glu Ile Phe Lys Leu Thr Val Gln Met Arg
   1160                1165                1170

Asn Ser Leu Ser Glu Leu Glu Asp Arg Asn Tyr Asp Arg Leu Ile
   1175                1180                1185

Ser Pro Val Leu Asn Glu Asn Asn Ile Phe Tyr Asp Ser Ala Lys
   1190                1195                1200

Ala Gly Asp Ala Leu Pro Lys Asp Ala Asp Ala Asn Gly Ala Tyr
   1205                1210                1215

Cys Ile Ala Leu Lys Gly Leu Tyr Glu Ile Lys Gln Ile Thr Glu
   1220                1225                1230

Asn Trp Lys Glu Asp Gly Lys Phe Ser Arg Asp Lys Leu Lys Ile
   1235                1240                1245

Ser Asn Lys Asp Trp Phe Asp Phe Ile Gln Asn Lys Arg Tyr Leu
   1250                1255                1260

<210> SEQ ID NO 2
<211> LENGTH: 984
<212> TYPE: PRT
<213> ORGANISM: Lachnospira pectinoschiza

<400> SEQUENCE: 2

Met Phe Ser Leu Asp Tyr Phe Ser Leu Thr Leu Ser Gln Arg Tyr Ile
1               5                   10                  15

Asp Ile Tyr Asn Thr Met Ile Gly Gly Asn Thr Leu Ala Asp Gly Thr
            20                  25                  30

Lys Val Gln Gly Ile Asn Glu Asn Ile Asn Ile Tyr Arg Gln Lys Asn
        35                  40                  45

Asn Ile Asp Arg Lys Asn Leu Pro Thr Leu Lys Pro Leu His Lys Gln
    50                  55                  60
```

```
Leu Leu Ser Asp Arg Glu Thr Leu Ser Trp Ile Pro Glu Ala Phe Lys
 65                  70                  75                  80

Thr Lys Glu Glu Val Gly Ala Ile Glu Asp Phe Tyr Lys Asn Asn
                 85                  90                  95

Ile Ile Ser Phe Lys Cys Cys Asp Asn Ile Val Asp Ile Thr Lys Gln
            100                 105                 110

Phe Ile Asp Ile Phe Ser Leu Asn Glu Asp Tyr Glu Leu Asn Lys Ile
        115                 120                 125

Phe Ile Lys Asn Asp Ile Ser Ile Thr Ser Ile Ser Gln Asp Ile Phe
    130                 135                 140

Lys Asp Tyr Arg Ile Ile Lys Glu Ala Leu Trp Gln Lys His Ile Asn
145                 150                 155                 160

Glu Asn Pro Lys Ala Ala Lys Ser Lys Asp Leu Thr Gly Asp Lys Glu
                165                 170                 175

Lys Tyr Phe Ser Arg Lys Asn Ser Phe Phe Ser Phe Glu Glu Ile Ile
            180                 185                 190

Ser Ser Leu Lys Leu Met Gly Arg Lys Ile Asp Leu Phe Ser Tyr Phe
        195                 200                 205

Lys Asp Asn Val Glu Tyr Arg Ala His Ser Ile Glu Thr Thr Phe Ile
    210                 215                 220

Lys Trp Gln Lys Asn Lys Asn Asp Lys Lys Thr Thr Lys Glu Leu Leu
225                 230                 235                 240

Asp Asn Ile Leu Asn Leu Gln Arg Val Leu Lys Pro Leu Tyr Leu Lys
                245                 250                 255

Ala Glu Val Glu Lys Asp Ile Leu Phe Tyr Ser Ile Phe Asp Ile Tyr
            260                 265                 270

Phe Glu Ser Leu Asn Glu Ile Val Lys Leu Tyr Asn Lys Val Arg Asp
        275                 280                 285

Phe Glu Ser Lys Lys Pro Tyr Ser Leu Glu Lys Phe Lys Leu Asn Phe
    290                 295                 300

Gln Asn Ser Thr Leu Leu Ser Gly Trp Asp Val Asn Lys Glu Pro Asp
305                 310                 315                 320

Asn Thr Ser Ile Leu Leu Lys Lys Asp Gly Leu Tyr Tyr Leu Gly Ile
                325                 330                 335

Met Asp Lys Lys His Asn Arg Val Phe Lys Asn Leu Glu Ser Ser Lys
            340                 345                 350

Gly Gly Tyr Glu Lys Ile Glu Tyr Lys Leu Leu Ser Gly Pro Asn Lys
        355                 360                 365

Met Leu Pro Lys Val Phe Phe Ser Asn Lys Ser Ile Gly Tyr Tyr Asn
    370                 375                 380

Pro Ser Pro Ala Leu Leu Glu Lys Tyr Lys Ser Gly Val His Lys Lys
385                 390                 395                 400

Gly Glu Ser Phe Asp Leu Asn Phe Cys His Glu Leu Ile Asp Phe Phe
                405                 410                 415

Lys Ala Ser Ile Asp Lys His Glu Asp Trp Lys Asn Phe Asn Phe Lys
            420                 425                 430

Phe Ser Asp Thr Ser Glu Tyr Ala Asp Ile Ser Gly Phe Tyr Arg Glu
        435                 440                 445

Val Glu Gln Gln Gly Tyr Lys Ile Thr Phe Lys Asn Ile Asp Glu Glu
    450                 455                 460

Phe Ile Asn Thr Leu Ile Asn Glu Gly Lys Leu Tyr Leu Phe Gln Ile
465                 470                 475                 480
```

-continued

```
Tyr Asn Lys Asp Phe Ser Thr Phe Ser Lys Gly Thr Lys Asn Leu His
            485                 490                 495
Thr Leu Tyr Trp Glu Met Ile Phe Asn Glu Glu Asn Leu Lys Asn Val
        500                 505                 510
Val Tyr Lys Leu Asn Gly Glu Ala Glu Ile Phe Tyr Arg Lys Lys Ser
        515                 520                 525
Ile Glu Tyr Ser Glu Asp Lys Met Lys Tyr Gly His His Tyr Glu Glu
        530                 535                 540
Leu Lys Asp Lys Phe Asn Tyr Pro Ile Ile Lys Asp Lys Arg Phe Thr
545                 550                 555                 560
Met Asp Lys Phe Gln Phe His Val Pro Ile Thr Met Asn Phe Lys Ala
            565                 570                 575
Thr Gly Arg Ser Tyr Ile Asn Glu Glu Val Asn Asp Phe Leu Arg Gln
            580                 585                 590
Asn Ser Lys Asp Val Lys Ile Ile Gly Ile Asn Arg Gly Glu Arg His
            595                 600                 605
Leu Ile Tyr Leu Thr Met Ile Asn Ala Lys Gly Glu Ile Ile Gln Gln
        610                 615                 620
Tyr Ser Leu Asn Glu Ile Val Asn Ser Tyr Asn Asn Lys Asn Phe Thr
625                 630                 635                 640
Val Asn Tyr Asn Glu Lys Leu Ser Lys Lys Glu Gly Glu Arg Ala Ile
            645                 650                 655
Ala Arg Glu Asn Trp Gly Val Val Glu Asn Ile Lys Glu Leu Lys Glu
            660                 665                 670
Gly Tyr Leu Ser His Ala Ile His Thr Ile Ser Asn Leu Ile Val Glu
        675                 680                 685
Asn Asn Ala Ile Val Val Leu Glu Asp Leu Asn Phe Glu Phe Lys Arg
        690                 695                 700
Glu Arg Leu Lys Val Glu Lys Ser Ile Tyr Gln Lys Phe Glu Lys Met
705                 710                 715                 720
Leu Ile Asp Lys Leu Asn Tyr Leu Val Asp Lys Lys Lys Asp Ile Asn
            725                 730                 735
Glu Asn Gly Gly Leu Leu Lys Ala Leu Gln Leu Thr Asn Lys Phe Glu
            740                 745                 750
Ser Phe Glu Lys Ile Gly Lys Gln Asn Gly Phe Leu Phe Phe Val Asn
        755                 760                 765
Ala Trp Asn Ile Thr Lys Ile Cys Pro Val Thr Gly Phe Val Ser Leu
        770                 775                 780
Phe Asp Thr Arg Tyr Gln Ser Val Asp Lys Ala Arg Glu Phe Phe Ser
785                 790                 795                 800
Lys Phe Asp Ser Ile Lys Tyr Asn Glu Glu Lys Glu His Tyr Glu Phe
            805                 810                 815
Val Phe Asp Tyr Ser Asn Phe Thr Asp Lys Ala Lys Asp Thr Lys Thr
            820                 825                 830
Lys Trp Thr Val Cys Ser Tyr Gly Thr Arg Ile Lys Thr Phe Arg Asn
        835                 840                 845
Ser Glu Lys Asn Asn Asn Trp Asp Asn Lys Thr Val Ser Pro Thr Glu
        850                 855                 860
Asp Leu Ser Lys Leu Leu Lys Ser Cys Asp Arg Asp Ile Lys Glu Phe
865                 870                 875                 880
Ile Ile Ser Gln Asp Lys Lys Glu Phe Phe Val Glu Leu Leu Glu Ile
            885                 890                 895
Phe Ser Leu Ile Val Gln Met Lys Asn Ser Ile Ile Asn Ser Glu Ile
```

```
                900             905             910
Asp Tyr Ile Ile Ser Pro Val Ala Asn Glu Asn Gly Glu Phe Phe Asp
            915                 920                 925

Ser Arg Phe Ala Asn Ser Ser Leu Pro Lys Asn Ala Asp Ala Asn Ala
        930                 935                 940

Ala Tyr Asn Thr Ala Arg Lys Gly Leu Met Leu Glu Lys Ile Arg
945                 950                 955                 960

Asp Ser Glu Ile Gly Lys Lys Ile Asp Met Lys Ile Thr Asn Thr Glu
                965                 970                 975

Trp Leu Asn Phe Val Gln Glu Arg
            980

<210> SEQ ID NO 3
<211> LENGTH: 941
<212> TYPE: PRT
<213> ORGANISM: Sneathia amnii

<400> SEQUENCE: 3

Met Asn Asp Ile Glu Gly Leu Lys Glu Glu Phe Leu Lys Ile Ser Leu
1               5                   10                  15

Glu Asn Phe Glu Gly Ile Tyr Ile Ser Asn Lys Lys Leu Asn Glu Ile
            20                  25                  30

Ser Asn Arg Lys Phe Gly Asp Tyr Asn Ser Ile Asn Met Met Ile Lys
        35                  40                  45

Gln Ser Met Asn Glu Lys Gly Ile Leu Ser Lys Lys Glu Ile Asn Glu
    50                  55                  60

Leu Ile Pro Asp Leu Glu Asn Ile Asn Lys Pro Lys Val Lys Ser Phe
65                  70                  75                  80

Asn Leu Ser Phe Ile Phe Glu Asn Leu Thr Lys Glu His Lys Glu Leu
                85                  90                  95

Ile Ile Asp Tyr Ile Arg Glu Asn Ile Cys Asn Val Ile Glu Asn Val
            100                 105                 110

Lys Ile Thr Ile Glu Lys Tyr Arg Asn Ile Asp Asn Lys Ile Glu Phe
        115                 120                 125

Lys Asn Asn Ala Glu Lys Val Ser Lys Ile Lys Glu Met Leu Glu Ser
    130                 135                 140

Ile Asn Glu Leu Cys Lys Leu Ile Lys Glu Phe Asn Thr Asp Glu Ile
145                 150                 155                 160

Glu Lys Asn Asn Glu Phe Tyr Asn Ile Leu Asn Lys Asn Phe Glu Ile
                165                 170                 175

Phe Glu Ser Ser Tyr Lys Val Leu Asn Lys Val Arg Asn Phe Val Thr
            180                 185                 190

Lys Lys Glu Val Ile Glu Asn Lys Met Lys Leu Asn Phe Ser Asn Tyr
        195                 200                 205

Gln Leu Gly Asn Gly Trp His Lys Asn Lys Glu Lys Asp Cys Ser Ile
    210                 215                 220

Ile Leu Phe Arg Lys Arg Asn Asn Glu Arg Trp Ile Tyr Tyr Leu Gly
225                 230                 235                 240

Ile Leu Lys His Gly Thr Lys Ile Lys Glu Asn Asp Tyr Leu Ser Ser
                245                 250                 255

Val Asp Thr Gly Phe Tyr Lys Met Asp Tyr Tyr Ala Gln Asn Ser Leu
            260                 265                 270

Ser Lys Met Ile Pro Lys Cys Ser Ile Thr Val Lys Asn Val Lys Asn
        275                 280                 285
```

```
Ala Pro Glu Asp Glu Ser Val Ile Leu Asn Asp Ser Lys Lys Phe Asn
    290                 295                 300
Glu Pro Leu Glu Ile Thr Pro Glu Ile Arg Lys Leu Tyr Gly Asn Asn
305                 310                 315                 320
Glu His Ile Lys Gly Asp Lys Phe Lys Glu Ser Leu Val Lys Trp
                325                 330                 335
Ile Asp Phe Cys Lys Glu Phe Leu Leu Lys Tyr Lys Ser Phe Glu Lys
                340                 345                 350
Ala Lys Lys Glu Ile Leu Lys Leu Lys Glu Ser Asn Leu Tyr Glu Asn
        355                 360                 365
Leu Glu Glu Phe Tyr Ser Asp Ala Glu Glu Lys Ala Tyr Phe Leu Glu
    370                 375                 380
Phe Ile Asn Ile Asp Glu Asp Lys Ile Lys Lys Leu Val Lys Glu Lys
385                 390                 395                 400
Asn Leu Tyr Leu Phe Gln Ile Tyr Asn Lys Asp Phe Ser Ala Tyr Ser
                405                 410                 415
Thr Gly Asn Lys Asn Leu His Thr Met Tyr Phe Glu Glu Leu Phe Thr
            420                 425                 430
Asp Glu Asn Leu Lys Lys Pro Val Phe Lys Leu Asn Gly Asn Thr Glu
        435                 440                 445
Val Phe Tyr Arg Ile Ala Ser Ser Lys Pro Lys Ile Val His Asn Lys
    450                 455                 460
Gly Glu Lys Leu Val Asn Lys Thr Tyr Leu Asp Asp Gly Ile Ile Lys
465                 470                 475                 480
Thr Ile Pro Asp Ser Val Tyr Glu Glu Ile Ser Glu Lys Val Lys Asn
                485                 490                 495
Asn Glu Asp Tyr Ser Lys Leu Leu Glu Glu Asn Asn Ile Lys Asn Leu
            500                 505                 510
Glu Ile Lys Val Ala Thr His Glu Ile Val Lys Asp Lys Arg Tyr Phe
        515                 520                 525
Glu Asn Lys Phe Leu Phe Tyr Leu Pro Ile Thr Leu Asn Lys Lys Val
    530                 535                 540
Ser Asn Lys Asn Thr Asn Lys Asn Ile Asn Lys Asn Val Ile Asp Glu
545                 550                 555                 560
Ile Lys Asp Cys Asn Glu Tyr Asn Val Ile Gly Ile Asp Arg Gly Glu
                565                 570                 575
Arg Asn Leu Ile Ser Leu Cys Ile Ile Asn Gln Asn Gly Glu Ile Ile
            580                 585                 590
Leu Gln Lys Glu Met Asn Ile Ile Gln Ser Ser Asp Lys Tyr Asn Val
        595                 600                 605
Asp Tyr Asn Glu Lys Leu Glu Ile Lys Ser Lys Glu Arg Asp Asn Ala
    610                 615                 620
Lys Lys Asn Trp Ser Glu Ile Gly Lys Ile Lys Asp Leu Lys Ser Gly
625                 630                 635                 640
Tyr Leu Ser Ala Val His Glu Ile Val Lys Leu Ala Ile Glu Tyr
            645                 650                 655
Asn Ala Val Ile Ile Leu Glu Asp Leu Asn Asn Gly Phe Lys Asn Ser
            660                 665                 670
Arg Lys Lys Val Asp Lys Gln Ile Tyr Gln Lys Phe Glu Arg Ala Leu
        675                 680                 685
Ile Glu Lys Leu Gln Phe Leu Ile Phe Lys Asn Tyr Asp Lys Asn Glu
    690                 695                 700
Lys Gly Gly Leu Arg Asn Ala Phe Gln Leu Thr Pro Glu Leu Lys Asn
```

```
             705                 710                 715                 720

Ile Thr Lys Val Ala Ser Gln Gln Gly Ile Ile Ile Tyr Thr Asn Pro
                        725                 730                 735

Ala Tyr Thr Ser Lys Ile Asp Pro Thr Thr Gly Tyr Ala Asn Ile Ile
                        740                 745                 750

Lys Lys Ser Asn Asn Asn Glu Glu Ser Ile Val Lys Ala Ile Asp Lys
                        755                 760                 765

Ile Ser Tyr Asp Lys Glu Lys Asp Met Phe Tyr Phe Asp Ile Asn Leu
                        770                 775                 780

Ser Asn Ser Ser Phe Asn Leu Thr Val Lys Asn Val Leu Lys Lys Glu
        785                 790                 795                 800

Trp Arg Ile Tyr Thr Asn Gly Glu Arg Ile Ile Tyr Lys Asp Arg Lys
                        805                 810                 815

Tyr Ile Thr Leu Asn Ile Thr Gln Glu Met Lys Asp Ile Leu Ser Lys
                        820                 825                 830

Cys Gly Ile Asp Tyr Leu Asn Ile Asp Asn Leu Lys Gln Asp Ile Leu
                        835                 840                 845

Lys Asn Lys Leu His Lys Lys Val Tyr Tyr Ile Phe Glu Leu Ala Asn
                        850                 855                 860

Lys Met Arg Asn Glu Asn Lys Asp Val Asp Tyr Ile Ile Ser Pro Val
        865                 870                 875                 880

Leu Asn Lys Asp Gly Lys Phe Phe Met Thr Gln Glu Ile Asn Glu Leu
                        885                 890                 895

Thr Pro Lys Asp Ala Asp Leu Asn Gly Ala Tyr Asn Ile Ala Leu Lys
                        900                 905                 910

Gly Lys Leu Met Ile Asp Asn Leu Asn Lys Lys Glu Lys Phe Val Phe
                        915                 920                 925

Leu Ser Asn Glu Asp Trp Leu Asn Phe Ile Gln Gly Arg
        930                 935                 940

<210> SEQ ID NO 4
<211> LENGTH: 1310
<212> TYPE: PRT
<213> ORGANISM: Helcococcus kunzii

<400> SEQUENCE: 4

Met Phe Glu Lys Leu Ser Asn Ile Val Ser Ile Ser Lys Thr Ile Arg
        1               5                   10                  15

Phe Lys Leu Ile Pro Val Gly Lys Thr Leu Glu Asn Ile Glu Lys Leu
                        20                  25                  30

Gly Lys Leu Glu Lys Asp Phe Glu Arg Ser Asp Phe Tyr Pro Ile Leu
                        35                  40                  45

Lys Asn Ile Ser Asp Asp Tyr Tyr Arg Gln Tyr Ile Lys Glu Lys Leu
        50                  55                  60

Ser Asp Leu Asn Leu Asp Trp Gln Lys Leu Tyr Asp Ala His Glu Leu
        65                  70                  75                  80

Leu Asp Ser Ser Lys Glu Ser Gln Lys Asn Leu Glu Met Ile Gln
                        85                  90                  95

Ala Gln Tyr Arg Lys Val Leu Phe Asn Ile Leu Ser Gly Glu Leu Asp
                        100                 105                 110

Lys Ser Gly Glu Lys Asn Ser Lys Asp Leu Ile Lys Asn Asn Lys Ala
                        115                 120                 125

Leu Tyr Gly Lys Leu Phe Lys Lys Gln Phe Ile Leu Glu Val Leu Pro
                        130                 135                 140
```

-continued

```
Asp Phe Val Asn Asn Asn Asp Ser Tyr Ser Glu Glu Asp Leu Glu Gly
145                 150                 155                 160

Leu Asn Leu Tyr Ser Lys Phe Thr Thr Arg Leu Lys Asn Phe Trp Glu
                165                 170                 175

Thr Arg Lys Asn Val Phe Thr Asp Lys Asp Ile Val Thr Ala Ile Pro
            180                 185                 190

Phe Arg Ala Val Asn Glu Asn Phe Gly Phe Tyr Tyr Asp Asn Ile Lys
        195                 200                 205

Ile Phe Asn Lys Asn Ile Glu Tyr Leu Glu Asn Lys Ile Pro Asn Leu
    210                 215                 220

Glu Asn Glu Leu Lys Glu Ala Asp Ile Leu Asp Asp Asn Arg Ser Val
225                 230                 235                 240

Lys Asp Tyr Phe Thr Pro Asn Gly Phe Asn Tyr Val Ile Thr Gln Asp
                245                 250                 255

Gly Ile Asp Val Tyr Gln Ala Ile Arg Gly Gly Phe Thr Lys Glu Asn
            260                 265                 270

Gly Glu Lys Val Gln Gly Ile Asn Glu Ile Leu Asn Leu Thr Gln Gln
        275                 280                 285

Gln Leu Arg Arg Lys Pro Glu Thr Lys Asn Val Lys Leu Gly Val Leu
    290                 295                 300

Thr Lys Leu Arg Lys Gln Ile Leu Glu Tyr Ser Glu Ser Thr Ser Phe
305                 310                 315                 320

Leu Ile Asp Gln Ile Glu Asp Asp Asn Asp Leu Val Asp Arg Ile Asn
                325                 330                 335

Lys Phe Asn Val Ser Phe Phe Glu Ser Thr Glu Val Ser Pro Ser Leu
            340                 345                 350

Phe Glu Gln Ile Glu Arg Leu Tyr Asn Ala Leu Lys Ser Ile Lys Lys
        355                 360                 365

Glu Glu Val Tyr Ile Asp Ala Arg Asn Thr Gln Lys Phe Ser Gln Met
    370                 375                 380

Leu Phe Gly Gln Trp Asp Val Ile Arg Arg Gly Tyr Thr Val Lys Ile
385                 390                 395                 400

Thr Glu Gly Ser Lys Glu Glu Lys Lys Tyr Lys Glu Tyr Leu Glu
                405                 410                 415

Leu Asp Glu Thr Ser Lys Ala Lys Arg Tyr Leu Asn Ile Arg Glu Ile
            420                 425                 430

Glu Glu Leu Val Asn Leu Val Glu Gly Phe Glu Glu Val Asp Val Phe
        435                 440                 445

Ser Val Leu Leu Glu Lys Phe Lys Met Asn Asn Ile Glu Arg Ser Glu
450                 455                 460

Phe Glu Ala Pro Ile Tyr Gly Ser Pro Ile Lys Leu Glu Ala Ile Lys
465                 470                 475                 480

Glu Tyr Leu Glu Lys His Leu Glu Glu Tyr His Lys Trp Lys Leu Leu
                485                 490                 495

Leu Ile Gly Asn Asp Asp Leu Asp Thr Asp Glu Thr Phe Tyr Pro Leu
            500                 505                 510

Leu Asn Glu Val Ile Ser Asp Tyr Tyr Ile Ile Pro Leu Tyr Asn Leu
        515                 520                 525

Thr Arg Asn Tyr Leu Thr Arg Lys His Ser Asp Lys Asp Ile Lys
    530                 535                 540

Val Asn Phe Asp Phe Pro Thr Leu Ala Asp Gly Trp Ser Glu Ser Lys
545                 550                 555                 560

Ile Ser Asp Asn Arg Ser Ile Ile Leu Arg Lys Gly Gly Tyr Tyr Tyr
```

-continued

```
                565                 570                 575
Leu Gly Ile Leu Ile Asp Asn Lys Leu Leu Ile Asn Lys Lys Asn Lys
                580                 585                 590
Ser Lys Lys Ile Tyr Glu Ile Leu Ile Tyr Asn Gln Ile Pro Glu Phe
                595                 600                 605
Ser Lys Ser Ile Pro Asn Tyr Pro Phe Thr Lys Lys Val Lys Glu His
                610                 615                 620
Phe Lys Asn Asn Val Ser Asp Phe Gln Leu Ile Asp Gly Tyr Val Ser
625                 630                 635                 640
Pro Leu Ile Ile Thr Lys Glu Ile Tyr Asp Ile Lys Lys Glu Lys Lys
                645                 650                 655
Tyr Lys Lys Asp Phe Tyr Lys Asp Asn Asn Thr Asn Lys Asn Tyr Leu
                660                 665                 670
Tyr Thr Ile Tyr Lys Trp Ile Glu Phe Cys Lys Gln Phe Leu Tyr Lys
                675                 680                 685
Tyr Lys Gly Pro Asn Lys Glu Ser Tyr Lys Glu Met Tyr Asp Phe Ser
                690                 695                 700
Thr Leu Lys Asp Thr Ser Leu Tyr Val Asn Leu Asn Asp Phe Tyr Ala
705                 710                 715                 720
Asp Val Asn Ser Cys Ala Tyr Arg Val Leu Phe Asn Lys Ile Asp Glu
                725                 730                 735
Asn Thr Ile Asp Asn Ala Val Glu Asp Gly Lys Leu Leu Leu Phe Gln
                740                 745                 750
Ile Tyr Asn Lys Asp Phe Ser Pro Glu Ser Lys Gly Lys Lys Asn Leu
                755                 760                 765
His Thr Leu Tyr Trp Leu Ser Met Phe Ser Glu Glu Asn Leu Arg Thr
                770                 775                 780
Arg Lys Leu Lys Leu Asn Gly Gln Ala Glu Ile Phe Tyr Arg Lys Lys
785                 790                 795                 800
Leu Glu Lys Lys Pro Ile Ile His Lys Glu Gly Ser Ile Leu Leu Asn
                805                 810                 815
Lys Ile Asp Lys Glu Gly Asn Thr Ile Pro Glu Asn Ile Tyr His Glu
                820                 825                 830
Cys Tyr Arg Tyr Leu Asn Lys Lys Ile Gly Arg Glu Asp Leu Ser Asp
                835                 840                 845
Glu Ala Ile Ala Leu Phe Asn Lys Asp Val Leu Lys Tyr Lys Glu Ala
                850                 855                 860
Arg Phe Asp Ile Ile Lys Asp Arg Arg Tyr Ser Glu Ser Gln Phe Phe
865                 870                 875                 880
Phe His Val Pro Ile Thr Phe Asn Trp Asp Ile Lys Thr Asn Lys Asn
                885                 890                 895
Val Asn Gln Ile Val Gly Met Ile Lys Asp Gly Glu Ile Lys His
                900                 905                 910
Ile Ile Gly Ile Asp Arg Gly Glu Arg His Leu Leu Tyr Tyr Ser Val
                915                 920                 925
Ile Asp Leu Glu Gly Asn Ile Val Glu Gln Gly Ser Leu Asn Thr Leu
                930                 935                 940
Glu Gln Asn Arg Phe Asp Asn Ser Thr Val Lys Val Asp Tyr Gln Asn
945                 950                 955                 960
Lys Leu Arg Thr Arg Glu Glu Asp Arg Asp Ala Arg Lys Asn Trp
                965                 970                 975
Thr Asn Ile Asn Lys Ile Lys Glu Leu Lys Asp Gly Tyr Leu Ser His
                980                 985                 990
```

```
Val Val His Lys Leu Ser Arg Leu  Ile Ile Lys Tyr Glu  Ala Ile Val
        995             1000                  1005

Ile Met  Glu Asn Leu Asn Gln  Gly Phe Lys Arg Gly  Arg Phe Lys
    1010             1015                 1020

Val Glu  Arg Gln Val Tyr Gln  Lys Phe Glu Leu Ala  Leu Met Asn
    1025             1030                 1035

Lys Leu  Ser Ala Leu Ser Phe  Lys Glu Lys Tyr Asp  Glu Arg Lys
    1040             1045                 1050

Asn Leu  Glu Pro Ser Gly Ile  Leu Asn Pro Ile Gln  Ala Cys Tyr
    1055             1060                 1065

Pro Val  Asp Ala Tyr Gln Glu  Leu Gln Gly Gln Asn  Gly Ile Val
    1070             1075                 1080

Phe Tyr  Leu Pro Ala Ala Tyr  Thr Ser Val Ile Asp  Pro Val Thr
    1085             1090                 1095

Gly Phe  Thr Asn Leu Phe Arg  Leu Lys Ser Ile Asn  Ser Ser Lys
    1100             1105                 1110

Tyr Glu  Glu Phe Ile Lys Lys  Phe Lys Asn Ile Tyr  Phe Asp Asn
    1115             1120                 1125

Glu Glu  Glu Asp Phe Lys Phe  Ile Phe Asn Tyr Lys  Asp Phe Ala
    1130             1135                 1140

Lys Ala  Asn Leu Val Ile Leu  Asn Asn Ile Lys Ser  Lys Asp Trp
    1145             1150                 1155

Lys Ile  Ser Thr Arg Gly Glu  Arg Ile Ser Tyr Asn  Ser Lys Lys
    1160             1165                 1170

Lys Glu  Tyr Phe Tyr Val Gln  Pro Thr Glu Phe Leu  Ile Asn Lys
    1175             1180                 1185

Leu Lys  Glu Leu Asn Ile Asp  Tyr Glu Asn Ile Asp  Ile Ile Pro
    1190             1195                 1200

Leu Ile  Asp Asn Leu Glu Glu  Lys Ala Lys Arg Lys  Ile Leu Lys
    1205             1210                 1215

Ala Leu  Phe Asp Thr Phe Lys  Tyr Ser Val Gln Leu  Arg Asn Tyr
    1220             1225                 1230

Asp Phe  Glu Asn Asp Tyr Ile  Ile Ser Pro Thr Ala  Asp Asp Asn
    1235             1240                 1245

Gly Asn  Tyr Tyr Asn Ser Asn  Glu Ile Asp Ile Asp  Lys Thr Asn
    1250             1255                 1260

Leu Pro  Asn Asn Gly Asp Ala  Asn Gly Ala Phe Asn  Ile Ala Arg
    1265             1270                 1275

Lys Gly  Leu Leu Leu Lys Asp  Arg Ile Val Asn Ser  Asn Glu Ser
    1280             1285                 1290

Lys Val  Asp Leu Lys Ile Lys  Asn Glu Asp Trp Ile  Asn Phe Ile
    1295             1300                 1305

Ile Ser
    1310

<210> SEQ ID NO 5
<211> LENGTH: 984
<212> TYPE: PRT
<213> ORGANISM: Arcobacter butzleri

<400> SEQUENCE: 5

Met Phe Ser Leu Asp Tyr Phe Ser Leu Thr Leu Ser Gln Arg Tyr Ile
1               5                   10                  15

Asp Ile Tyr Asn Thr Met Ile Gly Gly Asn Thr Leu Ala Asp Gly Thr
```

```
            20                  25                  30
Lys Val Gln Gly Ile Asn Glu Asn Ile Asn Ile Tyr Arg Gln Lys Asn
            35                  40                  45

Asn Ile Asp Arg Lys Asn Leu Pro Thr Leu Lys Pro Leu His Lys Gln
 50                  55                  60

Leu Leu Ser Asp Arg Glu Thr Leu Ser Trp Ile Pro Glu Ala Phe Lys
 65                  70                  75                  80

Thr Lys Glu Glu Val Val Gly Ala Ile Glu Asp Phe Tyr Lys Asn Asn
                    85                  90                  95

Ile Ile Ser Phe Lys Cys Cys Asp Asn Ile Val Asp Ile Thr Lys Gln
                100                 105                 110

Phe Ile Asp Ile Phe Ser Leu Asn Glu Asp Tyr Glu Leu Asn Lys Ile
                115                 120                 125

Phe Ile Lys Asn Asp Ile Ser Ile Thr Ser Ile Ser Gln Asp Ile Phe
                130                 135                 140

Lys Asp Tyr Arg Ile Ile Lys Glu Ala Leu Trp Gln Lys His Ile Asn
145                 150                 155                 160

Glu Asn Pro Lys Ala Ala Lys Ser Lys Asp Leu Thr Gly Asp Lys Glu
                165                 170                 175

Lys Tyr Phe Ser Arg Lys Asn Ser Phe Ser Phe Glu Glu Ile Ile
                180                 185                 190

Ser Ser Leu Lys Leu Met Gly Arg Lys Ile Asp Leu Phe Ser Tyr Phe
                195                 200                 205

Lys Asp Asn Val Glu Tyr Arg Ala His Ser Ile Glu Thr Thr Phe Ile
                210                 215                 220

Lys Trp Gln Lys Asn Lys Asn Asp Lys Lys Thr Thr Lys Glu Leu Leu
225                 230                 235                 240

Asp Asn Ile Leu Asn Leu Gln Arg Val Leu Lys Pro Leu Tyr Leu Lys
                245                 250                 255

Ala Glu Val Glu Lys Asp Ile Leu Phe Tyr Ser Ile Phe Asp Ile Tyr
                260                 265                 270

Phe Glu Ser Leu Asn Glu Ile Val Lys Leu Tyr Asn Lys Val Arg Asp
                275                 280                 285

Phe Glu Ser Lys Lys Pro Tyr Ser Leu Glu Lys Phe Lys Leu Asn Phe
                290                 295                 300

Gln Asn Ser Thr Leu Leu Ser Gly Trp Asp Val Asn Lys Glu Pro Asp
305                 310                 315                 320

Asn Thr Ser Ile Leu Leu Lys Lys Asp Gly Leu Tyr Tyr Leu Gly Ile
                325                 330                 335

Met Asp Lys Lys His Asn Arg Val Phe Lys Asn Leu Glu Ser Ser Lys
                340                 345                 350

Gly Gly Tyr Glu Lys Ile Glu Tyr Lys Leu Leu Ser Gly Pro Asn Lys
                355                 360                 365

Met Leu Pro Lys Val Phe Phe Ser Asn Lys Ser Ile Gly Tyr Tyr Asn
                370                 375                 380

Pro Ser Pro Ala Leu Leu Glu Lys Tyr Lys Ser Gly Val His Lys Lys
385                 390                 395                 400

Gly Glu Ser Phe Asp Leu Asn Phe Cys His Glu Leu Ile Asp Phe Phe
                405                 410                 415

Lys Ala Ser Ile Asp Lys His Glu Asp Trp Lys Asn Phe Asn Phe Lys
                420                 425                 430

Phe Ser Asp Thr Ser Glu Tyr Ala Asp Ile Ser Gly Phe Tyr Arg Glu
                435                 440                 445
```

```
Val Glu Gln Gln Gly Tyr Lys Ile Thr Phe Lys Asn Ile Asp Glu Glu
    450                 455                 460

Phe Ile Asn Thr Leu Ile Asn Glu Gly Lys Leu Tyr Leu Phe Gln Ile
465                 470                 475                 480

Tyr Asn Lys Asp Phe Ser Thr Phe Ser Lys Gly Thr Lys Asn Leu His
                485                 490                 495

Thr Leu Tyr Trp Glu Met Ile Phe Asn Glu Glu Asn Leu Lys Asn Val
            500                 505                 510

Val Tyr Lys Leu Asn Gly Glu Ala Glu Ile Phe Tyr Arg Lys Lys Ser
        515                 520                 525

Ile Glu Tyr Ser Glu Asp Lys Met Lys Tyr Gly His His Tyr Glu Glu
    530                 535                 540

Leu Lys Asp Lys Phe Asn Tyr Pro Ile Ile Lys Asp Lys Arg Phe Thr
545                 550                 555                 560

Met Asp Lys Phe Gln Phe His Val Pro Ile Thr Met Asn Phe Lys Ala
                565                 570                 575

Thr Gly Arg Ser Tyr Ile Asn Glu Glu Val Asn Asp Phe Leu Arg Gln
            580                 585                 590

Asn Ser Lys Asp Val Lys Ile Ile Gly Ile Asn Arg Gly Glu Arg His
        595                 600                 605

Leu Ile Tyr Leu Thr Met Ile Asn Ala Lys Gly Glu Ile Ile Gln Gln
610                 615                 620

Tyr Ser Leu Asn Glu Ile Val Asn Ser Tyr Asn Asn Lys Asn Phe Thr
625                 630                 635                 640

Val Asn Tyr Asn Glu Lys Leu Ser Lys Lys Glu Gly Glu Arg Ala Ile
                645                 650                 655

Ala Arg Glu Asn Trp Gly Val Val Glu Asn Ile Lys Glu Leu Lys Glu
            660                 665                 670

Gly Tyr Leu Ser His Ala Ile His Thr Ile Ser Asn Leu Ile Val Glu
        675                 680                 685

Asn Asn Ala Ile Val Val Leu Glu Asp Leu Asn Phe Glu Phe Lys Arg
690                 695                 700

Glu Arg Leu Lys Val Glu Lys Ser Ile Tyr Gln Lys Phe Glu Lys Met
705                 710                 715                 720

Leu Ile Asp Lys Leu Asn Tyr Leu Val Asp Lys Lys Asp Ile Asn
                725                 730                 735

Glu Asn Gly Gly Leu Leu Lys Ala Leu Gln Leu Thr Asn Lys Phe Glu
            740                 745                 750

Ser Phe Glu Lys Ile Gly Lys Gln Asn Gly Phe Leu Phe Phe Val Asn
        755                 760                 765

Ala Trp Asn Ile Thr Lys Ile Cys Pro Val Thr Gly Phe Val Ser Leu
770                 775                 780

Phe Asp Thr Arg Tyr Gln Ser Val Asp Lys Ala Arg Glu Phe Phe Ser
785                 790                 795                 800

Lys Phe Asp Ser Ile Lys Tyr Asn Glu Glu Lys Glu His Tyr Glu Phe
                805                 810                 815

Val Phe Asp Tyr Ser Asn Phe Thr Asp Lys Ala Lys Asp Thr Lys Thr
            820                 825                 830

Lys Trp Thr Val Cys Ser Tyr Gly Thr Arg Ile Lys Thr Phe Arg Asn
        835                 840                 845

Ser Glu Lys Asn Asn Asn Trp Asp Asn Lys Thr Val Ser Pro Thr Glu
    850                 855                 860
```

-continued

```
Asp Leu Ser Lys Leu Leu Lys Ser Cys Asp Arg Asp Ile Lys Glu Phe
865                 870                 875                 880

Ile Ile Ser Gln Asp Lys Lys Glu Phe Phe Val Glu Leu Leu Glu Ile
            885                 890                 895

Phe Ser Leu Ile Val Gln Met Lys Asn Ser Ile Ile Asn Ser Glu Ile
        900                 905                 910

Asp Tyr Ile Ile Ser Pro Val Ala Asn Glu Asn Gly Glu Phe Phe Asp
    915                 920                 925

Ser Arg Phe Ala Asn Ser Ser Leu Pro Lys Asn Ala Asp Ala Asn Ala
930                 935                 940

Ala Tyr Asn Thr Ala Arg Lys Gly Leu Met Leu Leu Glu Lys Ile Arg
945                 950                 955                 960

Asp Ser Glu Ile Gly Lys Lys Ile Asp Met Lys Ile Thr Asn Thr Glu
                965                 970                 975

Trp Leu Asn Phe Val Gln Glu Arg
            980

<210> SEQ ID NO 6
<211> LENGTH: 1262
<212> TYPE: PRT
<213> ORGANISM: Bacteroidetes oral

<400> SEQUENCE: 6

Met Arg Lys Phe Asn Glu Phe Val Gly Leu Tyr Pro Ile Ser Lys Thr
1               5                   10                  15

Leu Arg Phe Glu Leu Lys Pro Ile Gly Lys Thr Leu Glu His Ile Gln
            20                  25                  30

Arg Asn Lys Leu Leu Glu His Asp Ala Val Arg Ala Asp Asp Tyr Val
        35                  40                  45

Lys Val Lys Lys Ile Ile Asp Lys Tyr His Lys Cys Leu Ile Asp Glu
    50                  55                  60

Ala Leu Ser Gly Phe Thr Phe Asp Thr Glu Ala Asp Gly Arg Ser Asn
65                  70                  75                  80

Asn Ser Leu Ser Glu Tyr Tyr Leu Tyr Asn Leu Lys Lys Arg Asn
                85                  90                  95

Glu Gln Glu Gln Lys Thr Phe Lys Thr Ile Gln Asn Asn Leu Arg Lys
            100                 105                 110

Gln Ile Val Asn Lys Leu Thr Gln Ser Glu Lys Tyr Lys Arg Ile Asp
        115                 120                 125

Lys Lys Glu Leu Ile Thr Thr Asp Leu Pro Asp Phe Leu Thr Asn Glu
    130                 135                 140

Ser Glu Lys Glu Leu Val Glu Lys Phe Lys Asn Phe Thr Thr Tyr Phe
145                 150                 155                 160

Thr Glu Phe His Lys Asn Arg Lys Asn Met Tyr Ser Lys Glu Glu Lys
                165                 170                 175

Ser Thr Ala Ile Ala Phe Arg Leu Ile Asn Glu Asn Leu Pro Lys Phe
            180                 185                 190

Val Asp Asn Ile Ala Ala Phe Glu Lys Val Val Ser Ser Pro Leu Ala
        195                 200                 205

Glu Lys Ile Asn Ala Leu Tyr Glu Asp Phe Lys Glu Tyr Leu Asn Val
    210                 215                 220

Glu Glu Ile Ser Arg Val Phe Arg Leu Asp Tyr Tyr Asp Glu Leu Leu
225                 230                 235                 240

Thr Gln Lys Gln Ile Asp Leu Tyr Asn Ala Ile Val Gly Gly Arg Thr
                245                 250                 255
```

```
Glu Glu Asp Asn Lys Ile Gln Ile Lys Gly Leu Asn Gln Tyr Ile Asn
            260                 265                 270

Glu Tyr Asn Gln Gln Thr Asp Arg Ser Asn Arg Leu Pro Lys Leu
        275                 280                 285

Lys Pro Leu Tyr Lys Gln Ile Leu Ser Asp Arg Glu Ser Val Ser Trp
    290                 295                 300

Leu Pro Pro Lys Phe Asp Ser Asp Lys Asn Leu Leu Ile Lys Ile Lys
305                 310                 315                 320

Glu Cys Tyr Asp Ala Leu Ser Glu Lys Glu Lys Val Phe Asp Lys Leu
                325                 330                 335

Glu Ser Ile Leu Lys Ser Leu Ser Thr Tyr Asp Leu Ser Lys Ile Tyr
                340                 345                 350

Ile Ser Asn Asp Ser Gln Leu Ser Tyr Ile Ser Gln Lys Met Phe Gly
                355                 360                 365

Arg Trp Asp Ile Ile Ser Lys Ala Ile Arg Glu Asp Cys Ala Lys Arg
    370                 375                 380

Asn Pro Gln Lys Ser Arg Glu Ser Leu Glu Lys Phe Ala Glu Arg Ile
385                 390                 395                 400

Asp Lys Lys Leu Lys Thr Ile Asp Ser Ile Ser Ile Gly Asp Val Asp
                405                 410                 415

Glu Cys Leu Ala Gln Leu Gly Glu Thr Tyr Val Lys Arg Val Glu Asp
                420                 425                 430

Tyr Phe Val Ala Met Gly Glu Ser Glu Ile Asp Asp Glu Gln Thr Asp
        435                 440                 445

Thr Thr Ser Phe Lys Lys Asn Ile Glu Gly Ala Tyr Glu Ser Val Lys
        450                 455                 460

Glu Leu Leu Asn Asn Ala Asp Asn Ile Thr Asp Asn Asn Leu Met Gln
465                 470                 475                 480

Asp Lys Gly Asn Val Glu Lys Ile Lys Thr Leu Leu Asp Ala Ile Lys
                485                 490                 495

Asp Leu Gln Arg Phe Ile Lys Pro Leu Leu Gly Lys Gly Asp Glu Ala
            500                 505                 510

Asp Lys Asp Gly Val Phe Tyr Gly Glu Phe Thr Ser Leu Trp Thr Lys
            515                 520                 525

Leu Asp Gln Val Thr Pro Leu Tyr Asn Met Val Arg Asn Tyr Leu Thr
    530                 535                 540

Ser Lys Pro Tyr Ser Thr Lys Lys Ile Lys Leu Asn Phe Glu Asn Ser
545                 550                 555                 560

Thr Leu Met Asp Gly Trp Asp Leu Asn Lys Glu Pro Asp Asn Thr Thr
                565                 570                 575

Val Ile Phe Cys Lys Asp Gly Leu Tyr Tyr Leu Gly Ile Met Gly Lys
                580                 585                 590

Lys Tyr Asn Arg Val Phe Val Asp Arg Glu Asp Leu Pro His Asp Gly
            595                 600                 605

Glu Cys Tyr Asp Lys Met Glu Tyr Lys Leu Leu Pro Gly Ala Asn Lys
            610                 615                 620

Met Leu Pro Lys Val Phe Phe Ser Glu Thr Gly Ile Gln Arg Phe Leu
625                 630                 635                 640

Pro Ser Glu Glu Leu Leu Gly Lys Tyr Glu Arg Gly Thr His Lys Lys
                645                 650                 655

Gly Ala Gly Phe Asp Leu Gly Asp Cys Arg Ala Leu Ile Asp Phe Phe
            660                 665                 670
```

-continued

```
Lys Lys Ser Ile Glu Arg His Asp Asp Trp Lys Lys Phe Asp Phe Lys
            675                 680                 685

Phe Ser Asp Thr Ser Thr Tyr Gln Asp Ile Ser Glu Phe Tyr Arg Glu
        690                 695                 700

Val Glu Gln Gln Gly Tyr Lys Met Ser Phe Arg Lys Val Ser Val Asp
705                 710                 715                 720

Tyr Ile Lys Ser Leu Val Glu Glu Gly Lys Leu Tyr Leu Phe Gln Ile
                725                 730                 735

Tyr Asn Lys Asp Phe Ser Ala His Ser Lys Gly Thr Pro Asn Met His
            740                 745                 750

Thr Leu Tyr Trp Lys Met Leu Phe Asp Glu Glu Asn Leu Lys Asp Val
        755                 760                 765

Val Tyr Lys Leu Asn Gly Glu Ala Glu Val Phe Phe Arg Lys Ser Ser
770                 775                 780

Ile Thr Val Gln Ser Pro Thr His Pro Ala Asn Ser Pro Ile Lys Asn
785                 790                 795                 800

Lys Asn Lys Asp Asn Gln Lys Lys Glu Ser Lys Phe Glu Tyr Asp Leu
            805                 810                 815

Ile Lys Asp Arg Arg Tyr Thr Val Asp Lys Phe Leu Phe His Val Pro
        820                 825                 830

Ile Thr Met Asn Phe Lys Ser Val Gly Gly Ser Asn Ile Asn Gln Leu
    835                 840                 845

Val Lys Arg His Ile Arg Ser Ala Thr Asp Leu His Ile Ile Gly Ile
850                 855                 860

Asp Arg Gly Glu Arg His Leu Leu Tyr Leu Thr Val Ile Asp Ser Arg
865                 870                 875                 880

Gly Asn Ile Lys Glu Gln Phe Ser Leu Asn Glu Ile Val Asn Glu Tyr
            885                 890                 895

Asn Gly Asn Thr Tyr Arg Thr Asp Tyr His Glu Leu Leu Asp Thr Arg
        900                 905                 910

Glu Gly Glu Arg Thr Glu Ala Arg Arg Asn Trp Gln Thr Ile Gln Asn
    915                 920                 925

Ile Arg Glu Leu Lys Glu Gly Tyr Leu Ser Gln Val Ile His Lys Ile
    930                 935                 940

Ser Glu Leu Ala Ile Lys Tyr Asn Ala Val Ile Val Leu Glu Asp Leu
945                 950                 955                 960

Asn Phe Gly Phe Met Arg Ser Arg Gln Lys Val Glu Lys Gln Val Tyr
            965                 970                 975

Gln Lys Phe Glu Lys Met Leu Ile Asp Lys Leu Asn Tyr Leu Val Asp
        980                 985                 990

Lys Lys Lys Pro Val Ala Glu Thr Gly Gly Leu Leu Arg Ala Tyr Gln
995                 1000                1005

Leu Thr Gly Glu Phe Glu Ser Phe Lys Thr Leu Gly Lys Gln Ser
    1010                1015                1020

Gly Ile Leu Phe Tyr Val Pro Ala Trp Asn Thr Ser Lys Ile Asp
    1025                1030                1035

Pro Val Thr Gly Phe Val Asn Leu Phe Asp Thr His Tyr Glu Asn
    1040                1045                1050

Ile Glu Lys Ala Lys Val Phe Phe Asp Lys Phe Lys Ser Ile Arg
    1055                1060                1065

Tyr Asn Ser Asp Lys Asp Trp Phe Glu Phe Val Val Asp Asp Tyr
    1070                1075                1080

Thr Arg Phe Ser Pro Lys Ala Glu Gly Thr Arg Arg Asp Trp Thr
```

```
                    1085                1090                1095

Ile Cys Thr Gln Gly Lys Arg Ile Gln Ile Cys Arg Asn His Gln
        1100                1105                1110

Arg Asn Asn Glu Trp Glu Gly Gln Glu Ile Asp Leu Thr Lys Ala
        1115                1120                1125

Phe Lys Glu His Phe Glu Ala Tyr Gly Val Asp Ile Ser Lys Asp
        1130                1135                1140

Leu Arg Glu Gln Ile Asn Thr Gln Asn Lys Lys Glu Phe Phe Glu
        1145                1150                1155

Glu Leu Leu Arg Leu Leu Arg Leu Thr Leu Gln Met Arg Asn Ser
        1160                1165                1170

Met Pro Ser Ser Asp Ile Asp Tyr Leu Ile Ser Pro Val Ala Asn
        1175                1180                1185

Asp Thr Gly Cys Phe Phe Asp Ser Arg Lys Gln Ala Glu Leu Lys
        1190                1195                1200

Glu Asn Ala Val Leu Pro Met Asn Ala Asp Ala Asn Gly Ala Tyr
        1205                1210                1215

Asn Ile Ala Arg Lys Gly Leu Leu Ala Ile Arg Lys Met Lys Gln
        1220                1225                1230

Glu Glu Asn Asp Ser Ala Lys Ile Ser Leu Ala Ile Ser Asn Lys
        1235                1240                1245

Glu Trp Leu Lys Phe Ala Gln Thr Lys Pro Tyr Leu Glu Asp
        1250                1255                1260

<210> SEQ ID NO 7
<211> LENGTH: 1222
<212> TYPE: PRT
<213> ORGANISM: Oribacterium sp.

<400> SEQUENCE: 7

Met Glu Thr Glu Ile Leu Lys Tyr Asp Phe Phe Glu Arg Glu Gly Lys
1               5                   10                  15

Tyr Met Tyr Tyr Asp Gly Leu Thr Lys Gln Tyr Ala Leu Ser Lys Thr
                20                  25                  30

Ile Arg Asn Glu Leu Val Pro Ile Gly Lys Thr Leu Asp Asn Ile Lys
            35                  40                  45

Lys Asn Arg Ile Leu Glu Ala Asp Ile Lys Arg Lys Ser Asp Tyr Glu
        50                  55                  60

His Val Lys Lys Leu Met Asp Met Tyr His Lys Lys Ile Ile Asn Glu
65                  70                  75                  80

Ala Leu Asp Asn Phe Lys Leu Ser Val Leu Glu Asp Ala Ala Asp Ile
                85                  90                  95

Tyr Phe Asn Lys Gln Asn Asp Glu Arg Asp Ile Asp Ala Phe Leu Lys
            100                 105                 110

Ile Gln Asp Lys Leu Arg Lys Glu Ile Val Glu Gln Leu Lys Gly His
        115                 120                 125

Thr Asp Tyr Ser Lys Val Gly Asn Lys Asp Phe Leu Gly Leu Leu Lys
    130                 135                 140

Ala Ala Ser Thr Glu Glu Asp Arg Ile Leu Ile Glu Ser Phe Asp Asn
145                 150                 155                 160

Phe Tyr Thr Tyr Phe Thr Ser Tyr Asn Lys Val Arg Ser Asn Leu Tyr
                165                 170                 175

Ser Ala Glu Asp Lys Ser Ser Thr Val Ala Tyr Arg Leu Ile Asn Glu
            180                 185                 190
```

```
Asn Leu Pro Lys Phe Asp Asn Ile Lys Ala Tyr Arg Thr Val Arg
        195                 200                 205
Asn Ala Gly Val Ile Ser Gly Asp Met Ser Ile Val Glu Gln Asp Glu
    210                 215                 220
Leu Phe Glu Val Asp Thr Phe Asn His Thr Leu Thr Gln Tyr Gly Ile
225                 230                 235                 240
Asp Thr Tyr Asn His Met Ile Gly Gln Leu Asn Ser Ala Ile Asn Leu
                245                 250                 255
Tyr Asn Gln Lys Met His Gly Ala Gly Ser Phe Lys Lys Leu Pro Lys
            260                 265                 270
Met Lys Glu Leu Tyr Lys Gln Leu Leu Thr Glu Arg Glu Glu Glu Phe
        275                 280                 285
Ile Glu Glu Tyr Thr Asp Asp Glu Val Leu Ile Thr Ser Val His Asn
        290                 295                 300
Tyr Val Ser Tyr Leu Ile Asp Tyr Leu Asn Ser Asp Lys Val Glu Ser
305                 310                 315                 320
Phe Phe Asp Thr Leu Arg Lys Ser Asp Gly Lys Glu Val Phe Ile Lys
                325                 330                 335
Asn Asp Val Ser Lys Thr Thr Met Ser Asn Ile Leu Phe Asp Asn Trp
            340                 345                 350
Ser Thr Ile Asp Asp Leu Ile Asn His Glu Tyr Asp Ser Ala Pro Glu
        355                 360                 365
Asn Val Lys Lys Thr Lys Asp Asp Lys Tyr Phe Glu Lys Arg Gln Lys
        370                 375                 380
Asp Leu Lys Lys Asn Lys Ser Tyr Ser Leu Ser Lys Ile Ala Ala Leu
385                 390                 395                 400
Cys Arg Asp Thr Thr Ile Leu Glu Lys Tyr Ile Arg Arg Leu Val Asp
                405                 410                 415
Asp Ile Glu Lys Ile Tyr Thr Ser Asn Asn Val Phe Ser Asp Ile Val
            420                 425                 430
Leu Ser Lys His Asp Arg Ser Lys Lys Leu Ser Lys Asn Thr Asn Ala
        435                 440                 445
Val Gln Ala Ile Lys Asn Met Leu Asp Ser Ile Lys Asp Phe Glu His
    450                 455                 460
Asp Val Met Leu Ile Asn Gly Ser Gly Gln Glu Ile Lys Lys Asn Leu
465                 470                 475                 480
Asn Val Tyr Ser Glu Gln Glu Ala Leu Ala Gly Ile Leu Arg Gln Val
                485                 490                 495
Asp His Ile Tyr Asn Leu Thr Arg Asn Tyr Leu Thr Lys Lys Pro Phe
            500                 505                 510
Ser Thr Glu Lys Ile Lys Leu Asn Phe Asn Arg Pro Thr Phe Leu Asp
        515                 520                 525
Gly Trp Asp Lys Asn Lys Glu Glu Ala Asn Leu Gly Ile Leu Leu Ile
    530                 535                 540
Lys Asp Asn Arg Tyr Tyr Leu Gly Ile Met Asn Thr Ser Ser Asn Lys
545                 550                 555                 560
Ala Phe Val Asn Pro Pro Lys Ala Ile Ser Asn Asp Ile Tyr Lys Lys
                565                 570                 575
Val Asp Tyr Lys Leu Leu Pro Gly Pro Asn Lys Met Leu Pro Lys Val
            580                 585                 590
Phe Phe Ala Thr Lys Asn Ile Ala Tyr Tyr Ala Pro Ser Glu Glu Leu
        595                 600                 605
Leu Ser Lys Tyr Arg Lys Gly Thr His Lys Lys Gly Asp Ser Phe Ser
```

```
            610                 615                 620
Ile Asp Asp Cys Arg Asn Leu Ile Asp Phe Phe Lys Ser Ser Ile Asn
625                 630                 635                 640

Lys Asn Thr Asp Trp Ser Thr Phe Gly Phe Asn Phe Ser Asp Thr Asn
                645                 650                 655

Ser Tyr Asn Asp Ile Ser Asp Phe Tyr Arg Glu Val Glu Lys Gln Gly
                660                 665                 670

Tyr Lys Leu Ser Phe Thr Asp Ile Asp Ala Cys Tyr Ile Lys Asp Leu
                675                 680                 685

Val Asp Asn Asn Glu Leu Tyr Leu Phe Gln Ile Tyr Asn Lys Asp Phe
690                 695                 700

Ser Pro Tyr Ser Lys Gly Lys Leu Asn Leu His Thr Leu Tyr Phe Lys
705                 710                 715                 720

Met Leu Phe Asp Gln Arg Asn Leu Asp Asn Val Val Tyr Lys Leu Asn
                725                 730                 735

Gly Glu Ala Glu Val Phe Tyr Arg Pro Ala Ser Ile Glu Ser Asp Glu
                740                 745                 750

Gln Ile Ile His Lys Ser Gly Gln Asn Ile Lys Asn Lys Asn Gln Lys
                755                 760                 765

Arg Ser Asn Cys Lys Lys Thr Ser Phe Asp Tyr Asp Ile Val Lys
770                 775                 780

Asp Arg Arg Tyr Cys Lys Asp Lys Phe Met Leu His Leu Pro Ile Thr
785                 790                 795                 800

Val Asn Phe Gly Thr Asn Glu Ser Gly Lys Phe Asn Glu Leu Val Asn
                805                 810                 815

Asn Ala Ile Arg Ala Asp Lys Asp Val Asn Val Ile Gly Ile Asp Arg
                820                 825                 830

Gly Glu Arg Asn Leu Leu Tyr Val Val Val Asp Pro Cys Gly Lys
                835                 840                 845

Ile Ile Glu Gln Ile Ser Leu Asn Thr Ile Val Asp Lys Glu Tyr Asp
850                 855                 860

Ile Glu Thr Asp Tyr His Gln Leu Leu Asp Glu Lys Glu Gly Ser Arg
865                 870                 875                 880

Asp Lys Ala Arg Lys Asp Trp Asn Thr Ile Glu Asn Ile Lys Glu Leu
                885                 890                 895

Lys Glu Gly Tyr Leu Ser Gln Val Val Asn Ile Ala Lys Leu Val
                900                 905                 910

Leu Lys Tyr Asp Ala Ile Ile Cys Leu Glu Asp Leu Asn Phe Gly Phe
                915                 920                 925

Lys Arg Gly Arg Gln Lys Val Glu Lys Gln Val Tyr Gln Lys Phe Glu
                930                 935                 940

Lys Met Leu Ile Asp Lys Met Asn Tyr Leu Val Leu Asp Lys Ser Arg
945                 950                 955                 960

Lys Gln Glu Ser Pro Gln Lys Pro Gly Gly Ala Leu Asn Ala Leu Gln
                965                 970                 975

Leu Thr Ser Ala Phe Lys Ser Phe Lys Glu Leu Gly Lys Gln Thr Gly
                980                 985                 990

Ile Ile Tyr Tyr Val Pro Ala Tyr  Leu Thr Ser Lys Ile  Asp Pro Thr
                995                 1000                1005

Thr Gly  Phe Ala Asn Leu Phe  Tyr Ile Lys Tyr Glu  Ser Val Asp
    1010                1015                1020

Lys Ala  Arg Asp Phe Phe Ser  Lys Phe Asp Phe Ile  Arg Tyr Asn
    1025                1030                1035
```

```
Gln Met Asp Asn Tyr Phe Glu Phe Gly Phe Asp Tyr Lys Ser Phe
    1040                1045                1050

Thr Glu Arg Ala Ser Gly Cys Lys Ser Lys Trp Ile Ala Cys Thr
1055                1060                1065

Asn Gly Glu Arg Ile Val Lys Tyr Arg Asn Ser Asp Lys Asn Asn
    1070                1075                1080

Ser Phe Asp Asp Lys Thr Val Ile Leu Thr Asp Glu Tyr Arg Ser
1085                1090                1095

Leu Phe Asp Lys Tyr Leu Gln Asn Tyr Ile Asp Glu Asp Asp Leu
    1100                1105                1110

Lys Asp Gln Ile Leu Gln Ile Asp Ser Ala Asp Phe Tyr Lys Asn
1115                1120                1125

Leu Ile Lys Leu Phe Gln Leu Thr Leu Gln Met Arg Asn Ser Ser
    1130                1135                1140

Ser Asp Gly Lys Arg Asp Tyr Ile Ile Ser Pro Val Lys Asn Tyr
1145                1150                1155

Arg Glu Glu Phe Phe Cys Ser Glu Phe Ser Asp Asp Thr Phe Pro
    1160                1165                1170

Arg Asp Ala Asp Ala Asn Gly Ala Tyr Asn Ile Ala Arg Lys Gly
1175                1180                1185

Leu Trp Val Ile Lys Gln Ile Arg Glu Thr Lys Ser Gly Thr Lys
    1190                1195                1200

Ile Asn Leu Ala Met Ser Asn Ser Glu Trp Leu Glu Tyr Ala Gln
1205                1210                1215

Cys Asn Leu Leu
    1220

<210> SEQ ID NO 8
<211> LENGTH: 1206
<212> TYPE: PRT
<213> ORGANISM: Butyrivibrio sp.

<400> SEQUENCE: 8

Met Tyr Tyr Gln Asn Leu Thr Lys Lys Tyr Pro Val Ser Lys Thr Ile
1               5                   10                  15

Arg Asn Glu Leu Ile Pro Ile Gly Lys Thr Leu Glu Asn Ile Arg Lys
            20                  25                  30

Asn Asn Ile Leu Glu Ser Asp Val Lys Arg Lys Gln Asp Tyr Glu His
        35                  40                  45

Val Lys Gly Ile Met Asp Glu Tyr His Lys Gln Leu Ile Asn Glu Ala
    50                  55                  60

Leu Asp Asn Tyr Met Leu Pro Ser Leu Asn Gln Ala Ala Glu Ile Tyr
65                  70                  75                  80

Leu Lys Lys His Val Asp Val Glu Asp Arg Glu Glu Phe Lys Lys Thr
                85                  90                  95

Gln Asp Leu Leu Arg Arg Glu Val Thr Gly Arg Leu Lys Glu His Glu
            100                 105                 110

Asn Tyr Thr Lys Ile Gly Lys Lys Asp Ile Leu Asp Leu Leu Glu Lys
        115                 120                 125

Leu Pro Ser Ile Ser Glu Glu Asp Tyr Asn Ala Leu Glu Ser Phe Arg
    130                 135                 140

Asn Phe Tyr Thr Tyr Phe Thr Ser Tyr Asn Lys Val Arg Glu Asn Leu
145                 150                 155                 160

Tyr Ser Asp Glu Glu Lys Ser Ser Thr Val Ala Tyr Arg Leu Ile Asn
```

```
                    165                 170                 175
Glu Asn Leu Pro Lys Phe Leu Asp Asn Ile Lys Ser Tyr Ala Phe Val
                180                 185                 190

Lys Ala Ala Gly Val Leu Ala Asp Cys Ile Glu Glu Glu Glu Gln Asp
            195                 200                 205

Ala Leu Phe Met Val Glu Thr Phe Asn Met Thr Leu Thr Gln Glu Gly
        210                 215                 220

Ile Asp Met Tyr Asn Tyr Gln Ile Gly Lys Val Asn Ser Ala Ile Asn
225                 230                 235                 240

Leu Tyr Asn Gln Lys Asn His Lys Val Glu Glu Phe Lys Lys Ile Pro
                245                 250                 255

Lys Met Lys Val Leu Tyr Lys Gln Ile Leu Ser Asp Arg Glu Glu Val
            260                 265                 270

Phe Ile Gly Glu Phe Lys Asp Asp Glu Thr Leu Leu Ser Ser Ile Gly
        275                 280                 285

Ala Tyr Gly Asn Val Leu Met Thr Tyr Leu Lys Ser Glu Lys Ile Asn
    290                 295                 300

Ile Phe Phe Asp Ala Leu Arg Glu Ser Glu Gly Lys Asn Val Tyr Val
305                 310                 315                 320

Lys Asn Asp Leu Ser Lys Thr Thr Met Ser Asn Ile Val Phe Gly Ser
                325                 330                 335

Trp Ser Ala Phe Asp Glu Leu Leu Asn Gln Glu Tyr Asp Leu Ala Asn
            340                 345                 350

Glu Asn Lys Lys Lys Asp Asp Lys Tyr Phe Glu Lys Arg Gln Lys Glu
        355                 360                 365

Leu Lys Lys Asn Lys Ser Tyr Thr Leu Glu Gln Met Ser Asn Leu Ser
    370                 375                 380

Lys Glu Asp Ile Ser Pro Ile Glu Asn Tyr Ile Glu Arg Ile Ser Glu
385                 390                 395                 400

Asp Ile Glu Lys Ile Cys Ile Tyr Asn Gly Glu Phe Glu Lys Ile Val
                405                 410                 415

Val Asn Glu His Asp Ser Ser Arg Lys Leu Ser Lys Asn Ile Lys Ala
            420                 425                 430

Val Lys Val Ile Lys Asp Tyr Leu Asp Ser Ile Lys Glu Leu Glu His
        435                 440                 445

Asp Ile Lys Leu Ile Asn Gly Ser Gly Gln Glu Leu Glu Lys Asn Leu
    450                 455                 460

Val Val Tyr Val Gly Gln Glu Ala Leu Glu Gln Leu Arg Pro Val
465                 470                 475                 480

Asp Ser Leu Tyr Asn Leu Thr Arg Asn Tyr Leu Thr Lys Lys Pro Phe
                485                 490                 495

Ser Thr Glu Lys Val Lys Leu Asn Phe Asn Lys Ser Thr Leu Leu Asn
            500                 505                 510

Gly Trp Asp Lys Asn Lys Glu Thr Asp Asn Leu Gly Ile Leu Phe Phe
        515                 520                 525

Lys Asp Gly Lys Tyr Tyr Leu Gly Ile Met Asn Thr Ala Asn Lys
    530                 535                 540

Ala Phe Val Asn Pro Pro Ala Ala Lys Thr Glu Asn Val Phe Lys Lys
545                 550                 555                 560

Val Asp Tyr Lys Leu Leu Pro Gly Ser Asn Lys Met Leu Pro Lys Val
                565                 570                 575

Phe Phe Ala Lys Ser Asn Ile Gly Tyr Tyr Asn Pro Ser Thr Glu Leu
            580                 585                 590
```

```
Tyr Ser Asn Tyr Lys Lys Gly Thr His Lys Gly Pro Ser Phe Ser
    595                 600                 605

Ile Asp Asp Cys His Asn Leu Ile Asp Phe Phe Lys Glu Ser Ile Lys
610                 615                 620

Lys His Glu Asp Trp Ser Lys Phe Gly Phe Glu Phe Ser Asp Thr Ala
625                 630                 635                 640

Asp Tyr Arg Asp Ile Ser Glu Phe Tyr Arg Glu Val Glu Lys Gln Gly
                645                 650                 655

Tyr Lys Leu Thr Phe Thr Asp Ile Asp Glu Ser Tyr Ile Asn Asp Leu
            660                 665                 670

Ile Glu Lys Asn Glu Leu Tyr Leu Phe Gln Ile Tyr Asn Lys Asp Phe
        675                 680                 685

Ser Glu Tyr Ser Lys Gly Lys Leu Asn Leu His Thr Leu Tyr Phe Met
    690                 695                 700

Met Leu Phe Asp Gln Arg Asn Leu Asp Asn Val Val Tyr Lys Leu Asn
705                 710                 715                 720

Gly Glu Ala Glu Val Phe Tyr Arg Pro Ala Ser Ile Ala Glu Asn Glu
                725                 730                 735

Leu Val Ile His Lys Ala Gly Glu Gly Ile Lys Asn Lys Asn Pro Asn
            740                 745                 750

Arg Ala Lys Val Lys Glu Thr Thr Phe Ser Tyr Asp Ile Val Lys
        755                 760                 765

Asp Lys Arg Tyr Ser Lys Tyr Lys Phe Thr Leu His Ile Pro Ile Thr
    770                 775                 780

Met Asn Phe Gly Val Asp Glu Val Arg Arg Phe Asn Asp Val Ile Asn
785                 790                 795                 800

Asn Ala Leu Arg Thr Asp Asp Asn Val Asn Val Ile Gly Ile Asp Arg
                805                 810                 815

Gly Glu Arg Asn Leu Leu Tyr Val Val Ile Asn Ser Glu Gly Lys
            820                 825                 830

Ile Leu Glu Gln Ile Ser Leu Asn Ser Ile Ile Asn Lys Glu Tyr Asp
        835                 840                 845

Ile Glu Thr Asn Tyr His Ala Leu Leu Asp Glu Arg Glu Asp Asp Arg
    850                 855                 860

Asn Lys Ala Arg Lys Asp Trp Asn Thr Ile Glu Asn Ile Lys Glu Leu
865                 870                 875                 880

Lys Thr Gly Tyr Leu Ser Gln Val Val Asn Val Val Ala Lys Leu Val
                885                 890                 895

Leu Lys Tyr Asn Ala Ile Ile Cys Leu Glu Asp Leu Asn Phe Gly Phe
            900                 905                 910

Lys Arg Gly Arg Gln Lys Val Glu Lys Gln Val Tyr Gln Lys Phe Glu
        915                 920                 925

Lys Met Leu Ile Glu Lys Leu Asn Tyr Leu Val Ile Asp Lys Ser Arg
    930                 935                 940

Glu Gln Val Ser Pro Glu Lys Met Gly Gly Ala Leu Asn Ala Leu Gln
945                 950                 955                 960

Leu Thr Ser Lys Phe Lys Ser Phe Ala Glu Leu Gly Lys Gln Ser Gly
                965                 970                 975

Ile Ile Tyr Tyr Val Pro Ala Tyr Leu Thr Ser Lys Ile Asp Pro Thr
            980                 985                 990

Thr Gly Phe Val Asn Leu Phe Tyr Ile Lys Tyr Glu Asn Ile Glu Lys
        995                 1000                1005
```

```
Ala Lys Gln Phe Phe Asp Gly Phe Asp Phe Ile Arg Phe Asn Lys
    1010                1015                1020

Lys Asp Asp Met Phe Glu Phe Ser Phe Asp Tyr Lys Ser Phe Thr
    1025                1030                1035

Gln Lys Ala Cys Gly Ile Arg Ser Lys Trp Ile Val Tyr Thr Asn
    1040                1045                1050

Gly Glu Arg Ile Ile Lys Tyr Pro Asn Pro Glu Lys Asn Asn Leu
    1055                1060                1065

Phe Asp Glu Lys Val Ile Asn Val Thr Asp Glu Ile Lys Gly Leu
    1070                1075                1080

Phe Lys Gln Tyr Arg Ile Pro Tyr Glu Asn Gly Glu Asp Ile Lys
    1085                1090                1095

Glu Ile Ile Ile Ser Lys Ala Glu Ala Asp Phe Tyr Lys Arg Leu
    1100                1105                1110

Phe Arg Leu Leu His Gln Thr Leu Gln Met Arg Asn Ser Thr Ser
    1115                1120                1125

Asp Gly Thr Arg Asp Tyr Ile Ile Ser Pro Val Lys Asn Asp Arg
    1130                1135                1140

Gly Glu Phe Phe Cys Ser Glu Phe Ser Glu Gly Thr Met Pro Lys
    1145                1150                1155

Asp Ala Asp Ala Asn Gly Ala Tyr Asn Ile Ala Arg Lys Gly Leu
    1160                1165                1170

Trp Val Leu Glu Gln Ile Arg Gln Lys Asp Glu Gly Glu Lys Val
    1175                1180                1185

Asn Leu Ser Met Thr Asn Ala Glu Trp Leu Lys Tyr Ala Gln Leu
    1190                1195                1200

His Leu Leu
    1205

<210> SEQ ID NO 9
<211> LENGTH: 1154
<212> TYPE: PRT
<213> ORGANISM: Proteocatella sphenisci

<400> SEQUENCE: 9

Met Glu Asn Phe Lys Asn Leu Tyr Pro Ile Asn Lys Thr Leu Arg Phe
1               5                   10                  15

Glu Leu Arg Pro Tyr Gly Lys Thr Leu Glu Asn Phe Lys Lys Ser Gly
                20                  25                  30

Leu Leu Glu Lys Asp Ala Phe Lys Ala Asn Ser Arg Arg Ser Met Gln
            35                  40                  45

Ala Ile Ile Asp Glu Lys Phe Lys Glu Thr Ile Glu Glu Arg Leu Lys
        50                  55                  60

Tyr Thr Glu Phe Ser Glu Cys Asp Leu Gly Asn Met Thr Ser Lys Asp
65                  70                  75                  80

Lys Lys Ile Thr Asp Lys Ala Ala Thr Asn Leu Lys Lys Gln Val Ile
                85                  90                  95

Leu Ser Phe Asp Asp Glu Ile Phe Asn Asn Tyr Leu Lys Pro Asp Lys
                100                 105                 110

Asn Ile Asp Ala Leu Phe Lys Asn Asp Pro Ser Asn Pro Val Ile Ser
            115                 120                 125

Thr Phe Lys Gly Phe Thr Thr Tyr Phe Val Asn Phe Phe Glu Ile Arg
        130                 135                 140

Lys His Ile Phe Lys Gly Glu Ser Ser Gly Ser Met Ala Tyr Arg Ile
145                 150                 155                 160
```

```
Ile Asp Glu Asn Leu Thr Thr Tyr Leu Asn Asn Ile Glu Lys Ile Lys
            165                 170                 175

Lys Leu Pro Glu Glu Leu Lys Ser Gln Leu Glu Gly Ile Asp Gln Ile
            180                 185                 190

Asp Lys Leu Asn Asn Tyr Asn Glu Phe Ile Thr Gln Ser Gly Ile Thr
            195                 200                 205

His Tyr Asn Glu Ile Ile Gly Gly Ile Ser Lys Ser Glu Asn Val Lys
            210                 215                 220

Ile Gln Gly Ile Asn Glu Gly Ile Asn Leu Tyr Cys Gln Lys Asn Lys
225                 230                 235                 240

Val Lys Leu Pro Arg Leu Thr Pro Leu Tyr Lys Met Ile Leu Ser Asp
            245                 250                 255

Arg Val Ser Asn Ser Phe Val Leu Asp Thr Ile Glu Asn Asp Thr Glu
            260                 265                 270

Leu Ile Glu Met Ile Ser Asp Leu Ile Asn Lys Thr Glu Ile Ser Gln
            275                 280                 285

Asp Val Ile Met Ser Asp Ile Gln Asn Ile Phe Ile Lys Tyr Lys Gln
            290                 295                 300

Leu Gly Asn Leu Pro Gly Ile Ser Tyr Ser Ser Ile Val Asn Ala Ile
305                 310                 315                 320

Cys Ser Asp Tyr Asp Asn Asn Phe Gly Asp Gly Lys Arg Lys Lys Ser
            325                 330                 335

Tyr Glu Asn Asp Arg Lys Lys His Leu Glu Thr Asn Val Tyr Ser Ile
            340                 345                 350

Asn Tyr Ile Ser Glu Leu Leu Thr Asp Thr Asp Val Ser Ser Asn Ile
            355                 360                 365

Lys Met Arg Tyr Lys Glu Leu Glu Gln Asn Tyr Gln Val Cys Lys Glu
            370                 375                 380

Asn Phe Asn Ala Thr Asn Trp Met Asn Ile Lys Asn Ile Lys Gln Ser
385                 390                 395                 400

Glu Lys Thr Asn Leu Ile Lys Asp Leu Leu Asp Ile Leu Lys Ser Ile
            405                 410                 415

Gln Arg Phe Tyr Asp Leu Phe Asp Ile Val Asp Glu Lys Asn Pro
            420                 425                 430

Ser Ala Glu Phe Tyr Thr Trp Leu Ser Lys Asn Ala Glu Lys Leu Asp
            435                 440                 445

Phe Glu Phe Asn Ser Val Tyr Asn Lys Ser Arg Asn Tyr Leu Thr Arg
450                 455                 460

Lys Gln Tyr Ser Asp Lys Lys Ile Lys Leu Asn Phe Asp Ser Pro Thr
465                 470                 475                 480

Leu Ala Lys Gly Trp Asp Ala Asn Lys Glu Ile Asp Asn Ser Thr Ile
            485                 490                 495

Ile Met Arg Lys Phe Asn Asn Asp Arg Gly Asp Tyr Asp Tyr Phe Leu
            500                 505                 510

Gly Ile Trp Asn Lys Ser Thr Pro Ala Asn Glu Lys Ile Ile Pro Leu
            515                 520                 525

Glu Asp Asn Gly Leu Phe Glu Lys Met Gln Tyr Lys Leu Tyr Pro Asp
            530                 535                 540

Pro Ser Lys Met Leu Pro Lys Gln Phe Leu Ser Lys Ile Trp Lys Ala
545                 550                 555                 560

Lys His Pro Thr Thr Pro Glu Phe Asp Lys Lys Tyr Lys Glu Gly Arg
            565                 570                 575
```

```
His Lys Lys Gly Pro Asp Phe Glu Lys Glu Phe Leu His Glu Leu Ile
                580                 585                 590

Asp Cys Phe Lys His Gly Leu Val Asn His Asp Glu Lys Tyr Gln Asp
            595                 600                 605

Val Phe Gly Phe Asn Leu Arg Asn Thr Glu Asp Tyr Asn Ser Tyr Thr
        610                 615                 620

Glu Phe Leu Glu Asp Val Glu Arg Cys Asn Tyr Asn Leu Ser Phe Asn
625                 630                 635                 640

Lys Ile Ala Asp Thr Ser Asn Leu Ile Asn Asp Gly Lys Leu Tyr Val
                645                 650                 655

Phe Gln Ile Trp Ser Lys Asp Phe Ser Ile Asp Ser Lys Gly Thr Lys
            660                 665                 670

Asn Leu Asn Thr Ile Tyr Phe Glu Ser Leu Phe Ser Glu Glu Asn Met
        675                 680                 685

Ile Glu Lys Met Phe Lys Leu Ser Gly Glu Ala Glu Ile Phe Tyr Arg
690                 695                 700

Pro Ala Ser Leu Asn Tyr Cys Glu Asp Ile Ile Lys Lys Gly His His
705                 710                 715                 720

His Ala Glu Leu Lys Asp Lys Phe Asp Tyr Pro Ile Ile Lys Asp Lys
                725                 730                 735

Arg Tyr Ser Gln Asp Lys Phe Phe His Val Pro Met Val Ile Asn
            740                 745                 750

Tyr Lys Ser Glu Lys Leu Asn Ser Lys Ser Leu Asn Asn Arg Thr Asn
        755                 760                 765

Glu Asn Leu Gly Gln Phe Thr His Ile Ile Gly Ile Asp Arg Gly Glu
770                 775                 780

Arg His Leu Ile Tyr Leu Thr Val Val Asp Val Ser Thr Gly Glu Ile
785                 790                 795                 800

Val Glu Gln Lys His Leu Asp Glu Ile Ile Asn Thr Asp Thr Lys Gly
                805                 810                 815

Val Glu His Lys Thr His Tyr Leu Asn Lys Leu Glu Glu Lys Ser Lys
            820                 825                 830

Thr Arg Asp Asn Glu Arg Lys Ser Trp Glu Ala Ile Glu Thr Ile Lys
        835                 840                 845

Glu Leu Lys Glu Gly Tyr Ile Ser His Val Ile Asn Glu Ile Gln Lys
850                 855                 860

Leu Gln Glu Lys Tyr Asn Ala Leu Ile Val Met Glu Asn Leu Asn Tyr
865                 870                 875                 880

Gly Phe Lys Asn Ser Arg Ile Lys Val Glu Lys Gln Val Tyr Gln Lys
                885                 890                 895

Phe Glu Thr Ala Leu Ile Lys Lys Phe Asn Tyr Ile Ile Asp Lys Lys
            900                 905                 910

Asp Pro Glu Thr Tyr Ile His Gly Tyr Gln Leu Thr Asn Pro Ile Thr
        915                 920                 925

Thr Leu Asp Lys Ile Gly Asn Gln Ser Gly Ile Val Leu Tyr Ile Pro
930                 935                 940

Ala Trp Asn Thr Ser Lys Ile Asp Pro Val Thr Gly Phe Val Asn Leu
945                 950                 955                 960

Leu Tyr Ala Asp Asp Leu Lys Tyr Lys Asn Gln Glu Gln Ala Lys Ser
                965                 970                 975

Phe Ile Gln Lys Ile Asp Asn Ile Tyr Phe Glu Asn Gly Glu Phe Lys
            980                 985                 990

Phe Asp Ile Asp Phe Ser Lys Trp  Asn Asn Arg Tyr Ser  Ile Ser Lys
```

```
                995              1000                1005
Thr Lys Trp Thr Leu Thr Ser Tyr Gly Thr Arg Ile Gln Thr Phe
   1010             1015                1020

Arg Asn Pro Gln Lys Asn Asn Lys Trp Asp Ser Ala Glu Tyr Asp
   1025             1030                1035

Leu Thr Glu Glu Phe Lys Leu Ile Leu Asn Ile Asp Gly Thr Leu
   1040             1045                1050

Lys Ser Gln Asp Val Glu Thr Tyr Lys Lys Phe Met Ser Leu Phe
   1055             1060                1065

Lys Leu Met Leu Gln Leu Arg Asn Ser Val Thr Gly Thr Asp Ile
   1070             1075                1080

Asp Tyr Met Ile Ser Pro Val Thr Asp Lys Thr Gly Thr His Phe
   1085             1090                1095

Asp Ser Arg Glu Asn Ile Lys Asn Leu Pro Ala Asp Ala Asp Ala
   1100             1105                1110

Asn Gly Ala Tyr Asn Ile Ala Arg Lys Gly Ile Met Ala Ile Glu
   1115             1120                1125

Asn Ile Met Asn Gly Ile Ser Asp Pro Leu Lys Ile Ser Asn Glu
   1130             1135                1140

Asp Tyr Leu Lys Tyr Ile Gln Asn Gln Gln Glu
   1145             1150
```

<210> SEQ ID NO 10
<211> LENGTH: 1214
<212> TYPE: PRT
<213> ORGANISM: Candidatus Dojkabacteria

<400> SEQUENCE: 10

```
Met Lys Asn Val Phe Gly Gly Phe Thr Asn Leu Tyr Ser Leu Thr Lys
1               5                   10                  15

Thr Leu Arg Phe Glu Leu Lys Pro Thr Ser Lys Thr Gln Lys Leu Met
                20                  25                  30

Lys Arg Asn Asn Val Ile Gln Thr Asp Glu Glu Ile Asp Lys Leu Tyr
            35                  40                  45

His Asp Glu Met Lys Pro Ile Leu Asp Glu Ile His Arg Arg Phe Ile
        50                  55                  60

Asn Asp Ala Leu Ala Gln Lys Ile Phe Ile Ser Ala Ser Leu Asp Asn
65                  70                  75                  80

Phe Leu Lys Val Val Lys Asn Tyr Lys Val Glu Ser Ala Lys Lys Asn
                85                  90                  95

Ile Lys Gln Asn Gln Val Lys Leu Leu Gln Lys Glu Ile Thr Ile Lys
            100                 105                 110

Thr Leu Gly Leu Arg Arg Glu Val Val Ser Gly Phe Ile Thr Val Ser
        115                 120                 125

Lys Lys Trp Lys Asp Lys Tyr Val Gly Leu Gly Ile Lys Leu Lys Gly
    130                 135                 140

Asp Gly Tyr Lys Val Leu Thr Glu Gln Ala Val Leu Asp Ile Leu Lys
145                 150                 155                 160

Ile Glu Phe Pro Asn Lys Ala Lys Tyr Ile Asp Lys Phe Arg Gly Phe
                165                 170                 175

Trp Thr Tyr Phe Ser Gly Phe Asn Glu Asn Arg Lys Asn Tyr Tyr Ser
            180                 185                 190

Glu Glu Asp Lys Ala Thr Ser Ile Ala Asn Arg Ile Val Asn Glu Asn
        195                 200                 205
```

-continued

Leu Ser Arg Tyr Ile Asp Asn Ile Ile Ala Phe Glu Glu Ile Leu Gln
210                 215                 220

Lys Ile Pro Asn Leu Lys Lys Phe Lys Gln Asp Leu Asp Ile Thr Ser
225                 230                 235                 240

Tyr Asn Tyr Tyr Leu Asn Gln Ala Gly Ile Asp Lys Tyr Asn Lys Ile
            245                 250                 255

Ile Gly Gly Tyr Ile Val Asp Lys Asp Lys Lys Ile Gln Gly Ile Asn
            260                 265                 270

Glu Lys Val Asn Leu Tyr Thr Gln Gln Thr Lys Lys Lys Leu Pro Lys
        275                 280                 285

Leu Lys Phe Leu Phe Lys Gln Ile Gly Ser Glu Arg Lys Gly Phe Gly
        290                 295                 300

Ile Phe Glu Ile Lys Glu Gly Lys Glu Trp Glu Gln Leu Gly Asp Leu
305                 310                 315                 320

Phe Lys Leu Gln Arg Thr Lys Ile Asn Ser Asn Gly Arg Glu Lys Gly
                325                 330                 335

Leu Phe Asp Ser Leu Arg Thr Met Tyr Arg Glu Phe Phe Asp Glu Ile
            340                 345                 350

Lys Arg Asp Ser Asn Ser Gln Ala Arg Tyr Ser Leu Asp Lys Ile Tyr
            355                 360                 365

Phe Asn Lys Ala Ser Val Asn Thr Ile Ser Asn Ser Trp Phe Thr Asn
370                 375                 380

Trp Asn Lys Phe Ala Glu Leu Leu Asn Ile Lys Glu Asp Lys Lys Asn
385                 390                 395                 400

Gly Glu Lys Lys Ile Pro Glu Gln Ile Ser Ile Glu Asp Ile Lys Asp
                405                 410                 415

Ser Leu Ser Ile Ile Pro Lys Glu Asn Leu Glu Glu Leu Phe Lys Leu
            420                 425                 430

Thr Asn Arg Glu Lys His Asp Arg Thr Arg Phe Phe Gly Ser Asn Ala
            435                 440                 445

Trp Val Thr Phe Leu Asn Ile Trp Gln Asn Glu Ile Glu Glu Ser Phe
    450                 455                 460

Asn Lys Leu Glu Glu Lys Glu Lys Asp Phe Lys Lys Asn Ala Ala Ile
465                 470                 475                 480

Lys Phe Gln Lys Asn Asn Leu Val Gln Lys Asn Tyr Ile Lys Glu Val
                485                 490                 495

Cys Asp Arg Met Leu Ala Ile Glu Arg Met Ala Lys Tyr His Leu Pro
            500                 505                 510

Lys Asp Ser Asn Leu Ser Arg Glu Glu Asp Phe Tyr Trp Ile Ile Asp
            515                 520                 525

Asn Leu Ser Glu Gln Arg Glu Ile Tyr Lys Tyr Tyr Asn Ala Phe Arg
        530                 535                 540

Asn Tyr Ile Ser Lys Lys Pro Tyr Asn Lys Ser Lys Met Lys Leu Asn
545                 550                 555                 560

Phe Glu Asn Gly Asn Leu Leu Gly Gly Trp Ser Asp Gly Gln Glu Arg
            565                 570                 575

Asn Lys Ala Gly Val Ile Leu Arg Asn Gly Asn Lys Tyr Tyr Leu Gly
            580                 585                 590

Val Leu Ile Asn Arg Gly Ile Phe Arg Thr Asp Lys Ile Asn Asn Glu
            595                 600                 605

Ile Tyr Arg Thr Gly Ser Ser Lys Trp Glu Arg Leu Ile Leu Ser Asn
610                 615                 620

Leu Lys Phe Gln Thr Leu Ala Gly Lys Gly Phe Leu Gly Lys His Gly

-continued

```
            625                 630                 635                 640
Val Ser Tyr Gly Asn Met Asn Pro Glu Lys Ser Val Pro Ser Leu Gln
                645                 650                 655

Lys Phe Ile Arg Glu Asn Tyr Leu Lys Lys Tyr Pro Gln Leu Thr Glu
                660                 665                 670

Val Ser Asn Thr Lys Phe Leu Ser Lys Lys Asp Phe Asp Ala Ala Ile
                675                 680                 685

Lys Glu Ala Leu Lys Glu Cys Phe Thr Met Asn Phe Ile Asn Ile Ala
                690                 695                 700

Glu Asn Lys Leu Leu Glu Ala Glu Asp Lys Gly Asp Leu Tyr Leu Phe
705                 710                 715                 720

Glu Ile Thr Asn Lys Asp Phe Ser Gly Lys Ser Gly Lys Asp Asn
                725                 730                 735

Ile His Thr Ile Tyr Trp Lys Tyr Leu Phe Ser Glu Ser Asn Cys Lys
                740                 745                 750

Ser Pro Ile Ile Gly Leu Asn Gly Gly Ala Glu Ile Phe Phe Arg Glu
                755                 760                 765

Gly Gln Lys Asp Lys Leu His Thr Lys Leu Asp Lys Lys Gly Lys Lys
                770                 775                 780

Val Phe Asp Ala Lys Arg Tyr Ser Glu Asp Lys Leu Phe Phe His Val
785                 790                 795                 800

Ser Ile Thr Ile Asn Tyr Gly Lys Pro Lys Asn Ile Lys Phe Arg Asp
                805                 810                 815

Ile Ile Asn Gln Leu Ile Thr Ser Met Asn Val Asn Ile Ile Gly Ile
                820                 825                 830

Asp Arg Gly Glu Lys His Leu Leu Tyr Tyr Ser Val Ile Asp Ser Asn
                835                 840                 845

Gly Ile Ile Leu Lys Gln Gly Ser Leu Asn Lys Ile Arg Val Gly Asp
                850                 855                 860

Lys Glu Val Asp Phe Asn Lys Lys Leu Thr Glu Arg Ala Asn Glu Met
865                 870                 875                 880

Lys Lys Ala Arg Gln Ser Trp Glu Gln Ile Gly Asn Ile Lys Asn Phe
                885                 890                 895

Lys Glu Gly Tyr Leu Ser Gln Ala Ile His Glu Ile Tyr Gln Leu Met
                900                 905                 910

Ile Lys Tyr Asn Ala Ile Ile Val Leu Glu Asp Leu Asn Thr Glu Phe
                915                 920                 925

Lys Ala Lys Arg Leu Ser Lys Val Glu Lys Ser Val Tyr Lys Lys Phe
                930                 935                 940

Glu Leu Lys Leu Ala Arg Lys Leu Asn His Leu Ile Leu Lys Asp Arg
945                 950                 955                 960

Asn Thr Asn Glu Ile Gly Gly Val Leu Lys Ala Tyr Gln Leu Thr Pro
                965                 970                 975

Thr Ile Gly Gly Gly Asp Val Ser Lys Phe Glu Lys Ala Lys Gln Trp
                980                 985                 990

Gly Met Met Phe Tyr Val Arg Ala Asn Tyr Thr Ser Thr Thr Asp Pro
                995                 1000                1005

Val Thr Gly Trp Arg Lys His Leu Tyr Ile Ser Asn Phe Ser Asn
                1010                1015                1020

Asn Ser Val Ile Lys Ser Phe Asp Pro Thr Asn Arg Asp Thr
                1025                1030                1035

Gly Ile Glu Ile Phe Tyr Ser Gly Lys Tyr Arg Ser Trp Gly Phe
                1040                1045                1050
```

```
Arg Tyr Val Gln Lys Glu Thr Gly Lys Lys Trp Glu Leu Phe Ala
    1055                1060                1065

Thr Lys Glu Leu Glu Arg Phe Lys Tyr Asn Gln Thr Thr Lys Leu
    1070                1075                1080

Cys Glu Lys Ile Asn Leu Tyr Asp Lys Phe Glu Glu Leu Phe Lys
    1085                1090                1095

Gly Ile Asp Lys Ser Ala Asp Ile Tyr Ser Gln Leu Cys Asn Val
    1100                1105                1110

Leu Asp Phe Arg Trp Lys Ser Leu Val Tyr Leu Trp Asn Leu Leu
    1115                1120                1125

Asn Gln Ile Arg Asn Val Asp Lys Asn Ala Glu Gly Asn Lys Asn
    1130                1135                1140

Asp Phe Ile Gln Ser Pro Val Tyr Pro Phe Phe Asp Ser Arg Lys
    1145                1150                1155

Thr Asp Gly Lys Thr Glu Pro Ile Asn Gly Asp Ala Asn Gly Ala
    1160                1165                1170

Leu Asn Ile Ala Arg Lys Gly Leu Met Leu Val Glu Arg Ile Lys
    1175                1180                1185

Asn Asn Pro Glu Lys Tyr Glu Gln Leu Ile Arg Asp Thr Glu Trp
    1190                1195                1200

Asp Ala Trp Ile Gln Asn Phe Asn Lys Val Asn
    1205                1210

<210> SEQ ID NO 11
<211> LENGTH: 1215
<212> TYPE: PRT
<213> ORGANISM: Pseudobutyrivibrio xylanivorans

<400> SEQUENCE: 11

Met Ile Ile Gly Arg Asp Phe Asn Met Tyr Tyr Gln Asn Leu Thr Lys
1               5                   10                  15

Met Tyr Pro Ile Ser Lys Thr Leu Arg Asn Glu Leu Ile Pro Val Gly
                20                  25                  30

Lys Thr Leu Glu Asn Ile Arg Lys Asn Gly Ile Leu Glu Ala Asp Ile
            35                  40                  45

Gln Arg Lys Ala Asp Tyr Glu His Val Lys Lys Leu Met Asp Asn Tyr
        50                  55                  60

His Lys Gln Leu Ile Asn Glu Ala Leu Gln Gly Val His Leu Ser Asp
65                  70                  75                  80

Leu Ser Asp Ala Tyr Asp Leu Tyr Phe Asn Leu Ser Lys Glu Lys Asn
                85                  90                  95

Ser Val Asp Ala Phe Ser Lys Cys Gln Asp Lys Leu Arg Lys Glu Ile
            100                 105                 110

Val Ser Phe Leu Lys Asn His Glu Asn Phe Pro Lys Ile Gly Asn Lys
        115                 120                 125

Glu Ile Ile Lys Leu Ile Gln Ser Leu Asn Asp Asn Asp Ala Asp Asn
    130                 135                 140

Asn Ala Leu Asp Ser Phe Ser Asn Phe Tyr Thr Tyr Phe Ser Ser Tyr
145                 150                 155                 160

Asn Glu Val Arg Lys Asn Leu Tyr Ser Asp Glu Lys Ser Ser Thr
                165                 170                 175

Val Ala Tyr Arg Leu Ile Asn Glu Asn Leu Pro Lys Ser Leu Asp Asn
            180                 185                 190

Ile Lys Ala Tyr Ala Ile Ala Lys Lys Ala Gly Val Arg Ala Glu Gly
```

```
              195                 200                 205
Leu Ser Glu Glu Glu Gln Asp Cys Leu Phe Ile Ile Glu Thr Phe Glu
    210                 215                 220

Arg Thr Leu Thr Gln Asp Gly Ile Asp Asn Tyr Asn Ala Asp Ile Gly
225                 230                 235                 240

Lys Leu Asn Thr Ala Ile Asn Leu Tyr Asn Gln Gln Asn Lys Lys Gln
                245                 250                 255

Glu Gly Phe Arg Lys Val Pro Gln Met Lys Cys Leu Tyr Lys Gln Ile
            260                 265                 270

Leu Ser Asp Arg Glu Glu Ala Phe Ile Asp Glu Phe Ser Asp Asp Glu
        275                 280                 285

Asp Leu Ile Thr Asn Ile Glu Ser Phe Ala Glu Asn Met Asn Val Phe
    290                 295                 300

Leu Asn Ser Glu Ile Ile Thr Asp Phe Lys Asn Ala Leu Val Glu Ser
305                 310                 315                 320

Asp Gly Ser Leu Val Tyr Ile Lys Asn Asp Val Ser Lys Thr Leu Phe
                325                 330                 335

Ser Asn Ile Val Phe Gly Ser Trp Asn Ala Ile Asp Glu Lys Leu Ser
            340                 345                 350

Asp Glu Tyr Asp Leu Ala Asn Ser Lys Lys Lys Asp Glu Lys Tyr
        355                 360                 365

Tyr Glu Lys Arg Gln Lys Glu Leu Lys Lys Asn Lys Ser Tyr Asp Leu
    370                 375                 380

Glu Thr Ile Ile Gly Leu Phe Asp Asp Ser Ile Asp Val Ile Gly Lys
385                 390                 395                 400

Tyr Ile Glu Lys Leu Glu Ser Asp Ile Thr Ala Ile Ala Glu Ala Lys
                405                 410                 415

Asn Asp Phe Asp Glu Ile Val Leu Arg Lys His Asp Lys Asn Lys Ser
            420                 425                 430

Leu Arg Lys Asn Thr Asn Ala Val Glu Ala Ile Lys Ser Tyr Leu Asp
        435                 440                 445

Thr Val Lys Asp Phe Glu Arg Asp Ile Lys Leu Ile Asn Gly Ser Gly
    450                 455                 460

Gln Glu Val Glu Lys Asn Leu Val Val Tyr Ala Glu Gln Glu Asn Ile
465                 470                 475                 480

Leu Ala Glu Ile Lys Asn Val Asp Ser Leu Tyr Asn Met Ser Arg Asn
                485                 490                 495

Tyr Leu Thr Gln Lys Pro Phe Ser Thr Glu Lys Phe Lys Leu Asn Phe
            500                 505                 510

Glu Asn Pro Thr Leu Leu Asn Gly Trp Asp Arg Asn Lys Glu Lys Asp
        515                 520                 525

Tyr Leu Gly Ile Leu Phe Glu Lys Glu Gly Met Tyr Tyr Leu Gly Ile
    530                 535                 540

Ile Asn Asn Asn His Arg Lys Ile Phe Glu Asn Glu Lys Leu Cys Thr
545                 550                 555                 560

Gly Lys Glu Ser Cys Phe Asn Lys Ile Val Tyr Lys Gln Ile Ser Asn
                565                 570                 575

Ala Ala Lys Tyr Leu Ser Ser Lys Gln Ile Asn Pro Gln Asn Pro Pro
            580                 585                 590

Lys Glu Ile Ala Glu Ile Leu Leu Lys Arg Lys Ala Asp Ser Ser Ser
        595                 600                 605

Leu Ser Arg Lys Glu Thr Glu Leu Phe Ile Asp Tyr Leu Lys Asp Asp
    610                 615                 620
```

-continued

Phe Leu Val Asn Tyr Pro Met Ile Ile Asn Ser Asp Gly Glu Asn Phe
625                 630                 635                 640

Phe Asn Phe His Phe Lys Gln Ala Lys Asp Tyr Gly Ser Leu Gln Glu
            645                 650                 655

Phe Phe Lys Glu Val Glu His Gln Ala Tyr Ser Leu Lys Thr Arg Pro
        660                 665                 670

Ile Asp Asp Ser Tyr Ile Tyr Arg Met Ile Asp Glu Gly Lys Leu Tyr
    675                 680                 685

Leu Phe Gln Ile His Asn Lys Asp Phe Ser Pro Tyr Ser Lys Gly Asn
690                 695                 700

Leu Asn Leu His Thr Ile Tyr Leu Gln Met Leu Phe Asp Gln Arg Asn
705                 710                 715                 720

Leu Asn Asn Val Val Tyr Lys Leu Asn Gly Glu Ala Glu Val Phe Tyr
            725                 730                 735

Arg Pro Ala Ser Ile Asn Asp Glu Val Ile Ile His Lys Ala Gly
            740                 745                 750

Glu Glu Ile Lys Asn Lys Asn Ser Lys Arg Ala Val Asp Lys Pro Thr
            755                 760                 765

Ser Lys Phe Gly Tyr Asp Ile Ile Lys Asp Arg Tyr Ser Lys Asp
770                 775                 780

Lys Phe Met Leu His Ile Pro Val Thr Met Asn Phe Gly Val Asp Glu
785                 790                 795                 800

Thr Arg Arg Phe Asn Asp Val Val Asn Asp Ala Leu Arg Asn Asp Glu
                805                 810                 815

Lys Val Arg Val Ile Gly Ile Asp Arg Gly Glu Arg Asn Leu Leu Tyr
                820                 825                 830

Val Val Val Val Asp Thr Asp Gly Thr Ile Leu Glu Gln Ile Ser Leu
                835                 840                 845

Asn Ser Ile Ile Asn Asn Glu Tyr Ser Ile Glu Thr Asp Tyr His Lys
850                 855                 860

Leu Leu Asp Glu Lys Glu Gly Asp Arg Asp Arg Ala Arg Lys Asn Trp
865                 870                 875                 880

Thr Thr Ile Glu Asn Ile Lys Glu Leu Lys Glu Gly Tyr Leu Ser Gln
                885                 890                 895

Val Val Asn Val Ile Ala Lys Leu Val Leu Lys Tyr Asn Ala Ile Ile
        900                 905                 910

Cys Leu Glu Asp Leu Asn Phe Gly Phe Lys Arg Gly Arg Gln Lys Val
    915                 920                 925

Glu Lys Gln Val Tyr Gln Lys Phe Glu Lys Met Leu Ile Asp Lys Leu
930                 935                 940

Asn Tyr Leu Val Ile Asp Lys Ser Arg Lys Gln Glu Lys Pro Glu Glu
945                 950                 955                 960

Phe Gly Gly Ala Leu Asn Ala Leu Gln Leu Thr Ser Lys Phe Thr Ser
            965                 970                 975

Phe Lys Asp Met Gly Lys Gln Thr Gly Ile Ile Tyr Tyr Val Pro Ala
            980                 985                 990

Tyr Leu Thr Ser Lys Ile Asp Pro Thr Thr Gly Phe Ala Asn Leu Phe
        995                 1000                1005

Tyr Val Lys Tyr Glu Asn Val Glu Lys Ala Lys Glu Phe Phe Ser
    1010                1015                1020

Arg Phe Asp Ser Ile Ser Tyr Asn Asn Glu Ser Gly Tyr Phe Glu
    1025                1030                1035

-continued

```
Phe Ala Phe Asp Tyr Lys Lys Phe Thr Asp Arg Ala Cys Gly Ala
    1040                1045                1050

Arg Ser Gln Trp Thr Val Cys Thr Tyr Gly Glu Arg Ile Ile Lys
    1055                1060                1065

Tyr Arg Asn Ala Asp Lys Asn Asn Ser Phe Asp Lys Thr Ile
    1070                1075                1080

Val Leu Ser Glu Glu Phe Lys Glu Leu Phe Ser Ile Tyr Gly Ile
    1085                1090                1095

Ser Tyr Glu Asp Gly Ala Glu Leu Lys Asn Lys Ile Met Ser Val
    1100                1105                1110

Asp Glu Ala Asp Phe Phe Arg Cys Leu Thr Gly Leu Leu Gln Lys
    1115                1120                1125

Thr Leu Gln Met Arg Asn Ser Ser Asn Asp Gly Thr Arg Asp Tyr
    1130                1135                1140

Ile Ile Ser Pro Ile Met Asn Asp Arg Gly Glu Phe Phe Asn Ser
    1145                1150                1155

Glu Ala Cys Asp Ala Ser Lys Pro Lys Asp Ala Asp Ala Asn Gly
    1160                1165                1170

Ala Phe Asn Ile Ala Arg Lys Gly Leu Trp Val Leu Glu Gln Ile
    1175                1180                1185

Arg Asn Thr Pro Ser Gly Asp Lys Leu Asn Leu Ala Met Ser Asn
    1190                1195                1200

Ala Glu Trp Leu Glu Tyr Ala Gln Arg Asn Gln Ile
    1205                1210                1215

<210> SEQ ID NO 12
<211> LENGTH: 1213
<212> TYPE: PRT
<213> ORGANISM: Pseudobutyrivibrio ruminis

<400> SEQUENCE: 12

Met Ile Ile Gly Arg Asp Phe Asn Met Tyr Tyr Gln Asn Leu Thr Lys
1               5                   10                  15

Met Tyr Pro Ile Ser Lys Thr Leu Arg Asn Glu Leu Ile Pro Val Gly
                20                  25                  30

Lys Thr Leu Glu Asn Ile Arg Lys Asn Gly Ile Leu Glu Ala Asp Ile
            35                  40                  45

Gln Arg Lys Ala Asp Tyr Glu His Val Lys Lys Leu Met Asp Asn Tyr
        50                  55                  60

His Lys Gln Leu Ile Asn Glu Ala Leu Gln Gly Val His Leu Ser Asp
65                  70                  75                  80

Leu Ser Asp Ala Tyr Asp Leu Tyr Phe Asn Leu Ser Lys Glu Lys Asn
                85                  90                  95

Ser Val Asp Ala Phe Ser Lys Cys Gln Asp Lys Leu Arg Lys Glu Ile
            100                 105                 110

Val Ser Leu Leu Lys Asn His Glu Asn Phe Pro Lys Ile Gly Asn Lys
        115                 120                 125

Glu Ile Ile Lys Leu Leu Gln Ser Leu Tyr Asp Asn Asp Thr Asp Tyr
    130                 135                 140

Lys Ala Leu Asp Ser Phe Ser Asn Phe Tyr Thr Tyr Phe Ser Ser Tyr
145                 150                 155                 160

Asn Glu Val Arg Lys Asn Leu Tyr Ser Asp Glu Glu Lys Ser Ser Thr
                165                 170                 175

Val Ala Tyr Arg Leu Ile Asn Glu Asn Leu Pro Lys Phe Leu Asp Asn
            180                 185                 190
```

```
Ile Lys Ala Tyr Ala Ile Ala Lys Lys Ala Gly Val Arg Ala Glu Gly
        195                 200                 205

Leu Ser Glu Glu Asp Gln Asp Cys Leu Phe Ile Ile Glu Thr Phe Glu
        210                 215                 220

Arg Thr Leu Thr Gln Asp Gly Ile Asp Asn Tyr Asn Ala Ala Ile Gly
225                 230                 235                 240

Lys Leu Asn Thr Ala Ile Asn Leu Phe Asn Gln Gln Asn Lys Lys Gln
                245                 250                 255

Glu Gly Phe Arg Lys Val Pro Gln Met Lys Cys Leu Tyr Lys Gln Ile
                260                 265                 270

Leu Ser Asp Arg Glu Glu Ala Phe Ile Asp Glu Phe Ser Asp Asp Glu
            275                 280                 285

Asp Leu Ile Thr Asn Ile Glu Ser Phe Ala Glu Asn Met Asn Val Phe
        290                 295                 300

Leu Asn Ser Glu Ile Ile Thr Asp Phe Lys Ile Ala Leu Val Glu Ser
305                 310                 315                 320

Asp Gly Ser Leu Val Tyr Ile Lys Asn Asp Val Ser Lys Thr Ser Phe
                325                 330                 335

Ser Asn Ile Val Phe Gly Ser Trp Asn Ala Ile Asp Glu Lys Leu Ser
                340                 345                 350

Asp Glu Tyr Asp Leu Ala Asn Ser Lys Lys Lys Asp Glu Lys Tyr
            355                 360                 365

Tyr Glu Lys Arg Gln Lys Glu Leu Lys Lys Asn Lys Ser Tyr Asp Leu
        370                 375                 380

Glu Thr Ile Ile Gly Leu Phe Asp Asp Asn Ser Asp Val Ile Gly Lys
385                 390                 395                 400

Tyr Ile Glu Lys Leu Glu Ser Asp Ile Thr Ala Ile Ala Glu Ala Lys
                405                 410                 415

Asn Asp Phe Asp Glu Ile Val Leu Arg Lys His Asp Lys Asn Lys Ser
                420                 425                 430

Leu Arg Lys Asn Thr Asn Ala Val Glu Ala Ile Lys Ser Tyr Leu Asp
        435                 440                 445

Thr Val Lys Asp Phe Glu Arg Asp Ile Lys Leu Ile Asn Gly Ser Gly
        450                 455                 460

Gln Glu Val Glu Lys Asn Leu Val Val Tyr Ala Glu Gln Glu Asn Ile
465                 470                 475                 480

Leu Ala Glu Ile Lys Asn Val Asp Ser Leu Tyr Asn Met Ser Arg Asn
                485                 490                 495

Tyr Leu Thr Gln Lys Pro Phe Ser Thr Glu Lys Phe Lys Leu Asn Phe
            500                 505                 510

Asn Arg Ala Thr Leu Leu Asn Gly Trp Asp Lys Asn Lys Glu Thr Asp
        515                 520                 525

Asn Leu Gly Ile Leu Phe Glu Lys Asp Gly Met Tyr Tyr Leu Gly Ile
        530                 535                 540

Met Asn Thr Lys Ala Asn Lys Ile Phe Val Asn Ile Pro Lys Ala Thr
545                 550                 555                 560

Ser Asn Asp Val Tyr His Lys Val Asn Tyr Lys Leu Leu Pro Gly Pro
                565                 570                 575

Asn Lys Met Leu Pro Lys Val Phe Phe Ala Gln Ser Asn Leu Asp Tyr
                580                 585                 590

Tyr Lys Pro Ser Glu Glu Leu Leu Ala Lys Tyr Lys Ala Gly Thr His
            595                 600                 605
```

-continued

```
Lys Lys Gly Asp Asn Phe Ser Leu Glu Asp Cys His Ala Leu Ile Asp
    610             615             620

Phe Phe Lys Ala Ser Ile Glu Lys His Pro Asp Trp Ser Ser Phe Gly
625             630             635             640

Phe Glu Phe Ser Glu Thr Cys Thr Tyr Glu Asp Leu Ser Gly Phe Tyr
            645             650             655

Arg Glu Val Glu Lys Gln Gly Tyr Lys Ile Thr Tyr Thr Asp Val Asp
            660             665             670

Ala Asp Tyr Ile Thr Ser Leu Val Arg Asp Glu Leu Tyr Leu Phe
        675             680             685

Gln Ile Tyr Asn Lys Asp Phe Ser Pro Tyr Ser Lys Gly Asn Leu Asn
690             695             700

Leu His Thr Ile Tyr Leu Gln Met Leu Phe Asp Gln Arg Asn Leu Asn
705             710             715             720

Asn Val Val Tyr Lys Leu Asn Gly Glu Ala Glu Val Phe Tyr Arg Pro
            725             730             735

Ala Ser Ile Asn Asp Glu Glu Val Ile Ile His Lys Ala Gly Glu Glu
        740             745             750

Ile Lys Asn Lys Asn Ser Lys Arg Ala Val Asp Lys Pro Thr Ser Lys
    755             760             765

Phe Gly Tyr Asp Ile Ile Lys Asp Arg Arg Tyr Ser Lys Asp Lys Phe
770             775             780

Met Leu His Ile Pro Val Thr Met Asn Phe Gly Val Asp Glu Thr Arg
785             790             795             800

Arg Phe Asn Asp Val Val Asn Asp Ala Leu Arg Asn Asp Glu Lys Val
            805             810             815

Arg Val Ile Gly Ile Asp Arg Gly Glu Arg Asn Leu Leu Tyr Val Val
            820             825             830

Val Val Asp Thr Asp Gly Thr Ile Leu Glu Gln Ile Ser Leu Asn Ser
        835             840             845

Ile Ile Asn Asn Glu Tyr Ser Ile Glu Thr Asp Tyr His Lys Leu Leu
    850             855             860

Asp Glu Lys Glu Gly Asp Arg Asp Arg Ala Arg Lys Asn Trp Thr Thr
865             870             875             880

Ile Glu Asn Ile Lys Glu Leu Lys Glu Gly Tyr Leu Ser Gln Val Val
            885             890             895

Asn Val Ile Ala Lys Leu Val Leu Lys Tyr Asn Ala Ile Ile Cys Leu
            900             905             910

Glu Asp Leu Asn Phe Gly Phe Lys Arg Gly Arg Gln Lys Val Glu Lys
        915             920             925

Gln Val Tyr Gln Lys Phe Glu Lys Met Leu Ile Asp Lys Leu Asn Tyr
    930             935             940

Leu Val Ile Asp Lys Ser Arg Lys Gln Asp Lys Pro Glu Glu Phe Gly
945             950             955             960

Gly Ala Leu Asn Ala Leu Gln Leu Thr Ser Lys Phe Thr Ser Phe Lys
            965             970             975

Asp Met Gly Lys Gln Thr Gly Ile Ile Tyr Tyr Val Pro Ala Tyr Leu
            980             985             990

Thr Ser Lys Ile Asp Pro Thr Thr Gly Phe Ala Asn Leu Phe Tyr Val
        995             1000            1005

Lys Tyr Glu Asn Val Glu Lys Ala Lys Glu Phe Phe Ser Arg Phe
    1010            1015            1020

Asp Ser Ile Ser Tyr Asn Asn Glu Ser Gly Tyr Phe Glu Phe Ala
```

```
              1025                1030                1035
Phe Asp Tyr Lys Lys Phe Thr Asp Arg Ala Cys Gly Ala Arg Ser
        1040                1045                1050
Gln Trp Thr Val Cys Thr Tyr Gly Glu Arg Ile Ile Lys Phe Arg
        1055                1060                1065
Asn Thr Glu Lys Asn Asn Ser Phe Asp Asp Lys Thr Ile Val Leu
        1070                1075                1080
Ser Glu Glu Phe Lys Glu Leu Phe Ser Ile Tyr Gly Ile Ser Tyr
        1085                1090                1095
Glu Asp Gly Ala Glu Leu Lys Asn Lys Ile Met Ser Val Asp Glu
        1100                1105                1110
Ala Asp Phe Phe Arg Ser Leu Thr Arg Leu Phe Gln Gln Thr Met
        1115                1120                1125
Gln Met Arg Asn Ser Ser Asn Asp Val Thr Arg Asp Tyr Ile Ile
        1130                1135                1140
Ser Pro Ile Met Asn Asp Arg Gly Glu Phe Phe Asn Ser Glu Ala
        1145                1150                1155
Cys Asp Ala Ser Lys Pro Lys Asp Ala Asp Ala Asn Gly Ala Phe
        1160                1165                1170
Asn Ile Ala Arg Lys Gly Leu Trp Val Leu Glu Gln Ile Arg Asn
        1175                1180                1185
Thr Pro Ser Gly Asp Lys Leu Asn Leu Ala Met Ser Asn Ala Glu
        1190                1195                1200
Trp Leu Glu Tyr Ala Gln Arg Asn Gln Ile
        1205                1210

<210> SEQ ID NO 13
<211> LENGTH: 3786
<212> TYPE: DNA
<213> ORGANISM: Agathobacter rectalis

<400> SEQUENCE: 13
aacaacggca caaacaattt ccagaacttc attggcattt catcactcca gaagaccctg      60
aggaatgccc tgacacctac cgagacaacc cagcaattca ttgtgaagaa cggaatcatt     120
aaggaggacg aactgagagg cgagaaccgc cagatcctga agacatcat  ggacgactac     180
tatcgcggtt tcatctccga cactcagc agcattgatg atattgattg acatctctg       240
tttgagaaga tggaaatcca gctgaagaat ggcgacaaca aggacactct cattaaggag     300
caagcagaga agaaaaggc tatctacaag aagtttgcag acgacgatcg cttcaagaat     360
atgtttagcg caaagctgat aagtgatatt ctcccagagt ttgtgattca acaacaac      420
tattctgcca gcgagaagga agagaagaca caggtcatca agctcttctc tcggtttgcc     480
acctcattca agattactt caagaatcgg gcaaattgtt tctctgccga tgacatctca     540
tcttcctcct gtcacagaat cgttaatgat aacgccgaaa tcttcttctc aaatgccctg     600
gtgtaccgga gaatcgtgaa gaatctgagt aacgacgaca tcaataagat tagcggtgat     660
atgaaggact ctctgaagaa gatgtccctg gagaagatat acagctatga gaagtacggc     720
gagttcatca ctcaagaggg aattagcttc tacaacgaca tttgtggcaa ggttaactca     780
ttcatgaatc tctactgcca agaacaag gagaataaga atctgtacaa actgcgcaaa     840
ctgcataagc aaatcctgtg tatcgccgac acctcttatg aggtgcccta caagtttgag     900
tctgacgaag aggtgtacca gtccgtgaac ggattcctgg acaacatcag ttctaaacac     960
atcgtcgagc ggctgaggaa gatcggcgac aactacaatg ctataacct ggacaagata    1020
```

```
tacatcgtca gtaagttcta tgaaagtgtg agtcagaaga cctaccggga ctgggagact    1080
atcaacaccg cactcgaaat ccactacaat aacatcctgc ctggcaacgg taagagcaag    1140
gccgacaagg tgaagaaggc cgtcaagaac gacctccaga agagcatcac cgagattaac    1200
gaactggtga gtaactacaa gctctgccca gacgataaca ttaaggcaga aacctacatt    1260
catgagattt cccatatact gaacaacttt gaagctcaag agctgaaata caatcccgag    1320
attcatctgg tggagagcga gctgaaagca tccgagctga agaacgttct cgacgtcatc    1380
atgaacgcct tccactggtg tagcgtgttc atgactgagg agctggtcga taaagacaac    1440
aatttctacg ccgagctgga agaaatctac gacgagatat accctgtgat tagcctctac    1500
aatctggtcc ggaactatgt gacccagaag ccctattcaa ctaagaagat caagctgaac    1560
tttgggattc ctaccctggc cgacggctgg tccaagagca agagtattc caataacgca    1620 atcatcctga tgagagacaa cctgtattac ctcggtatct taacgctaa gaataagccc    1680 gagaagaaga tcatcgaagg aaatacatcc gagaacaagg gcgactacaa gaagatgatc    1740
tataacctgc tgcctggccc aaacaagatg atccctaagg tgttcctgag cagcaagacc    1800
ggagtcgaga cttacaagcc aagtgcctac atactggagg ctataagca gaacaagcac    1860 ctgaaatcta gcaaagattt cgacatcact ttctgtcgcg acctgatcga ctatttcaag    1920
aattgtattg ccatccaccc agagtggaag aatttcggat tcgacttctc tgacacctcc    1980
acatacgagg acatcagtgg cttctataga gaagtggagc tgcaaggtta caagatcgac    2040
tggacctaca tatctgagaa agacatcgac ctgctgcaag agaaagggca gctctacctc    2100
ttccaaatct acaacaagga ctttagtaag aagtctacag gtaatgacaa tctgcacact    2160
atgtacctga agaatctctt ctctgaagag aacctcaaag acgtggtgct gaaactgaac    2220
ggcgaagcag aaatcttctt tcgcaaatca tccattaaga atcctatcat acacaagaag    2280
ggtagtatcc tggtgaacag gacatacgaa gccgaggaga aagatcagtt cggcaacatt    2340
cagattgtgc gcaagactat tcccgagaat atctaccagg agctgtacaa atacttcaac    2400
gataagtctg ataaagagct gtcagacgaa gcagccaagc tgaagaatgc tgtgggacat    2460
catgaagcag ctactaacat cgtgaaagac tatagataca catacgacaa gtatttcctg    2520
cacatgccaa ttaccatcaa cttcaaagcc aataagactt ctttcattaa cgaccgcatc    2580
ctccagtaca ttgcaaagga gaaagacctg cacgtgatcg ggattgatcg cggagaacgg    2640
aacctcatct acgtttcagt catcgacaca tgcggtaaca tcgtcgaaca gaagagcttc    2700
aacattgtta tgggtatga ttaccagatc aaactcaagc aacaggaagg cgcacggcag    2760
attgctcgca aggagtggaa ggaaattggc aagatcaagg aaatcaagga aggatacctc    2820
agcctcgtca ttcatgaaat cagcaagatg gtgatcaagt ataacgcaat catcgctatg    2880
gaggacctga gttatggctt caagaaaggc agattcaagg tggagcggca agtctaccag    2940
aaattcgaaa caatgctgat caacaagctg aactacctgg tgttcaaaga catcagcata    3000
accgagaacg gaggactcct gaaaggctac cagctcacat acatcccaga gaaactcaag    3060
aatgtgggcc accaatgcgg ctgcatcttc tacgtccctg ccgcttacac cagcaagata    3120
gatcccacta caggattcgt gaacatattc aaattcaagg atctgacagt ggacgccaag    3180
agggagttca tcaagaagtt tgatagtatt cgctatgaca gcgataagaa tctgttctgt    3240 ttcaccttg actacaacaa cttcattacc cagaataccg ttatgtccaa gtctagctgg    3300
agtgtgtata cctacggtgt tcggatcaag cggaggtttg tcaatggtag attctcaaac    3360
```

```
gaaagcgaca ccatcgacat cacaaaggac atggagaaga cactggaaat gactgacata    3420
aactggagag atggacacga cctgcggcaa gacatcattg actacgagat cgttcagcac    3480
atctttgaaa tcttcaagct gactgttcag atgcggaata gtctgagcga gctggaggac    3540
cggaattacg accgcctgat ctcaccagtc ctgaacgaga taacatctt ctacgattct     3600
```

```
gccaaagcag gagatgccct gccaaaggac gctgatgcaa acggtgccta ctgcatcgcc    3660
ctcaaaggtc tgtacgaaat caagcagatt accgagaatt ggaaggagga cgggaagttc    3720
agcagagaca agctcaagat cagcaataag gactggttcg atttcattca gaacaagcgc    3780
tacctg                                                                3786
```

<210> SEQ ID NO 14
<211> LENGTH: 3918
<212> TYPE: DNA
<213> ORGANISM: Lachnospira pectinoschiza

<400> SEQUENCE: 14

```
atgatcatga caacgtgac cggcgacttc agcgagttcg tggccatcag caaggtgcag      60
aagaccctgc gcaacgagct gcgccccacc ccctgacca tgaagcacat caagcagaag    120
ggcatcatca ccgaggacga gtacaagacc cagcagagcc tggagctgaa gcgcatcgcc    180
gacggctact accgcgacta catcacccac aagctgaacg acaccaacaa cctggacttc    240
cgcaacctgt tcgaggccat cgaggagaag tacaagaaga cgacaaggga caaccgcgac    300
aagctggacc tggtggagaa gagcaagcgc ggcgagatcg ccaagctgct gagcgccgac    360
gacaacttca gagcatgtt cgaggccaag ctgatcaccc agctgctgcc cgtgtacgtg     420
gagcagaact acatcggcga ggacaaggag aaggccctgg agaccatcgc cctgttcaag    480
ggcttcacca cctacttcac cgactacttc aacatccgca gaacatgtt caaggagaac     540 ggcggcgcca gcagcatctg ctaccgcatc gtgaacgtga acgccagcat cttctacgac    600
aacctgaaga ccttcatgtg catcaaggag aaggccgaga ccgagatcgc cctgatcgag    660
gaggagctga ccgagctgct ggacagctgg cgcctggagc acatcttcag cgaggactac    720
tacaacgagc tgctggccca gaagggcatc gactactaca ccagatctg cggcgacgtg     780 aacaagcaca tgaacctgta ctgccagcag aacaagctga aggccaacgt gttcaagatg    840
accaagctgc agaagcagat catgggcatc agcgagaagg ccttcgagat ccccccatg     900 taccagaacg acgaggaggt gtacgccgcc ttcaacggct catcagccg cctggaggag     960 gtgaagctga tcgaccgcct gggcaacgtg ctgcagaaca gcaacatcta cgacaccgcc   1020
aagatctaca tcaacgcccg ctgctacacc aacgtgagca gctacgtgta cggcggctgg   1080
ggcgtgatcg agagcgccat cgagcgctac tggtacaaca ccatcgccgg caagggccag   1140
agcaaggcca gaagatcga aaggccaag aaggacaaca agttcatgag cgtgaaggag     1200
ctggacagca tcgtgagcga ctacgagccc gactacttca cgccagcaa catggacgac   1260 gacaacagcg gccgcgcctt cagcggccac ggcgtgctgg gctacttcaa caagatgagc   1320
aagctgctgg ccaacatgag cctgcacacc atcacctacg acagcggcga cagcctgatc   1380
gagaacaagg agaccgccct gaacatcaag aaggacctgg acgacatcat gagcatctac   1440
cactggctgc agaccttcat catcgacgag gtggtggaga aggacaacgc cttctacgcc   1500
gagctggagg acatctacta cgagctggag aacgtggtga ccctgtacga ccgcatccgc   1560
aactacgtga cccgcaagcc ctacagcacc cagaagttca gcttaacttc gccagcccc    1620 accctggcca gcggctggag ccgcagcaag gagttcgaca caacgccat catcctgctg     1680
```

```
cgcaacaaca agtactacat cgccatcttc aacgtgaaca acaagcccga caagcagatc    1740
atcaagggca gcgaggagca gcgcctgagc accgactaca agaagatggt gtacaacctg    1800
ctgcccggcc ccaacaagat gctgccctgg gtgttcatca agagcaacac cggcaagcgc    1860
gactacaacc ccagcagcta catcctggag ggctacgaga agaaccgcca catcaagagc    1920
agcggcaact tcgacatcaa ctactgccac gacctgatcg actactacaa ggcctgcatc    1980
aacaagcacc ccgagtggaa gaactacggc ttcaagttca aggagaccac ccagtacaac    2040
gacatcggcc agttctacaa ggacgtggag aagcagggct acagcatcag ctgggcctac    2100
atcagcgagg ccgacatcaa ccgcctggac gaggagggca agatctacct gttcgagatc    2160
tacaacaagg acctgagcag ccacagcacc ggcaaggaca acctgcacac catgtacctg    2220
aagaacatct tcagcgagga caacctgaag aacatctgca tcgagctgaa cggcaacgcc    2280
gagctgttct accgcaagag cagcatgaag cgcaacatca cccacaagaa ggacaccgtg    2340
ctggtgaaca agacctacat caacgaggcc ggcgtgcgcg tgagcctgac cgacgaggac    2400
tacatcaagg tgtacaacta ctacaacaac gactacgtga tcgacgtgga aggacaag    2460 aagctggtgg agatcctgga gcgcatcggc accgcaaga accccatcga catcatcaag    2520
gacaagcgct acaccgagga caagtacttc ctgcacttcc ccatcaccat caactacggc    2580
gtggacgacg agaacatcaa cgccaagatg atcgagtaca tcgccaagca acaacatg    2640 aacgtgatcg gcatcgaccg cggcgagcgc aacctgatct acatcagcgt gatcaacaac    2700
aagggcaaca tcatcgagca gaagagcttc aacctggtga caactacga ctacaagaac    2760 aagctgaaga acatggagaa gacccgcgac aacgcccgca agaactggca ggagatcggc    2820
aagatcaagg acgtgaagaa cggctacctg agcggcgtga tcagcaagat cgcccgcatg    2880
gtggtggact acaacgccat catcgtgatg gaggacctga accgcggctt caagcgcggc    2940
cgcttcaagg tggagcgcca ggtgtaccag aagttcgaga acatgctgat cagcaagctg    3000
aactacctgg tgttcaagga agaaggcc gacgagaacg gcggcatcct gaagggctac    3060
cagctgacct accctgcccaa gagcgccctg cagatcggca gcagtgcgg ctgcatcttc    3120 tacgtgcccg ccgcctacac cagcaagatc gaccccgcca ccggcttcat caacatcttc    3180
gacttcaaga agtacagcgg cagcgccatc aacgccaagg tgaaggacaa gaaggagttc    3240
ctgatgagca tgaacagcat ccgctacgtg aacgagggca gcgccgagta cgagaagatc    3300
ggccaccgcc agctgttcgc cttcagcttc gactacaaca acttcaagac ctacaacgtg    3360
agcatccccg tgaacgagtg gaccacctac acctacggcg agcgcatcaa gagctgtac    3420 aaggacggcc gctggagcgg cagcgaggtg ctgaacctga ccgaggacct gatcgagctg    3480
atggagcagt acgcatcga gtacaaggac ggccacgaca tccgcgagga catcagccac    3540
atggacgaga tgcgcaacgc cgacttcatc tgcaacctgt tcgagaagtt caagtacacc    3600
gtgcagctgc gcaacagcaa gagcgaggcc gagggcgacg actacgaccg cctggtgagc    3660
cccgtgctga acagccacaa cggcttcttc gacagcagcg actacaagga gaacgagaag    3720
agcgacgaca tcatcgacga caagcagatc atgcccaagg acgccgacgc caacggcgcc    3780
tactgcatcg ccctgaaggg cctgtacgag atcaacaaga tcaaggagaa ctggagcgac    3840
gacaagaagc tgaaggagag cgagctgtac atcggcgtga ccgagtggct ggactacatc    3900
cagaaccgcc gcttcgag                                                  3918
```

<210> SEQ ID NO 15

```
<211> LENGTH: 2823
<212> TYPE: DNA
<213> ORGANISM: Sneathia amnii

<400> SEQUENCE: 15
atgaacgaca ttgaaggact gaaggaggaa tttctgaaga tttccctgga gaactttgag      60
ggtatctaca tcagcaataa gaagctgaat gagatttcta accggaaatt cggcgactac     120
aacagcatta acatgatgat caagcagagc atgaatgaga agggtattct gtccaagaag     180
gagatcaacg aactcatacc cgatctggag aacatcaaca agcctaaggt caagtctttc     240
aatctgagtt tcatcttcga gaacctcacc aaagagcata aggaactgat catcgactac     300
atcagggaga acatctgcaa cgtgattgag aatgtcaaga ttacaataga gaaatacagg     360
aacattgata caagatcga gtttaagaac aatgctgaga aggtgtccaa gattaaggaa     420
atgctggaga gcatcaacga gctgtgtaaa ctgattaagg agttcaacac agacgagatt     480
gagaagaaca atgagttcta taacattctc aataagaatt tcgaaatctt cgaatccagt     540
tacaaggttc tgaataaggt ccggaacttt gtgaccaaga agaagttat tgagaataag     600
atgaagctga attttctcaaa ctatcagctc gggaacggct ggcacaagaa caaagagaag     660
gactgtagca ttatcctgtt tcgcaagaga acaatgagc gctggatata ctacctcggg     720
attctgaagc atggtacaaa gatcaaagag aacgactatc tctcatcagt ggacacaggg     780
ttctacaaga tggactatta cgcacagaat agtctgtcaa agatgattcc aaagtgcagc     840
attacagtta gaacgtcaa gaacgctcca gaggacgagt ctgtcattct gaacgattcc     900
aagaagttca atgaacctct ggagatcaca cccgagataa gaaagctgta cggcaataac     960
gagcacatca agggcgacaa attcaagaaa gagtccctgg tcaagtggat agacttctgt    1020
aaggagtttc tgctgaaata caagagtttc gagaaggcca agaaggaaat cctcaaactc    1080
aaagaatcaa acctctatga gaacctggag gagttctaca gcgatgccga ggagaaagcc    1140
tacttcctgg agttcatcaa cattgatgag acaagatca agaagctggt caaggagaag    1200
aatctgtacc tcttccagat atacaacaaa gactttagcg cttattcaac cggcaataag    1260
aacctccata ccatgtatt cgaggagctg ttcactgatg agaatctcaa gaagcctgtg    1320
ttcaagctca acggaaacac agaagtgttc tacagaattg ccagtagtaa gccaaagatc    1380
gtgcacaaca agggagagaa actggtcaac aagacatacc tcgacgatgg catcattaag    1440
acaattccag attctgtgta cgaagagatt tcagagaaag tcaagaacaa cgaggactac    1500
tccaagctgc tcgaagagaa taacatcaag aatctggaaa tcaaggtggc aactcatgaa    1560
attgtgaaag ataaacgcta ctttgagaac aaattcctgt tctatctgcc catcacactg    1620
aacaagaagg tgtctaacaa gaataccaat aagaacatca acaagaatgt catcgacgag    1680
attaaggatt gtaacgagta aacgtcatt gggattgata gaggtgagcg gaacctgatt    1740
agcctgtgca tcatcaatca gacggcgaa atcatactcc agaaggagat gaacatcatt    1800
caatctagcg acaagtataa cgtggactat aacgagaaac tggagatcaa gtctaaggag    1860
agggacaacg ctaagaagaa ctggagcgaa atcgggaaga taaggaccct gaagagcgga    1920
tacctctccg ctgtggtgca cgagattgtc aagctggcaa tcgaatacaa cgctgtgatc    1980
attctggagg acctcaacaa cgggtttaag aactcaagga gaaggttga taaacagata    2040
taccagaaat cgagagggc tctgattgag aagctgcaat ttctcatctt caagaactat    2100
gacaagaatg agaaaggagg actcaggaat gctttccagc tgactcccga actgaagaac    2160
atcaccaagg tggcatccca gcagggcatc ataatctaca caaatccagc ctataccagc    2220
```

```
aagatcgacc ctaccacagg ttatgcaaac ataatcaaga agagcaacaa taacgaggag      2280
tctatcgtga aggcaatcga caagatttcc tatgacaaag agaaagacat gttctacttc      2340
gacattaacc tgtcaaatag ctcctttaac ctgaccgtta agaatgtgct caagaaggaa      2400
tggcgcatct acaccaatgg cgagagaatc atctataagg atcgcaagta cattacactg      2460
aatatcacac aagagatgaa agacatcctg tcaaagtgcg gcattgatta tctgaacatc      2520
gacaacctga acaggacat tctcaagaac aaactgcata agaaggtcta ctatatcttc       2580
gagctggcta acaagatgcg caacgagaat aaggacgtgg attacataat cagcccagtg      2640
ctgaataagg atggaaagtt cttcatgacc caagagatca acgagctgac accaaaggat      2700
gccgacctga acggagccta acatagct ctgaagggca agctgatgat tgacaacctg         2760
aataagaagg agaagtttgt ctttctcagc aatgaagatt ggctcaattt catccagggt      2820
cgg                                                                    2823

<210> SEQ ID NO 16
<211> LENGTH: 3930
<212> TYPE: DNA
<213> ORGANISM: Helcococcus kunzii

<400> SEQUENCE: 16
atgttcgaga agctgagcaa catcgtgagc atcagcaaga ccatccgctt caagctgatc       60
cccgtgggca agaccctgga gaacatcgag aagctgggca agctggagaa ggacttcgag      120
cgcagcgact tctaccccat cctgaagaac atcagcgacg actactaccg ccagtacatc      180
aaggagaagc tgagcgacct gaacctggac tggcagaagc tgtacgacgc ccacgagctg      240
ctggacagca gcaagaagga gagccagaag aacctggaga tgatccaggc ccagtaccgc      300
aaggtgctgt tcaacatcct gagcggcgag ctggacaaga gcggcgagaa gaacagcaag      360
gacctgatca agaacaacaa ggccctgtac ggcaagctgt tcaagaagca gttcatcctg      420
gaggtgctgc ccgacttcgt gaacaacaac gacagctaca gcgaggagga cctggagggc      480
ctgaacctgt acagcaagtt caccaccccg ctgaagaact tctgggagac ccgcaagaac      540
gtgttcaccg acaaggacat cgtgaccgcc atccccttcc gcgccgtgaa cgagaacttc      600
ggcttctact acgacaacat caagatcttc aacaagaaca tcgagtacct ggagaacaag      660
atccccaacc tggagaacga gctgaaggag gccgacatcc tggacgacaa ccgcagcgtg      720
aaggactact tcaccccccaa cggcttcaac tacgtgatca cccaggacgg catcgacgtg      780
taccaggcca tccgcggcgg cttcaccaag gagaacggcg agaaggtgca gggcatcaac      840
gagatcctga acctgaccca gcagcagctg cgccgcaagc ccgagaccaa gaacgtgaag      900
ctgggcgtgc tgaccaagct cgcaagcag atcctggagt acagcgagag caccagcttc       960
ctgatcgacc agatcgagga cgacaacgac ctggtggacc gcatcaacaa gttcaacgtg     1020
agcttcttcg agagcaccga ggtgagcccc agcctgttcg agcagatcga cgcctgtac      1080 aacgccctga gagcatcaa gaaggaggag gtgtacatcg acgcccgcaa cacccagaag      1140
ttcagccaga tgctgttcgg ccagtgggac gtgatccgcc gcggctacac cgtgaagatc      1200
accgagggca gcaaggagga gaagaagaag tacaaggagt acctggagct ggacgagacc      1260
agcaaggcca gcgctacct gaacatccgc gagatcgagg agctggtgaa cctggtggag       1320
ggcttcgagg aggtggacgt gttcagcgtg ctgctggaga agttcaagat gaacaacatc      1380
gagcgcagcg agttcgaggc ccccatctac ggcagcccca tcaagctgga ggccatcaag      1440
```

-continued

| | |
|---|---|
| gagtacctgg agaagcacct ggaggagtac cacaagtgga agctgctgct gatcggcaac | 1500 |
| gacgacctgg acaccgacga gaccttctac cccctgctga acgaggtgat cagcgactac | 1560 |
| tacatcatcc ccctgtacaa cctgacccgc aactacctga cccgcaagca cagcgacaag | 1620 |
| gacaagatca aggtgaactt cgacttcccc accctggccg acggctggag cgagagcaag | 1680 |
| atcagcgaca accgcagcat catcctgcgc aagggcggct actactacct gggcatcctg | 1740 |
| atcgacaaca agctgctgat caacaagaag aacaagagca gaagatcta cgagatcctg | 1800 |
| atctacaacc agatccccga gttcagcaag agcatcccca actacccctt caccaagaag | 1860 |
| gtgaaggagc acttcaagaa caacgtgagc gacttccagc tgatcgacgg ctacgtgagc | 1920 |
| cccctgatca tcaccaagga gatctacgac atcaagaagg agaagaagta caagaaggac | 1980 |
| ttctacaagg acaacaacac caacaagaac tacctgtaca ccatctacaa gtggatcgag | 2040 |
| ttctgcaagc agttcctgta caagtacaag ggccccaaca aggagagcta caaggagatg | 2100 |
| tacgacttca gcaccctgaa ggacaccagc ctgtacgtga acctgaacga cttctacgcc | 2160 |
| gacgtgaaca gctgcgccta ccgcgtgctg ttcaacaaga tcgacgagaa caccatcgac | 2220 |
| aacgccgtgg aggacggcaa gctgctgctg ttccagatct acaacaagga cttcagcccc | 2280 |
| gagagcaagg gcaagaagaa cctgcacacc ctgtactggc tgagcatgtt cagcgaggag | 2340 |
| aacctgcgca cccgcaagct gaagctgaac ggccaggccg agatcttcta ccgcaagaag | 2400 |
| ctggagaaga agcccatcat ccacaaggag ggcagcatcc tgctgaacaa gatcgacaag | 2460 |
| gagggcaaca ccatccccga gaacatctac cacgagtgct accgctacct gaacaagaag | 2520 |
| atcggccgcg aggacctgag cgacgaggcc atcgccctgt caacaaggga cgtgctgaag | 2580 |
| tacaaggagg cccgcttcga catcatcaag gaccgccgct acagcgagag ccagttcttc | 2640 |
| ttccacgtgc ccatcacctt caactgggac atcaagacca caagaacgt gaaccagatc | 2700 |
| gtgcagggca tgatcaagga cggcgagatc aagcacatca tcggcatcga ccgcggcgag | 2760 |
| cgccacctgc tgtactacag cgtgatcgac ctggagggca catcgtgga gcagggcagc | 2820 |
| ctgaacaccc tggagcagaa ccgcttcgac aacagcaccg tgaaggtgga ctaccagaac | 2880 |
| aagctgcgca cccgcgagga ggaccgcgac cgcgcccgca agaactggac caacatcaac | 2940 |
| aagatcaagg agctgaagga cggctacctg agccacgtgg tgcacaagct gagccgcctg | 3000 |
| atcatcaagt acgaggccat cgtgatcatg gagaacctga ccagggcttc aagcgcggc | 3060 |
| cgcttcaagg tggagcgcca ggtgtaccag aagttcgagc tggccctgat gaacaagctg | 3120 |
| agcgccctga gcttcaagga gaagtacgac gagcgcaaga acctggagcc cagcggcatc | 3180 |
| ctgaacccca tccaggcctg ctacccgtg gacgcctacc aggagctgca gggccagaac | 3240 |
| ggcatcgtgt tctacctgcc cgccgcctac accagcgtga tcgacccgt gaccggcttc | 3300 |
| accaacctgt tccgcctgaa gagcatcaac agcagcaagt acgaggagtt catcaagaag | 3360 |
| ttcaagaaca tctacttcga caacgaggag gaggacttca gttcatctt caactacaag | 3420 |
| gacttcgcca aggccaacct ggtgatcctg aacaacatca gagcaagga ctggaagatc | 3480 |
| agcacccgcg gcgagcgcat cagctacaac agcaagaaga aggagtactt ctacgtgcag | 3540 |
| cccaccgagt tcctgatcaa caagctgaag gagctgaaca tcgactacga gaacatcgac | 3600 |
| atcatccccc tgatcgacaa cctggaggag aaggccaagc gcaagatcct gaaggccctg | 3660 |
| ttcgacacct tcaagtacag cgtgcagctg cgcaactacg acttcgagaa cgactacatc | 3720 |
| atcagcccca ccgccgacga caacggcaac tactacaaca gcaacgagat cgacatcgac | 3780 |
| aagaccaacc tgcccaacaa cggcgacgcc aacgcgcct tcaacatcgc ccgcaagggc | 3840 |

```
ctgctgctga aggaccgcat cgtgaacagc aacgagagca aggtggacct gaagatcaag    3900
aacgaggact ggatcaactt catcatcagc                                    3930

<210> SEQ ID NO 17
<211> LENGTH: 2952
<212> TYPE: DNA
<213> ORGANISM: Arcobacter butzleri

<400> SEQUENCE: 17
atgttcagcc tggactactt cagcctgacc ctgagccagc gctacatcga catctacaac     60
accatgatcg gcggcaacac cctggccgac ggcaccaagg tgcagggcat caacgagaac    120
atcaacatct accgccagaa gaacaacatc gaccgcaaga acctgcccac cctgaagccc    180
ctgcacaagc agctgctgag cgaccgcgag accctgagct ggatccccga ggccttcaag    240
accaaggagg aggtggtggg cgccatcgag gacttctaca gaacaacat catcagcttc    300 aagtgctgcg acaacatcgt ggacatcacc aagcagttca tcgacatctt cagcctgaac    360
gaggactacg agctgaacaa gatcttcatc aagaacgaca tcagcatcac cagcatcagc    420
caggacatct tcaaggacta ccgcatcatc aaggaggccc tgtggcagaa gcacatcaac    480
gagaacccca aggccgccaa gagcaaggac ctgaccggcg acaaggagaa gtacttcagc    540
cgcaagaaca gcttcttcag cttcgaggag atcatcagca gcctgaagct gatgggccgc    600
aagatcgacc tgttcagcta cttcaaggac aacgtggagt accgcgccca cagcatcgag    660
accaccttca tcaagtggca gaagaacaag aacgacaaga gaccaccaa ggagctgctg     720 gacaacatcc tgaacctgca gcgcgtgctg aagcccctgt acctgaaggc cgaggtggag    780
aaggacatcc tgttctacag catcttcgac atctacttcg agagcctgaa cgagatcgtg    840
aagctgtaca acaaggtgcg cgacttcgag agcaagaagc cctacagcct ggagaagttc    900
aagctgaact tccagaacag cacccctgctg agcggctggg acgtgaacaa ggagcccgac    960
aacaccagca tcctgctgaa gaaggacggc ctgtactacc tgggcatcat ggacaagaag   1020
cacaaccgcg tgttcaagaa cctggagagc agcaagggcg gctacgagaa gatcgagtac   1080
aagctgctga gcggccccaa caagatgctg cccaaggtgt tcttcagcaa caagagcatc   1140
ggctactaca cccccagccc cgccctgctg gagaagtaca agagcggcgt gcacaagaag   1200
ggcgagagct tcgacctgaa cttctgccac gagctgatcg acttcttcaa ggccagcatc   1260
gacaagcacg aggactggaa gaacttcaac ttcaagttca gcgacaccag cgagtacgcc   1320
gacatcagcg gcttctaccg cgaggtggag cagcagggct acaagatcac cttcaagaac   1380
atcgacgagg agttcatcaa caccctgatc aacgagggca agctgtacct gttccagatc   1440
tacaacaagg acttcagcac cttcagcaag ggcaccaaga acctgcacac cctgtactgg   1500
gagatgatct tcaacgagga gaacctgaag aacgtggtgt acaagctgaa cggcgaggcc   1560
gagatcttct accgcaagaa gagcatcgag tacagcgagg acaagatgaa gtacggccac   1620
cactacgagg agctgaagga caagttcaac taccccatca tcaaggacaa gcgcttcacc   1680
atggacaagt tccagttcca cgtgcccatc accatgaact tcaaggccac cggccgcagc   1740
tacatcaacg aggaggtgaa cgacttcctg cgccagaaca gcaaggacgt gaagatcatc   1800
ggcatcaacc gcggcgagcg ccacctgatc tacctgacca tgatcaacgc caagggcgag   1860
atcatccagc agtacagcct gaacgagatc gtgaacagc acaacaacaa gaacttcacc   1920
gtgaactaca cgagaagct gagcaagaag gagggcgagc gcgccatcgc ccgcgagaac   1980
```

| | |
|---|---|
| tggggcgtgg tggagaacat caaggagctg aaggagggct acctgagcca cgccatccac | 2040 |
| accatcagca acctgatcgt ggagaacaac gccatcgtgg tgctggagga cctgaacttc | 2100 |
| gagttcaagc gcgagcgcct gaaggtggag aagagcatct accagaagtt cgagaagatg | 2160 |
| ctgatcgaca agctgaacta cctggtcgac aagaagaagg acatcaacga gaacggcggc | 2220 |
| ctgctgaagg ccctgcagct gaccaacaag ttcgagagct cgagaagat cggcaagcag | 2280 |
| aacggcttcc tgttcttcgt gaacgcctgg aacatcacca gatctgccc cgtgaccggc | 2340 |
| ttcgtgagcc tgttcgacac ccgctaccag agcgtggaca aggcccgcga gttcttcagc | 2400 |
| aagttcgaca gcatcaagta caacgaggag aaggagcact acgagttcgt gttcgactac | 2460 |
| agcaacttca ccgacaaggc caaggacacc aagaccaagt ggaccgtgtg cagctacggc | 2520 |
| acccgcatca gaccttccg caacagcgag aagaacaaca ctgggacaa caagaccgtg | 2580 |
| agccccaccg aggacctgag caagctgctg aagagctgcg accgcgacat caaggagttc | 2640 |
| atcatcagcc aggacaagaa ggagttcttc gtggagctgc tggagatctt cagcctgatc | 2700 |
| gtgcagatga agaacagcat catcaacagc gagatcgact acatcatcag ccccgtggcc | 2760 |
| aacgagaacg gcgagttctt cgacagccgc ttcgccaaca gcagcctgcc caagaacgcc | 2820 |
| gacgccaacc ccgcctacaa caccgcccgc aagggcctga tgctgctgga agatccgc | 2880 |
| gacagcgaga tcggcaagaa gatcgacatg aagatcacca caccgagtg gctgaacttc | 2940 |
| gtgcaggagc gc | 2952 |

<210> SEQ ID NO 18
<211> LENGTH: 3783
<212> TYPE: DNA
<213> ORGANISM: Bacteroidetes oral

<400> SEQUENCE: 18

| | |
|---|---|
| aggaaattca atgagttcgt gggtctgtat cctattagta agaccctcag gttcgagctg | 60 |
| aaaccaatcg gcaagacact ggagcatatc cagagaaaca agctcctgga gcatgatgcc | 120 |
| gttcgcgctg acgactatgt caaagtgaag aagatcattg acaaatacca taagtgtctg | 180 |
| atagatgagg ccctgtctgg attccacttc gatacagaag ccgatgggag aagcaataac | 240 |
| agcctgtctg agtactatct gtactacaat ctcaagaaga gaaatgagca ggaacagaag | 300 |
| actttcaaga caatccagaa caatctgcgg aagcagattg tcaacaagct gacccagagt | 360 |
| gagaagtata agagaattga taagaaagaa ctcatcacca ctgatctgcc agacttcctg | 420 |
| actaatgaaa gcgagaaaga actggtggag aagttcaaga actttactac ctactttacc | 480 |
| gaatttcaca agaaccgcaa gaatatgtac tccaaggaag agaagtccac cgcaatcgct | 540 |
| ttccgcctga ttaacgagaa cctgccaaag tttgtcgata catcgctgc tttcgagaaa | 600 |
| gttgtgtcct cacctctcgc agagaagatc aatgccctgt acgaggactt taaggagtat | 660 |
| ctgaatgtgg aagaaatctc acgggtgttt agactcgact attacgatga actgctgaca | 720 |
| cagaaacaga ttgatctgta caacgctatc gtcggtggtc ggacagagga ggacaacaag | 780 |
| atccagataa agggactgaa ccagtatatc aacgaataca tcagcagca gacagatcgg | 840 |
| tctaatcggc tgccaaagct gaaacctctc tataagcaaa ttctctccga cagagagagc | 900 |
| gtgtcatggc tgcctcccaa gtttgatagc gataagaatc tgctgattaa gatcaaagaa | 960 |
| tgctacgacg ccctgtccga gaaggagaaa gtgtttgaca agctggaaag tattctcaag | 1020 |
| agcctgtcaa cctatgacct gtctaagata tacatttcta cgactctca gctgtcttac | 1080 |
| attagccaga agatgtttgg acggtgggac atcatatcta aggccatcag ggaggattgt | 1140 |

```
gctaagagga atcctcagaa atctcgggaa tccctggaga agttcgccga gaggatagat    1200
aagaaactca agaccatcga ctccatcagc atcggcgatg tggatgagtg cctggcccag    1260
ctgggtgaaa cctacgttaa gcgggtggag gattactttg tggcaatggg cgaatccgag    1320
atcgacgatg agcagacaga taccacctcc ttcaagaaga acatagaggg agcatacgag    1380
tccgtcaagg agctgctgaa caacgctgat aacattacag acaataacct gatgcaggac    1440
aagggcaatg tggagaagat caagaccctg ctggatgcaa tcaaggacct ccagcggttc    1500
attaagccac tcctgggtaa aggtgacgaa gcagacaagg acggcgtgtt ctacggtgag    1560
tttacatccc tgtggaccaa actcgatcag gttactcctc tctataacat ggttcggaat    1620
tacctcactt caaagcctta tagtacaaag aagattaagc tgaactttga gaacagcact    1680
ctcatggatg gatgggatct gaataaggag ccagataaca ctaccgtgat attctgcaaa    1740
gatgggctgt attacctggg cattatgggt aagaagtaca atagagtgtt tgtcgataga    1800
gaggacctgc ctcacgacgg cgagtgctac gacaagatgg agtacaaact gctgccaggt    1860
gccaataaga tgctccctaa agtgttcttc tccgaaactg gtattcaacg gttcctccca    1920
tccgaggaac tcctgggcaa gtacgaaaga ggcacacata agaaaggagc tgggtttgac    1980
ctgggagact gtagagcact gattgatttc tttaagaaga gcattgaaag gcacgatgat    2040
tggaagaagt ttgacttcaa gttcagcgac acaagcacat accaggacat aagtgagttc    2100
tatagagaag tggagcagca gggctataag atgtccttta aaaggtttc tgtggactat    2160 atcaagtctc tggtggaaga aggtaagctg tatctgttcc agatatacaa caaagacttc    2220
tccgcacatt ccaaagggac acctaacatg cacactctct attggaagat gctgttcgat    2280
gaggagaacc tgaaggacgt ggtgtataag ctgaatggag aagctgaggt gttcttccgg    2340
aaatctagca tcacagtgca agcccaaca caccctgcta attcacctat caagaacaag    2400
aacaaggata tcagaagaa ggaatcaaag tttgagtacg atctcatcaa ggaccgcagg    2460
tataccgtgg acaagttcct ctttcacgtg cctataacca tgaatttcaa gtccgtcggt    2520
ggctctaaca tcaatcagct cgtgaagcgg cacattcggt ccgcaaccga cctccacatc    2580
atcggcatag atagaggaga gcggcatctg ctgtacctga ccgttatcga cagcagaggt    2640
aacatcaaag aacagttcag tctgaacgag atagtgaacg agtataacgg gaacacctat    2700
cggaccgatt accacgagct gctcgatacc agagaaggcg agagaacaga agctagacgg    2760
aactggcaga ctatacagaa catacgcgag ctgaaagagg gatacctctc ccaggtgatt    2820
cacaagatca gcgagctggc tatcaaatac aacgccgtga tcgtgctgga ggatctcaat    2880
ttcggcttta tgaggtcacg ccagaaagtg gagaagcagg tgtatcagaa attcgagaag    2940
atgctgatcg acaagctgaa ctacctggtc gataagaaga acctgtcgc tgaaaccgga    3000 gggctgctga gagcctacca gctgaccgga gaatttgagt cctttaagac cctgggaaag    3060
cagagcggca ttctgttcta cgttcccgct tggaacacca gtaagattga tcctgtgact    3120
gggtttgtca atctcttcga tacccactat gagaacattg agaaggctaa ggtgttcttt    3180
gacaaattca agagtatcag gtacaattcc gacaaggatt ggttcgaatt tgtcgtggac    3240
gactatacaa ggttctcacc taaggcagag ggcaccagga gggactggac tatctgcacc    3300
cagggaaagc gcattcagat atgtcggaac caccagcgca ataacgagtg ggagggtcaa    3360
gagattgacc tgaccaaagc attcaaggag cactttgaag cctatggcgt tgacatctca    3420
aaggacctga gggagcagat caatactcag aacaagaaag agttcttcga agaactgctg    3480
```

```
cgcctgctgc ggctcaccct gcaaatgagg aactccatgc caagttctga catcgactac    3540
ctgatcagcc cagtcgccaa cgacaccgga tgcttcttcg attcaagaaa gcaggccgag    3600
ctgaaagaga atgcagttct ccctatgaac gctgatgcta atggtgcata caacatcgct    3660
agaaagggac tgctggcaat ccgcaagatg aaacaagaag agaacgacag tgctaagatc    3720
agcctcgcta tatccaacaa ggagtggctc aagtttgctc agactaagcc atatctggag    3780
gac                                                                  3783

<210> SEQ ID NO 19
<211> LENGTH: 3666
<212> TYPE: DNA
<213> ORGANISM: Oribacterium sp.

<400> SEQUENCE: 19
atggagaccg agatcctgaa gtacgacttc ttcgagcgcg agggcaagta catgtactac      60
gacggcctga ccaagcagta cgccctgagc aagaccatcc gcaacgagct ggtgcccatc     120
ggcaagaccc tggacaacat caagaagaac cgcatcctgg aggccgacat caagcgcaag     180
agcgactacg agcacgtgaa gaagctgatg acatgtacc acaagaagat catcaacgag      240
gccctggaca acttcaagct gagcgtgctg gaggacgccg ccgacatcta cttcaacaag     300
cagaacgacg agcgcgacat cgacgccttc ctgaagatcc aggacaagct gcgcaaggag     360
atcgtggagc agctgaaggg ccacaccgac tacagcaagg tgggcaacaa ggacttcctg     420
ggcctgctga aggccgccag caccgaggag gaccgcatcc tgatcgagag cttcgacaac     480
ttctacacct acttcaccag ctacaacaag gtgcgcagca acctgtacag cgccgaggac     540
aagagcagca ccgtggccta ccgcctgatc aacgagaacc tgcccaagtt cttcgacaac     600
atcaaggcct accgcaccgt gcgcaacgcc ggcgtgatca cgcggcacat gagcatcgtg     660
gagcaggacg agctgttcga ggtggacacc ttcaaccaca ccctgaccca gtacggcatc     720
gacacctaca ccacatgat cggccagctg aacagcgcca tcaacctgta caaccagaag     780
atgcacggcg ccggcagctt caagaagctg cccaagatga aggagctgta caagcagctg     840
ctgaccgagc gcgaggagga gttcatcgag agtacaccg acgacgaggt gctgatcacc     900
agcgtgcaca actacgtgag ctacctgatc gactacctga acagcgacaa ggtggagagc     960
ttcttcgaca ccctgcgcaa gagcgacggc aaggaggtgt tcatcaagaa cgacgtgagc    1020
aagaccacca tgagcaacat cctgttcgac aactggagca ccatcgacga cctgatcaac    1080
cacgagtacg cagcgcccc cgagaacgtg aagaagacca aggacgacaa gtacttcgag    1140
aagcgccaga aggacctgaa gaagaacaag agctacagcc tgagcaagat cgccgccctg    1200
tgccgcgaca ccaccatcct ggagaagtac atccgccgcc tggtggacga catcgagaag    1260
atctacacca gcaacaacgt gttcagcgac atcgtgctga gcaagcacga ccgcagcaag    1320
aagctgagca gaacaccaa cgccgtgcag gccatcaaga acatgctgga cagcatcaag    1380
gacttcgagc acgacgtgat gctgatcaac ggcagcggcc aggagatcaa gaagaacctg    1440
aacgtgtaca gcgagcagga ggccctggcc ggcatcctgc gccaggtgga ccacatctac    1500
aacctgaccc gcaactacct gaccaagaag ccctcagca ccgagaagat caagctgaac    1560
ttcaaccgcc ccaccttcct ggacggctgg gacaagaaca aggaggaggc caacctgggc    1620
atcctgctga tcaaggacaa ccgctactac ctgggcatca tgaacaccag cagcaacaag    1680
gccttcgtga ccccccccaa ggccatcagc aacgacatct acaagaaggt ggactacaag    1740
ctgctgcccg gccccaacaa gatgctgccc aaggtgttct tcgccaccaa gaacatcgcc    1800
```

-continued

| | |
|---|---|
| tactacgccc ccagcgagga gctgctgagc aagtaccgca agggcaccca caagaagggc | 1860 |
| gacagcttca gcatcgacga ctgccgcaac ctgatcgact tcttcaagag cagcatcaac | 1920 |
| aagaacaccg actggagcac cttcggcttc aacttcagcg acaccaacag ctacaacgac | 1980 |
| atcagcgact tctaccgcga ggtggagaag cagggctaca agctgagctt caccgacatc | 2040 |
| gacgcctgct acatcaagga cctggtggac aacaacgagc tgtacctgtt ccagatctac | 2100 |
| aacaaggact tcagcccta cagcaagggc aagctgaacc tgcacaccct gtacttcaag | 2160 |
| atgctgttcg accagcgcaa cctggacaac gtggtgtaca agctgaacgg cgaggccgag | 2220 |
| gtgttctacc gccccgccag catcgagagc gacgagcaga tcatccacaa gagcggccag | 2280 |
| aacatcaaga caagaacca gaagcgcagc aactgcaaga agaccagcac cttcgactac | 2340 |
| gacatcgtga aggaccgccg ctactgcaag gacaagttca tgctgcacct gcccatcacc | 2400 |
| gtgaacttcg gcaccaacga gagcggcaag ttcaacgagc tggtgaacaa cgccatccgc | 2460 |
| gccgacaagg acgtgaacgt gatcggcatc gaccgcggcg agcgcaacct gctgtacgtg | 2520 |
| gtggtggtgg accccgcgg caagatcatc gagcagatca gcctgaacac catcgtggac | 2580 |
| aaggagtacg acatcgagac cgactaccac cagctgctgg acgagaagga gggcagccgc | 2640 |
| gacaaggccc gcaaggactg gaacaccatc gagaacatca aggagctgaa ggagggctac | 2700 |
| ctgagccagt ggtgaacat catcgccaag ctggtgctga agtacgacgc catcatctgc | 2760 |
| ctggaggacc tgaacttcgg cttcaagcgc ggccgccaga aggtggagaa gcaggtgtac | 2820 |
| cagaagttcg agaagatgct gatcgacaag atgaactacc tggtgctgga caagagccgc | 2880 |
| aagcaggaga gcccccagaa gcccggcggc gccctgaacg ccctgcagct gaccagcgcc | 2940 |
| ttcaagagct tcaaggagct gggcaagcag accggcatca tctactacgt gcccgcctac | 3000 |
| ctgaccagca agatcgaccc caccaccggc ttcgccaacc tgttctacat caagtacgag | 3060 |
| agcgtggaca ggcccgcga cttcttcagc aagttcgact tcatccgcta caaccagatg | 3120 |
| gacaactact tcgagttcgg cttcgactac aagagcttca ccgagcgcgc cagcggctgc | 3180 |
| aagagcaagt ggatcgcctg caccaacggc gagcgcatcg tgaagtaccg caacagcgac | 3240 |
| aagaacaaca gcttcgacga caagaccgtg atcctgaccg acgagtaccg cagcctgttc | 3300 |
| gacaagtacc tgcagaacta catcgacgag gacgacctga aggaccagat cctgcagatc | 3360 |
| gacagcgccg acttctacaa gaacctgatc aagctgttcc agctgaccct gcagatgcgc | 3420 |
| aacagcagca gcgacggcaa gcgcgactac atcatcagcc ccgtgaagaa ctaccgcgag | 3480 |
| gagttcttct gcagcgagtt cagcgacgac accttccccc gcgacgccga cgccaacggc | 3540 |
| gcctacaaca tcgcccgcaa gggcctgtgg gtgatcaagc agatccgcga gaccaagagc | 3600 |
| ggcaccaaga tcaacctggc catgagcaac agcgagtggc tggagtacgc ccagtgcaac | 3660 |
| ctgctg | 3666 |

```
<210> SEQ ID NO 20
<211> LENGTH: 3618
<212> TYPE: DNA
<213> ORGANISM: Butyrivibrio sp.

<400> SEQUENCE: 20
```

| | |
|---|---|
| atgtactacc agaacctgac caagaagtac cccgtgagca agaccatccg caacgagctg | 60 |
| atccccatcg gcaagaccct ggagaacatc cgcaagaaca acatcctgga gagcgacgtg | 120 |
| aagcgcaagc aggactacga gcacgtgaag ggcatcatgg acgagtacca caagcagctg | 180 |

-continued

```
atcaacgagg ccctggacaa ctacatgctg cccagcctga accaggccgc cgagatctac    240
ctgaagaagc acgtggacgt ggaggaccgc gaggagttca agaagaccca ggacctgctg    300
cgccgcgagg tgaccggccg cctgaaggag cacgagaact acaccaagat cggcaagaag    360
gacatcctgg acctgctgga aagctgccc agcatcagcg aggaggacta caacgccctg    420
gagagcttcc gcaacttcta cacctacttc accagctaca caaggtgcg cgagaacctg    480 tacagcgacg aggagaagag cagcaccgtg gcctaccgcc tgatcaacga gaacctgccc    540
aagttcctgg acaacatcaa gagctacgcc ttcgtgaagg ccgccggcgt gctggccgac    600
tgcatcgagg aggaggagca ggacgccctg ttcatggtgg agaccttcaa catgacccctg   660 acccaggagg gcatcgacat gtacaactac cagatcggca aggtgaacag cgccatcaac    720
ctgtacaacc agaagaacca caaggtggag gagttcaaga agatcccaa gatgaaggtg    780 ctgtacaagc agatcctgag cgaccgcgag gaggtgttca tcggcgagtt caaggacgac    840
gagaccctgc tgagcagcat cggcgcctac ggcaacgtgc tgatgaccta cctgaagagc    900
gagaagatca acatcttctt cgacgccctg cgcgagagcg agggcaagaa cgtgtacgtg    960
aagaacgacc tgagcaagac caccatgagc aacatcgtgt tcggcagctg gagcgccttc   1020
gacgagctgc tgaaccagga gtacgacctg gccaacgaga caagaagaa ggacgacaag   1080 tacttcgaga gcgccagaa ggagctgaag aagaacaaga gctacacccct ggagcagatg   1140 agcaacctga gcaaggagga catcagcccc atcgagaact acatcgagcg catcagcgag   1200
gacatcgaga agatctgcat ctacaacggc gagttcgaga agatcgtggt gaacgagcac   1260
gacagcagcc gcaagctgag caagaacatc aaggccgtga aggtgatcaa ggactacctg   1320
gacagcatca aggagctgga gcacgacatc aagctgatca acggcagcgg ccaggagctg   1380
gagaagaacc tggtggtgta cgtgggccag gaggaggccc tggagcagct gcgccccgtg   1440
gacagcctgt acaacctgac ccgcaactac ctgaccaaga gcccttcag caccgagaag   1500 gtgaagctga acttcaacaa gagcaccctg ctgaacggct gggacaagaa caaggagacc   1560
gacaacctgg gcatcctgtt cttcaaggac ggcaagtact acctgggcat catgaacacc   1620
accgccaaca aggccttcgt gaaccccccc gccgccaaga ccgagaacgt gttcaagaag   1680
gtggactaca gctgctgcc cggcagcaac aagatgctgc caaggtgtt cttcgccaag   1740 agcaacatcg ctactacaa ccccagcacc gagctgtaca gcaactacaa gaagggcacc   1800
cacaagaagg cccccagctt cagcatcgac gactgccaca acctgatcga cttcttcaag   1860
gagagcatca gaagcacga ggactggagc aagttcggct tcgagttcag cgacaccgcc   1920
gactaccgcg acatcagcga gttctaccgc gaggtgagaa gcagggcta caagctgacc   1980 ttcaccgaca tcgacgagag ctacatcaac gacctgatcg agaagaacga gctgtacctg   2040
ttccagatct acaacaagga cttcagcgag tacagcaagg gcaagctgaa cctgcacacc   2100
ctgtacttca tgatgctgtt cgaccagcgc aacctggaca cgtggtgta caagctgaac   2160 ggcgaggccg aggtgttcta ccgccccgcc agcatcgccg agaacgagct ggtgatccac   2220
aaggccggcg agggcatcaa gaacaagaac cccaaccgcg ccaaggtgaa ggagaccagc   2280
accttcagct acgacatcgt gaaggacaag cgctacagca gtacaagtt caccctgcac   2340 atccccatca ccatgaactt cggcgtggac gaggtgcgcc gcttcaacga cgtgatcaac   2400
aacgccctgc gcaccgacga caacgtgaac gtgatcggca tcgaccgcgg cgagcgcaac   2460
ctgctgtacg tggtggtgat caacagcgag ggcaagatcc tggagcagat cagcctgaac   2520
agcatcatca acaaggagta cgacatcgag accaactacc acgccctgct ggacgagcgc   2580
```

```
gaggacgacc gcaacaaggc ccgcaaggac tggaacacca tcgagaacat caaggagctg    2640
aagaccggct acctgagcca ggtggtgaac gtggtggcca agctggtgct gaagtacaac    2700
gccatcatct gcctggagga cctgaacttc ggcttcaagc gcggccgcca gaaggtggag    2760
aagcaggtgt accagaagtt cgagaagatg ctgatcgaga agctgaacta cctggtgatc    2820
gacaagagcc gcgagcaggt gagccccgag aagatgggcg cgccctgaa cgccctgcag    2880 ctgaccagca agttcaagag cttcgccgag ctgggcaagc agagcggcat catctactac    2940
gtgcccgcct acctgaccag caagatcgac cccaccaccg gcttcgtgaa cctgttctac    3000
atcaagtacg agaacatcga agaggccaag cagttcttcg acggcttcga cttcatccgc    3060
ttcaacaaga aggacgacat gttcgagttc agcttcgact acaagagctt cacccagaag    3120
gcctgcggca tccgcagcaa gtggatcgtg tacaccaacg gcgagcgcat catcaagtac    3180
cccaaccccg agaagaacaa cctgttcgac gagaaggtga tcaacgtgac cgacgagatc    3240
aagggcctgt tcaagcagta ccgcatcccc tacgagaacg gcgaggacat caaggagatc    3300
atcatcagca aggccgaggc cgacttctac aagcgcctgt tccgcctgct gcaccagacc    3360
ctgcagatgc gcaacagcac cagcgacggc acccgcgact acatcatcag ccccgtgaag    3420
aacgaccgcg gcgagttctt ctgcagcgag ttcagcgagg gcaccatgcc caaggacgcc    3480
gacgccaacg gcgcctacaa catcgcccgc aagggcctgt gggtgctgga gcagatccgc    3540
cagaaggacg agggcgagaa ggtgaacctg agcatgacca cgccgagtg gctgaagtac    3600 gcccagctgc acctgctg                                                 3618

<210> SEQ ID NO 21
<211> LENGTH: 3459
<212> TYPE: DNA
<213> ORGANISM: Proteocatella sphenisci

<400> SEQUENCE: 21
gagaacttca agaacctgta ccccatcaac aagaccctgc gcttcgagct gcgcccctac      60
ggcaagaccc tggagaactt caagaagagc ggcctgctgg agaaggacgc cttcaaggcc     120
aacagccgcc gcagcatgca ggccatcatc gacgagaagt tcaaggagac catcgaggag     180
cgcctgaagt acaccgagtt cagcgagtgc gacctgggca acatgaccag caaggacaag     240
aagatcaccg acaaggccgc caccaacctg aagaagcagg tgatcctgag cttcgacgac     300
gagatcttca caactacct gaagcccgac aagaacatcg acgccctgtt caagaacgac     360
cccagcaacc ccgtgatcag caccttcaag ggcttccacc cctacttcgt gaacttcttc     420
gagatccgca gcacatctt caagggcgag agcagcggca gcatggccta ccgcatcatc     480
gacgagaacc tgaccaccta cctgaacaac atcgagaaga tcaagaagct gcccgaggag     540
ctgaagagcc agctggaggg catcgaccag atcgacaagc tgaacaacta caacgagttc     600
atcacccaga gcggcatcac ccactacaac gagatcatcg cggcatcag caagagcgag     660 aacgtgaaga tccagggcat caacgagggc atcaacctgt actgccagaa gaacaaggtg     720
aagctgcccc gcctgacccc cctgtacaag atgatcctga cgaccgcgt gagcaacagc     780 ttcgtgctgg acaccatcga gaacgacacc gagctgatcg agatgatcag cgacctgatc     840
aacaagaccg agatcagcca ggacgtgatc atgagcgaca tccagaacat cttcatcaag     900
tacaagcagc tgggcaacct gcccggcatc agctacagca gcatcgtgaa cgccatctgc     960
agcgactacg acaacaactt cggcgacggc aagcgcaaga gagctacga gaacgaccgc    1020
```

```
aagaagcacc tggagaccaa cgtgtacagc atcaactaca tcagcgagct gctgaccgac    1080
accgacgtga gcagcaacat caagatgcgc tacaaggagc tggagcagaa ctaccaggtg    1140
tgcaaggaga acttcaacgc caccaactgg atgaacatca agaacatcaa gcagagcgag    1200
aagaccaacc tgatcaagga cctgctggac atcctgaaga gcatccagcg cttctacgac    1260
ctgttcgaca tcgtggacga ggacaagaac cccagcgccg agttctacac ctggctgagc    1320
aagaacgccg agaagcttga cttcgagttc aacagcgtgt acaacaagag ccgcaactac    1380
ctgacccgca agcagtacag cgacaagaag atcaagctga cttcgacag ccccacccctg    1440
gccaagggct gggacgccaa caaggagatc gacaacagca ccatcatcat gcgcaagttc    1500
aacaacgacc gcggcgacta cgactacttc ctgggcatct ggaacaagag cacccccgcc    1560
aacgagaaga tcatcccccct ggaggacaac ggcctgttcg agaagatgca gtacaagctg    1620
taccccgacc ccagcaagat gctgcccaag cagttcctga gcaagatctg gaaggccaag    1680
caccccacca ccccgagtt cgacaagaag tacaaggagg ccgccacaa gaagggcccc    1740
gacttcgaga aggagttcct gcacgagctg atcgactgct tcaagcacgg cctggtgaac    1800
cacgacgaga agtaccagga cgtgttcggc ttcaacctgc gcaacaccga ggactacaac    1860
agctacaccg agttcctgga ggacgtggag cgctgcaact acaacctgag cttcaacaag    1920
atcgccgaca ccagcaacct gatcaacgac ggcaagctgt acgtgttcca gatctggagc    1980
aaggacttca gcatcgacag caagggcacc aagaacctga acaccatcta cttcgagagc    2040
ctgttcagcg aggagaacat gatcgagaag atgttcaagc tgagcggcga ggccgagatc    2100
ttctaccgcc ccgccagcct gaactactgc gaggacatca tcaagaaggg ccaccaccac    2160
gccgagctga aggacaagtt cgactacccc atcatcaagg acaagcgcta cagccaggac    2220
aagttcttct tccacgtgcc catggtgatc aactacaaga gcgagaagct gaacagcaag    2280
agcctgaaca accgcaccaa cgagaacctg gccagttca cccacatcat cggcatcgac    2340
cgcggcgagc gccacctgat ctacctgacc gtggtggacg tgagcaccgg cgagatcgtg    2400
gagcagaagc acctggacga gatcatcaac accgacacca agggcgtgga gcacaagacc    2460
cactacctga acaagctgga ggagaagagc aagacccgcg acaacgagcg caagagctgg    2520
gaggccatcg agaccatcaa ggagctgaag gagggctaca tcagccacgt gatcaacgag    2580
atccagaagc tgcaggagaa gtacaacgcc ctgatcgtga tggagaacct gaactacggc    2640
ttcaagaaca gccgcatcaa ggtggagaag caggtgtacc agaagttcga gaccgccctg    2700
atcaagaagt tcaactacat catcgacaag aaggaccccg agacctacat ccacggctac    2760
cagctgacca accccatcac caccctggac aagatcggca accagagcgg catcgtgctg    2820
tacatccccg cctggaacac cagcaagatc gaccccgtga ccggcttcgt gaacctgctg    2880
tacgccgacg acctgaagta caagaaccag gagcaggcca agagcttcat ccagaagatc    2940
gacaacatct acttcgagaa cggcgagttc aagttcgaca tcgacttcag caagtggaac    3000
aaccgctaca gcatcagcaa gaccaagtgg accctgacca gctacggcac ccgcatccag    3060
accttccgca accccagaa gaacaacaag tgggacagcg ccgagtacga cctgaccgag    3120
gagttcaagc tgatcctgaa catcgacggc accctgaaga gccaggacgt ggagacctac    3180
aagaagttca tgagcctgtt caagctgatg ctgcagctgc gcaacagcgt gaccggcacc    3240
gacatcgact acatgatcag ccccgtgacc gacaagaccg gcacccactt cgacagccgc    3300
gagaacatca agaacctgcc cgccgacgcc gacgccaacg gcgcctacaa catcgcccgc    3360
aagggcatca tggccatcga gaacatcatg aacggcatca gcgacccct gaagatcagc    3420
```
aacgaggact acctgaagta catccagaac cagcaggag       3459

<210> SEQ ID NO 22
<211> LENGTH: 3642
<212> TYPE: DNA
<213> ORGANISM: Candidatus Dojkabacteria

<400> SEQUENCE: 22
atgaagaacg tgttcggcgg cttcaccaac ctgtacagcc tgaccaagac cctgcgcttc       60
gagctgaagc ccaccagcaa gacccagaag ctgatgaagc gcaacaacgt gatccagacc      120
gacgaggaga tcgacaagct gtaccacgac gagatgaagc ccatcctgga cgagatccac      180
cgccgcttca tcaacgacgc cctggcccag aagatcttca tcagcgccag cctggacaac      240
ttcctgaagg tggtgaagaa ctacaaggtg gagagcgcca agaagaacat caagcagaac      300
caggtgaagc tgctgcagaa ggagatcacc atcaagaccc tgggcctgcg ccgcgaggtg      360
gtgagcggct tcatcaccgt gagcaagaag tggaaggaca gtacgtgggc cctgggcatc      420
aagctgaagg gcgacggcta caaggtgctg accgagcagg ccgtgctgga catcctgaag      480
atcgagttcc ccaacaaggc caagtacatc gacaagttcc gcggcttctg gacctacttc      540
agcggcttca acgagaaccg caagaactac tacagcgagg aggacaaggc caccagcatc      600
gccaaccgca tcgtgaacga gaacctgagc cgctacatcg acaacatcat cgccttcgag      660
gagatcctgc agaagatccc caacctgaag aagttcaagc aggacctgga catcaccagc      720
tacaactact acctgaacca ggccggcatc gacaagtaca acaagatcat cggcggctac      780
atcgtggaca aggacaagaa gatccagggc atcaacgaga aggtgaacct gtacacccag      840
cagaccaaga agaagctgcc caagctgaag ttcctgttca gcagatcgg cagcgagcgc      900
aagggcttcg gcatcttcga gatcaaggag ggcaaggagt gggagcagct gggcgacctg      960
ttcaagctgc agcgcaccaa gatcaacagc aacggccgcg agaagggcct gttcgacagc     1020
ctgcgcacca tgtaccgcga gttcttcgac gagatcaagc gcgacagcaa cagccaggcc     1080
cgctacagcc tggacaagat ctacttcaac aaggccagcg tgaacaccat cagcaacagc     1140
tggttcacca actggaacaa gttcgccgag ctgctgaaca tcaaggagga caagaagaac     1200
ggcgagaaga agatccccga gcagatcagc atcgaggaca tcaaggacag cctgagcatc     1260
atccccaagg agaacctgga ggagctgttc aagctgacca ccgcgagaa gcacgaccgc     1320
acccgcttct tcggcagcaa cgcctgggtg accttcctga acatctggca gaacgagatc     1380
gaggagagct tcaacaagct ggaggagaag gagaaggact tcaagaagaa cgccgccatc     1440
aagttccaga gaacaacct ggtgcagaag aactacatca aggaggtgtg cgaccgcatg     1500
ctggccatcg agcgcatggc caagtaccac ctgcccaagg acagcaacct gagccgcgag     1560
gaggacttct actggatcat cgacaacctg agcgagcagc gcgagatcta caagtactac     1620
aacgccttcc gcaactacat cagcaagaag ccctacaaca agagcaagat gaagctgaac     1680
ttcgagaacg gcaacctgct gggcggctgg agcgacggcc aggagcgcaa caaggccggc     1740
gtgatcctgc gcaacggcaa caagtactac ctgggcgtgc tgatcaaccg cggcatcttc     1800
cgcaccgaca agatcaacaa cgagatctac cgcaccggca gcagcaagtg ggagcgcctg     1860
atcctgagca acctgaagtt ccagacccg gccggcaagg gcttcctggg caagcacggc     1920
gtgagctacg gcaacatgaa ccccgagaag agcgtgccca gcctgcagaa gttcatccgc     1980
gagaactacc tgaagaagta ccccccagctg accgaggtga gcaacaccaa gttcctgagc     2040

```
aagaaggact tcgacgccgc catcaaggag ccctgaagg agtgcttcac catgaacttc    2100
atcaacatcg ccgagaacaa gctgctggag gccgaggaca agggcgacct gtacctgttc    2160
gagatcacca acaaggactt cagcggcaag aagagcggca aggacaacat ccacaccatc    2220
tactggaagt acctgttcag cgagagcaac tgcaagagcc ccatcatcgg cctgaacggc    2280
ggcgccgaga tcttcttccg cgagggccag aaggacaagc tgcacaccaa gctggacaag    2340
aagggcaaga aggtgttcga cgccaagcgc tacagcgagg acaagctgtt cttccacgtg    2400
agcatcacca tcaactacgg caagcccaag aacatcaagt ccgcgacat catcaaccag    2460 ctgatcacca gcatgaacgt gaacatcatc ggcatcgacc gcggcgagaa gcacctgctg    2520
tactacagcg tgatcgacag caacggcatc atcctgaagc agggcagcct gaacaagatc    2580
cgcgtgggcg acaaggaggt ggacttcaac aagaagctga ccgagcgcgc caacgagatg    2640
aagaaggccc gccagagctg ggagcagatc ggcaacatca gaacttcaa ggagggctac    2700 ctgagccagg ccatccacga gatctaccag ctgatgatca agtacaacgc catcatcgtg    2760
ctggaggacc tgaacaccga gttcaaggcc aagcgcctga gcaaggtgga agagagcgtg    2820
tacaagaagt tcgagctgaa gctggcccgc aagctgaacc acctgatcct gaaggaccgc    2880
aacaccaacg agatcggcgg cgtgctgaag gcctaccagc tgaccccac catcggcggc    2940 ggcgacgtga gcaagttcga gaaggccaag cagtgggca tgatgttcta cgtgcgcgcc    3000
aactacacca gcaccaccga ccccgtgacc ggctggcgca gcacctgta catcagcaac    3060 ttcagcaaca acagcgtgat caagagcttc ttcgacccca ccaaccgcga caccggcatc    3120
gagatcttct acagcggcaa gtaccgcagc tgggcttcc gctacgtgca gaaggagacc    3180
ggcaagaagt gggagctgtt cgccaccaag gagctggagc gcttcaagta caaccagacc    3240
accaagctgt gcgagaagat caacctgtac gacaagttcg aggagctgtt caagggcatc    3300
gacaagagcg ccgacatcta cagccagctg tgcaacgtgc tggacttccg ctggaagagc    3360
ctggtgtacc tgtggaacct gctgaaccag atccgcaacg tggacaagaa cgccgagggc    3420
aacaagaacg acttcatcca gagccccgtg tacccttct tcgacagccg caagaccgac    3480
ggcaagaccg agcccatcaa cggcgacgcc aacggcgccc tgaacatcgc ccgcaagggc    3540
ctgatgctgg tggagcgcat caagaacaac cccgagaagt acgagcagct gatccgcgac    3600
accgagtggg acgcctggat ccagaacttc aacaaggtga ac                       3642
```

<210> SEQ ID NO 23
<211> LENGTH: 3645
<212> TYPE: DNA
<213> ORGANISM: Pseudobutyrivibrio xylanivorans

<400> SEQUENCE: 23

```
atgatcatcg ccgcgactt caacatgtac taccagaacc tgaccaagat gtaccccatc     60
agcaagaccc tgcgcaacga gctgatcccc gtgggcaaga ccctggagaa catccgcaag    120
aacggcatcc tggaggccga catccagcgc aaggccgact acgagcacgt gaagaagctg    180
atggacaact accacaagca gctgatcaac gaggccctgc agggcgtgca cctgagcgac    240
ctgagcgacg cctacgacct gtacttcaac ctgagcaagg agaagaacag cgtgacgcc    300 ttcagcaagt gccaggacaa gctgcgcaag gagatcgtga gcttcctgaa gaaccacgag    360
aacttcccca gatcggcaa caaggagatc atcaagctga tccagagcct gaacgacaac    420
gacgccgaca caacgccct ggacagcttc agcaacttct acacctactt cagcagctac    480
aacgaggtgc gcaagaacct gtacagcgac gaggagaaga gcagcaccgt ggcctaccgc    540
```

```
ctgatcaacg agaacctgcc caagagcctg acaacatca aggcctacgc catcgccaag      600
aaggccggcg tgcgcgccga gggcctgagc gaggaggagc aggactgcct gttcatcatc      660
gagaccttcg agcgcaccct gacccaggac ggcatcgaca actacaacgc cgacatcggc      720
aagctgaaca ccgccatcaa cctgtacaac cagcagaaca gaagcagga gggcttccgc       780 aaggtgcccc agatgaagtg cctgtacaag cagatcctga cgaccgcga ggaggccttc       840 atcgacgagt tcagcgacga cgaggacctg atcaccaaca tcgagagctt cgccgagaac      900
atgaacgtgt tcctgaacag cgagatcatc accgacttca gaacgccct ggtggagagc       960 gacggcagcc tggtgtacat caagaacgac gtgagcaaga ccctgttcag caacatcgtg     1020
ttcggcagct ggaacgccat cgacgagaag ctgagcgacg agtacgacct ggccaacagc     1080
aagaagaaga aggacgagaa gtactacgag aagcgccaga aggagctgaa gaagaacaag     1140
agctacgacc tggagaccat catcggcctg ttcgacgaca gcatcgacgt gatcggcaag     1200
tacatcgaga agctggagag cgacatcacc gccatcgccg aggccaagaa cgacttcgac     1260
gagatcgtgc tgcgcaagca cgacaagaac aagagcctgc gcaagaacac caacgccgtg     1320
gaggccatca gagctacct ggacaccgtg aaggacttcg agcgcgacat caagctgatc      1380
aacggcagcg ccaggaggt ggagaagaac ctggtggtgt acgccgagca ggagaacatc      1440
ctggccgaga tcaagaacgt ggacagcctg tacaacatga gcgcaacta cctgaccag       1500 aagcccttca gcaccgagaa gttcaagctg aacttcgaga cccccaccct gctgaacggc     1560
tgggaccgca acaaggagaa ggactacctg ggcatcctgt tcgagaagga gggcatgtac     1620
tacctgggca tcatcaacaa caaccaccgc aagatcttcg agaacgagaa gctgtgcacc     1680
ggcaaggaga gctgcttcaa caagatcgtg tacaagcaga tcagcaacgc cgccaagtac     1740
ctgagcagca agcagatcaa ccccccagaac ccccccaagg agatcgccga gatcctgctg     1800
aagcgcaagg ccgacagcag cagcctgagc cgcaaggaga ccgagctgtt catcgactac     1860
ctgaaggacg acttcctggt gaactacccc atgatcatca cagcgacgg cgagaacttc      1920 ttcaacttcc acttcaagca ggccaaggac tacggcagcc tgcaggagtt cttcaaggag     1980
gtggagcacc aggcctacag cctgaagacc cgccccatcg acgacagcta catctaccgc     2040
atgatcgacg agggcaagct gtacctgttc cagatccaca caaggacttt cagcccctac    2100
agcaagggca acctgaacct gcacaccatc tacctgcaga tgctgttcga ccagcgcaac     2160
ctgaacaacg tggtgtacaa gctgaacggc gaggccgagg tgttctaccg ccccgccagc     2220
atcaacgacg aggaggtgat catccacaag gccggcgagg agatcaagaa caagaacagc     2280
aagcgcgccg tggacaagcc caccagcaag ttcggctacg acatcatcaa ggaccgccgc     2340
tacagcaagg acaagttcat gctgcacatc cccgtgacca tgaacttcgg cgtggacgag     2400
acccgccgct tcaacgacgt ggtgaacgac gccctgcgca cgacgagaa ggtgcgcgtg      2460 atcggcatcg accgcggcga gcgcaacctg ctgtacgtgg tggtggtgga caccgacggc     2520
accatcctgg agcagatcag cctgaacagc atcatcaaca acgagtacag catcgagacc     2580
gactaccaca gctgctgga cgagaaggag ggcgaccgcg accgcgcccg caagaactgg      2640
accaccatcg agaacatcaa ggagctgaag gagggctacc tgagccaggt ggtgaacgtg     2700
atcgccaagc tggtgctgaa gtacaacgcc atcatctgcc tggaggacct gaacttcggc     2760
ttcaagcgcg gccgccagaa ggtggagaag caggtgtacc agaagttcga gaagatgctg     2820
atcgacaagc tgaactacct ggtgatcgac aagagccgca agcaggagaa gcccgaggag     2880
```

```
ttcggcggcg ccctgaacgc cctgcagctg accagcaagt tcaccagctt caaggacatg    2940
ggcaagcaga ccggcatcat ctactacgtg cccgcctacc tgaccagcaa gatcgacccc    3000
accaccggct tcgccaacct gttctacgtg aagtacgaga acgtggagaa ggccaaggag    3060
ttcttcagcc gcttcgacag catcagctac aacaacgaga gcggctactt cgagttcgcc    3120
ttcgactaca agaagttcac cgaccgcgcc tgcggcgccc gcagccagtg gaccgtgtgc    3180
acctacggcg agcgcatcat caagtaccgc aacgccgaca gaacaacag cttcgacgac     3240 aagaccatcg tgctgagcga ggagttcaag gagctgttca gcatctacgg catcagctac    3300
gaggacggcg ccgagctgaa gaacaagatc atgagcgtgg acgaggccga cttcttccgc    3360
tgcctgaccg gcctgctgca gaagaccctg cagatgcgca acagcagcaa cgacggcacc    3420
cgcgactaca tcatcagccc catcatgaac gaccgcggcg agttcttcaa cagcgaggcc    3480
tgcgacgcca gcaagcccaa ggacgccgac gccaacggcc ccttcaacat cgcccgcaag    3540
ggcctgtggg tgctggagca gatccgcaac acccccagcg cgacaagct gaacctggcc     3600 atgagcaacg ccgagtggct ggagtacgcc cagcgcaacc agatc                    3645

<210> SEQ ID NO 24
<211> LENGTH: 3639
<212> TYPE: DNA
<213> ORGANISM: Pseudobutyrivibrio ruminis

<400> SEQUENCE: 24
atgatcatcg gccgcgactt caacatgtac taccagaacc tgaccaagat gtaccccatc    60
agcaagaccc tgcgcaacga gctgatcccc gtgggcaaga ccctggagaa catccgcaag    120
aacggcatcc tggaggccga catccagcgc aaggccgact acgagcacgt gaagaagctg    180
atggacaact accacaagca gctgatcaac gaggccctgc agggcgtgca cctgagcgac    240
ctgagcgacg cctacgacct gtacttcaac ctgagcaagg agaagaacag cgtggacgcc    300
ttcagcaagt gccaggacaa gctgcgcaag gagatcgtga gcctgctgaa gaaccacgag    360 aacttccccca gatcggcaa caaggagatc atcaagctgc tgcagagcct gtacgacaac    420
gacaccgact acaaggccct ggacagcttc agcaacttct acacctactt cagcagctac    480
aacgaggtgc gcaagaacct gtacagcgac gaggagaaga gcagcaccgt ggcctaccgc    540
ctgatcaacg agaacctgcc caagttcctg gacaacatca aggcctacgc catcgccaag    600
aaggccggcg tgcgcgccga gggcctgagc gaggaggacc aggactgcct gttcatcatc    660
gagaccttcg agcgcaccct gacccaggac ggcatcgaca actacaacgc cgccatcggc    720
aagctgaaca ccgccatcaa cctgttcaac cagcagaaca gaagcagga gggcttccgc     780 aaggtgcccc agatgaagtg cctgtacaag cagatcctga cgaccgcga ggaggccttc     840 atcgacgagt tcagcgacga cgaggacctg atcaccaaca tcgagagctt cgccgagaac    900
atgaacgtgt tcctgaacag cgagatcatc accgacttca agatcgccct ggtggagagc    960
gacggcagcc tggtgtacat caagaacgac gtgagcaaga ccagcttcag caacatcgtg    1020
ttcggcagct ggaacgccat cgacgagaag ctgagcgacg agtacgacct ggccaacagc    1080
aagaagaaga aggacgagaa gtactacgag aagcgccaga aggagctgaa gaagaacaag    1140
agctacgacc tggagaccat catcggcctg ttcgacgaca cagcgacgt gatcggcaag    1200 tacatcgaga agctggagag cgacatcacc gccatcgccg aggccaagaa cgacttcgac    1260
gagatcgtgc tgcgcaagca cgacaagaac aagagcctgc gcaagaacac caacgccgtg    1320
gaggccatca agagctacct ggacaccgtg aaggacttcg agcgcgacat caagctgatc    1380
```

```
aacggcagcg gccaggaggt ggagaagaac ctggtggtgt acgccgagca ggagaacatc    1440
ctggccgaga tcaagaacgt ggacagcctg tacaacatga gccgcaacta cctgacccag    1500
aagcccttca gcaccgagaa gttcaagctg aacttcaacc gcgccaccct gctgaacggc    1560
tgggacaaga caaggagac cgacaacctg ggcatcctgt tcgagaagga cggcatgtac    1620
tacctgggca tcatgaacac caaggccaac aagatcttcg tgaacatccc caaggccacc    1680
agcaacgacg tgtaccacaa ggtgaactac aagctgctgc ccggcccaa caagatgctg    1740 cccaaggtgt tcttcgccca gagcaacctg gactactaca gcccagcga ggagctgctg    1800 gccaagtaca aggccggcac ccacaagaag ggcgacaact tcagcctgga ggactgccac    1860
gccctgatcg acttcttcaa ggccagcatc gagaagcacc ccgactggag cagcttcggc    1920
ttcgagttca gcgagacctg cacctacgag gacctgagcg gcttctaccg cgaggtggag    1980
aagcagggct acaagatcac ctacaccgac gtggacgccg actacatcac cagcctggtg    2040
gagcgcgacg agctgtacct gttccagatc tacaacaagg acttcagccc ctacagcaag    2100
ggcaacctga acctgcacac catctacctg cagatgctgt tcgaccagcg caacctgaac    2160
aacgtggtgt acaagctgaa cggcgaggcc gaggtgttct accgccccgc cagcatcaac    2220
gacgaggagg tgatcatcca aaggccggc gaggagatca agaacaagaa cagcaagcgc    2280
gccgtggaca gcccaccag caagttcggc tacgacatca tcaaggaccg ccgctacagc    2340
aaggacaagt tcatgctgca catccccgtg accatgaact tcggcgtgga cgagacccgc    2400
cgcttcaacg acgtggtgaa cgacgccctg cgcaacgacg agaaggtgcg cgtgatcggc    2460
atcgaccgcg gcgagcgcaa cctgctgtac gtggtggtgg tggacaccga cggcaccatc    2520
ctggagcaga tcagcctgaa cagcatcatc aacaacgagt acagcatcga gaccgactac    2580
cacaagctgc tggacgagaa gggaggcgac cgcgaccgcg cccgcaagaa ctggaccacc    2640
atcgagaaca tcaaggagct gaaggagggc tacctgagcc aggtggtgaa cgtgatcgcc    2700
aagctggtgc tgaagtacaa cgccatcatc tgcctggagg acctgaactt cggcttcaag    2760
cgcggccgcc agaaggtgga gaagcaggtg taccagaagt tcgagaagat gctgatcgac    2820
aagctgaact acctggtgat cgacaagagc cgcaagcagg acaagcccga ggagttcggc    2880
ggcgccctga cgccctgca gctgaccagc aagttcacca gcttcaagga catgggcaag    2940
cagaccggca tcatctacta cgtgcccgcc tacctgacca gcaagatcga ccccaccacc    3000
ggcttcgcca acctgttcta cgtgaagtac gagaacgtgg agaaggccaa ggagttcttc    3060
agccgcttcg acagcatcag ctacaacaac gagagcggct acttcgagtt cgccttcgac    3120
tacaagaagt tcaccgaccg cgcctgcggc gcccgcagcc agtggaccgt gtgcacctac    3180
ggcgagcgca tcatcaagtt ccgcaacacc gagaagaaca cagcttcga cgacaagacc    3240 atcgtgctga gcgaggagtt caaggagctg ttcagcatct acggcatcag ctacgaggac    3300
ggcgccgagc tgaagaacaa gatcatgagc gtggacgagg ccgacttctt ccgcagcctg    3360
acccgcctgt tccagcagac catgcagatg cgcaacagca gcaacgacgt gacccgcgac    3420
tacatcatca gccccatcat gaacgaccgc ggcgagttct tcaacagcga ggcctgcgac    3480
gccagcaagc ccaaggacgc cgacgccaac ggcgcctcca catcgcccg caagggcctg    3540 tgggtgctgg agcagatccg caacaccccc agcggcgaca agctgaacct ggccatgagc    3600
aacgccgagt ggctggagta cgcccagcgc aaccagatc                          3639

<210> SEQ ID NO 25
```

```
<211> LENGTH: 18
<212> TYPE: DNA
<213> ORGANISM: artificial sequence
<220> FEATURE:
<223> OTHER INFORMATION: crRNA1 scaffold sequence

<400> SEQUENCE: 25
atttctactg ttgtagat                                                 18

<210> SEQ ID NO 26
<211> LENGTH: 18
<212> TYPE: DNA
<213> ORGANISM: artificial sequence
<220> FEATURE:
<223> OTHER INFORMATION: crRNA2 scaffold sequence

<400> SEQUENCE: 26
atttctacta ttgtagat                                                 18

<210> SEQ ID NO 27
<211> LENGTH: 18
<212> TYPE: DNA
<213> ORGANISM: artificial sequence
<220> FEATURE:
<223> OTHER INFORMATION: crRNA3 scaffold sequence

<400> SEQUENCE: 27
atttctacta ctgtagat                                                 18

<210> SEQ ID NO 28
<211> LENGTH: 18
<212> TYPE: DNA
<213> ORGANISM: artificial sequence
<220> FEATURE:
<223> OTHER INFORMATION: crRNA4 scaffold sequence

<400> SEQUENCE: 28
atttctactt tggtagat                                                 18

<210> SEQ ID NO 29
<211> LENGTH: 19
<212> TYPE: DNA
<213> ORGANISM: artificial sequence
<220> FEATURE:
<223> OTHER INFORMATION: crRNA5 scaffold sequence

<400> SEQUENCE: 29
atttctacta gttgtagat                                                19

<210> SEQ ID NO 30
<211> LENGTH: 18
<212> TYPE: DNA
<213> ORGANISM: artificial sequence
<220> FEATURE:
<223> OTHER INFORMATION: crRNA31 scaffold sequence

<400> SEQUENCE: 30
atttctacta tggtagat                                                 18

<210> SEQ ID NO 31
<211> LENGTH: 18
<212> TYPE: DNA
<213> ORGANISM: artificial sequence
<220> FEATURE:
<223> OTHER INFORMATION: crRNA77 scaffold sequence

<400> SEQUENCE: 31
```

-continued

```
atttctactg tcgtagat                                              18

<210> SEQ ID NO 32
<211> LENGTH: 18
<212> TYPE: DNA
<213> ORGANISM: artificial sequence
<220> FEATURE:
<223> OTHER INFORMATION: crRNA129 scaffold sequence

<400> SEQUENCE: 32
atttctactt gtgtagat                                              18

<210> SEQ ID NO 33
<211> LENGTH: 18
<212> TYPE: DNA
<213> ORGANISM: artificial sequence
<220> FEATURE:
<223> OTHER INFORMATION: crRNA159 scaffold sequence

<400> SEQUENCE: 33
atttctactg tggtagat                                              18

<210> SEQ ID NO 34
<211> LENGTH: 36
<212> TYPE: DNA
<213> ORGANISM: Artificial Sequence
<220> FEATURE:
<223> OTHER INFORMATION: sequencing result

<400> SEQUENCE: 34
gtctaaaagc ctttaataat ttctactgtt gtagat                          36

<210> SEQ ID NO 35
<211> LENGTH: 36
<212> TYPE: DNA
<213> ORGANISM: Artificial Sequence
<220> FEATURE:
<223> OTHER INFORMATION: sequencing result

<400> SEQUENCE: 35
gttaagtaat atagaataat ttctactgtt gtagat                          36

<210> SEQ ID NO 36
<211> LENGTH: 36
<212> TYPE: DNA
<213> ORGANISM: Artificial Sequence
<220> FEATURE:
<223> OTHER INFORMATION: sequencing result

<400> SEQUENCE: 36
gttaagtaac ctaaataatt tctactgtgt gtagat                          36

<210> SEQ ID NO 37
<211> LENGTH: 36
<212> TYPE: DNA
<213> ORGANISM: Artificial Sequence
<220> FEATURE:
<223> OTHER INFORMATION: sequencing result

<400> SEQUENCE: 37
gtctaaaact cattcagaat ttctactagt gtagat                          36

<210> SEQ ID NO 38
<211> LENGTH: 36
<212> TYPE: DNA
```

<213> ORGANISM: Artificial Sequence
<220> FEATURE:
<223> OTHER INFORMATION: sequencing result

<400> SEQUENCE: 38
atttgaaagc atctttaat ttctactatt gtagat    36

<210> SEQ ID NO 39
<211> LENGTH: 36
<212> TYPE: DNA
<213> ORGANISM: Artificial Sequence
<220> FEATURE:
<223> OTHER INFORMATION: sequencing result

<400> SEQUENCE: 39
ctttaagaga tactattaat ttctactatt gtagat    36

<210> SEQ ID NO 40
<211> LENGTH: 36
<212> TYPE: DNA
<213> ORGANISM: Artificial Sequence
<220> FEATURE:
<223> OTHER INFORMATION: sequencing result

<400> SEQUENCE: 40
gccaaatacc tctataaaat ttctactttt gtagat    36

<210> SEQ ID NO 41
<211> LENGTH: 36
<212> TYPE: DNA
<213> ORGANISM: Artificial Sequence
<220> FEATURE:
<223> OTHER INFORMATION: sequencing result

<400> SEQUENCE: 41
ctctacaact gataaagaat ttctactttt gtagat    36

<210> SEQ ID NO 42
<211> LENGTH: 36
<212> TYPE: DNA
<213> ORGANISM: Artificial Sequence
<220> FEATURE:
<223> OTHER INFORMATION: sequencing result

<400> SEQUENCE: 42
ctctaaaacc cccaacaaat ttctactttt gtagat    36

<210> SEQ ID NO 43
<211> LENGTH: 36
<212> TYPE: DNA
<213> ORGANISM: Artificial Sequence
<220> FEATURE:
<223> OTHER INFORMATION: sequencing result

<400> SEQUENCE: 43
ctctacaact gataaagaat ttctactttt gtagat    36

<210> SEQ ID NO 44
<211> LENGTH: 36
<212> TYPE: DNA
<213> ORGANISM: Artificial Sequence
<220> FEATURE:
<223> OTHER INFORMATION: sequencing result

<400> SEQUENCE: 44
gtctagacgt tactattaat ttctactgtt gtagat    36

<210> SEQ ID NO 45
<211> LENGTH: 36
<212> TYPE: DNA
<213> ORGANISM: Artificial Sequence
<220> FEATURE:
<223> OTHER INFORMATION: sequencing result

<400> SEQUENCE: 45
aatcaaaccg acccaataat ttctactgtt gtagat                              36

<210> SEQ ID NO 46
<211> LENGTH: 36
<212> TYPE: DNA
<213> ORGANISM: Artificial Sequence
<220> FEATURE:
<223> OTHER INFORMATION: sequencing result

<400> SEQUENCE: 46
gtctaaagat atatctaaat ttctactatt gtagat                              36

<210> SEQ ID NO 47
<211> LENGTH: 36
<212> TYPE: DNA
<213> ORGANISM: Artificial Sequence
<220> FEATURE:
<223> OTHER INFORMATION: sequencing result

<400> SEQUENCE: 47
gtttaaaacc actttaaaat ttctactatt gtagat                              36

<210> SEQ ID NO 48
<211> LENGTH: 36
<212> TYPE: DNA
<213> ORGANISM: Artificial Sequence
<220> FEATURE:
<223> OTHER INFORMATION: sequencing result

<400> SEQUENCE: 48
gtctataaga catttataat ttctactatt gtagat                              36

<210> SEQ ID NO 49
<211> LENGTH: 36
<212> TYPE: DNA
<213> ORGANISM: Artificial Sequence
<220> FEATURE:
<223> OTHER INFORMATION: sequencing result

<400> SEQUENCE: 49
gtctagatta ccattttaat ttctactatt gtagat                              36

<210> SEQ ID NO 50
<211> LENGTH: 36
<212> TYPE: DNA
<213> ORGANISM: Artificial Sequence
<220> FEATURE:
<223> OTHER INFORMATION: sequencing result

<400> SEQUENCE: 50
ctctagcagg cctggcaaat ttctactgtt gtagat                              36

<210> SEQ ID NO 51
<211> LENGTH: 36
<212> TYPE: DNA
<213> ORGANISM: Artificial Sequence
<220> FEATURE:

<223> OTHER INFORMATION: sequencing result

<400> SEQUENCE: 51
gcctagaact tataaattat ttctactgtt gtagat                              36

<210> SEQ ID NO 52
<211> LENGTH: 36
<212> TYPE: DNA
<213> ORGANISM: Artificial Sequence
<220> FEATURE:
<223> OTHER INFORMATION: sequencing result

<400> SEQUENCE: 52
gcttagtact tataaagaat ttctactatt gtagat                              36

<210> SEQ ID NO 53
<211> LENGTH: 36
<212> TYPE: DNA
<213> ORGANISM: Artificial Sequence
<220> FEATURE:
<223> OTHER INFORMATION: sequencing result

<400> SEQUENCE: 53
gtctagaacc tcatgataat ttctactatt gtagat                              36

<210> SEQ ID NO 54
<211> LENGTH: 36
<212> TYPE: DNA
<213> ORGANISM: Artificial Sequence
<220> FEATURE:
<223> OTHER INFORMATION: sequencing result

<400> SEQUENCE: 54
gtctaagaga cccttaaaat ttctactgtt gtagat                              36

<210> SEQ ID NO 55
<211> LENGTH: 36
<212> TYPE: DNA
<213> ORGANISM: Artificial Sequence
<220> FEATURE:
<223> OTHER INFORMATION: sequencing result

<400> SEQUENCE: 55
gcttaagact tagaaataat ttctactatt gtagat                              36

<210> SEQ ID NO 56
<211> LENGTH: 86
<212> TYPE: DNA
<213> ORGANISM: Artificial Sequence
<220> FEATURE:
<223> OTHER INFORMATION: sequencing result

<400> SEQUENCE: 56
gtgaacttgg gtcagctgtt aacatcagta cgttaatgtt tcctgatggt ccatgtctgt    60
tactcgcctg tcaagtggcg tgacac                                        86

<210> SEQ ID NO 57
<211> LENGTH: 80
<212> TYPE: DNA
<213> ORGANISM: Artificial Sequence
<220> FEATURE:
<223> OTHER INFORMATION: sequencing result

<400> SEQUENCE: 57
gtgaacttgg gtcagctgtt aacatcagta cgttaatgtt tcctgatggt ccatgactcg    60

```
cctgtcaagt ggcgtgacac                                              80

<210> SEQ ID NO 58
<211> LENGTH: 86
<212> TYPE: DNA
<213> ORGANISM: Artificial Sequence
<220> FEATURE:
<223> OTHER INFORMATION: sequencing result

<400> SEQUENCE: 58
gtgaacttgg gtcagctgtt aacatcagta cgttaatgtt tcctgatggt ccatgtctgt    60
tactcgcctg tcaagtggcg tgacac                                        86

<210> SEQ ID NO 59
<211> LENGTH: 74
<212> TYPE: DNA
<213> ORGANISM: Artificial Sequence
<220> FEATURE:
<223> OTHER INFORMATION: sequencing result

<400> SEQUENCE: 59
gtgaacttgg gtcagctgtt aacatcagta cgttaatgtt tcctgatggt ccatgctgtc    60
aagtggcgtg acac                                                     74

<210> SEQ ID NO 60
<211> LENGTH: 5
<212> TYPE: DNA
<213> ORGANISM: Artificial Sequence
<220> FEATURE:
<223> OTHER INFORMATION: sequencing result

<400> SEQUENCE: 60 gttaa                                                                5

<210> SEQ ID NO 61
<211> LENGTH: 86
<212> TYPE: DNA
<213> ORGANISM: Artificial Sequence
<220> FEATURE:
<223> OTHER INFORMATION: sequencing result

<400> SEQUENCE: 61
gtgaacttgg gtcagctgtt aacatcagta cgttaatgtt tcctgatggt ccatgtctgt    60
tactcgcctg tcaagtggcg tgacac                                        86

<210> SEQ ID NO 62
<211> LENGTH: 86
<212> TYPE: DNA
<213> ORGANISM: Artificial Sequence
<220> FEATURE:
<223> OTHER INFORMATION: sequencing result

<400> SEQUENCE: 62
gtgaacttgg gtcagctgtt aacatcagta cgttaatgtt tcctgatggt ccatgcctgt    60
tactcgcctg tcaagtggcg tgacac                                        86

<210> SEQ ID NO 63
<211> LENGTH: 83
<212> TYPE: DNA
<213> ORGANISM: Artificial Sequence
<220> FEATURE:
<223> OTHER INFORMATION: sequencing result
```

-continued

<400> SEQUENCE: 63
gtgaacttgg gtcagctgtt aacatcagta cgttaatgtt tcctgatggt ccatgtctac    60
tcgcctgtca agtggcgtga cac    83

<210> SEQ ID NO 64
<211> LENGTH: 81
<212> TYPE: DNA
<213> ORGANISM: Artificial Sequence
<220> FEATURE:
<223> OTHER INFORMATION: sequencing result

<400> SEQUENCE: 64
gtgaacttgg gtcagctgtt aacatcagta cgttaatgtt tcctgatggt ccatgtctgt    60
gcctgtcaag tggcgtgaca c    81

<210> SEQ ID NO 65
<211> LENGTH: 78
<212> TYPE: DNA
<213> ORGANISM: Artificial Sequence
<220> FEATURE:
<223> OTHER INFORMATION: sequencing result

<400> SEQUENCE: 65
gtgaacttgg gtcagctgtt aacatcagta cgttaatgtt tcctgatggt ccatgtcgcc    60
tgtcaagtgg cgtgacac    78

<210> SEQ ID NO 66
<211> LENGTH: 70
<212> TYPE: DNA
<213> ORGANISM: Artificial Sequence
<220> FEATURE:
<223> OTHER INFORMATION: sequencing result

<400> SEQUENCE: 66
gtgaacttgg gtcagctgtt aacatcagta cgttaatgtt tcctgatggt cctgtcaagt    60
ggcgtgacac    70

<210> SEQ ID NO 67
<211> LENGTH: 86
<212> TYPE: DNA
<213> ORGANISM: Artificial Sequence
<220> FEATURE:
<223> OTHER INFORMATION: sequencing result

<400> SEQUENCE: 67
gtgaacttgg gtcagctgtt aacatcagta cgttaatgtt tcctgatggt ccatgtctgt    60
tactcgcctg tcaagtggcg tgacac    86

<210> SEQ ID NO 68
<211> LENGTH: 83
<212> TYPE: DNA
<213> ORGANISM: Artificial Sequence
<220> FEATURE:
<223> OTHER INFORMATION: sequencing result

<400> SEQUENCE: 68
gtgaacttgg gtcagctgtt aacatcagta cgttaatgtt tcctgatggt ccatgtttac    60
tcgcctgtca agtggcgtga cac    83

<210> SEQ ID NO 69
<211> LENGTH: 73

<212> TYPE: DNA
<213> ORGANISM: Artificial Sequence
<220> FEATURE:
<223> OTHER INFORMATION: sequencing result

<400> SEQUENCE: 69
gtgaacttgg gtcagctgtt aacatcagta cgttaatgtt tcctggttac tcgcctgtca    60
agtggcgtga cac    73

<210> SEQ ID NO 70
<211> LENGTH: 67
<212> TYPE: DNA
<213> ORGANISM: Artificial Sequence
<220> FEATURE:
<223> OTHER INFORMATION: sequencing result

<400> SEQUENCE: 70
gtgaacttgg gtcagctgtt aacatcagta cgttaatgtt tcctggtcct gtcaagtggc    60
gtgacac    67

<210> SEQ ID NO 71
<211> LENGTH: 24
<212> TYPE: DNA
<213> ORGANISM: Artificial Sequence
<220> FEATURE:
<223> OTHER INFORMATION: sequencing result

<400> SEQUENCE: 71
ctcgcctgtc aagtggcgtg acac    24

<210> SEQ ID NO 72
<211> LENGTH: 86
<212> TYPE: DNA
<213> ORGANISM: Artificial Sequence
<220> FEATURE:
<223> OTHER INFORMATION: sequencing result

<400> SEQUENCE: 72
gtgaacttgg gtcagctgtt aacatcagta cgttaatgtt tcctgatggt ccatgtctgt    60
tactcgcctg tcaagtggcg tgacac    86

<210> SEQ ID NO 73
<211> LENGTH: 86
<212> TYPE: DNA
<213> ORGANISM: Artificial Sequence
<220> FEATURE:
<223> OTHER INFORMATION: sequencing result

<400> SEQUENCE: 73
gtgaacttgg gtcagctgtt aacatcagta cgttaatgtt tcctgatggt ccatgtctgt    60
tactcgcctg tcaagtggcg tgacac    86

<210> SEQ ID NO 74
<211> LENGTH: 85
<212> TYPE: DNA
<213> ORGANISM: Artificial Sequence
<220> FEATURE:
<223> OTHER INFORMATION: sequencing result

<400> SEQUENCE: 74
gtgaacttgg gtcagctgtt aacatcagta cgttaatgtt tcctgatggt ccatgtcttt    60
actcgcctgt caagtggcgt gacac    85

```
<210> SEQ ID NO 75
<211> LENGTH: 81
<212> TYPE: DNA
<213> ORGANISM: Artificial Sequence
<220> FEATURE:
<223> OTHER INFORMATION: sequencing result

<400> SEQUENCE: 75
gtgaacttgg gtcagctgtt aacatcagta cgttaatgtt tcctgatggt ccatgtctac    60
gcctgtcaag tggcgtgaca c                                              81

<210> SEQ ID NO 76
<211> LENGTH: 71
<212> TYPE: DNA
<213> ORGANISM: Artificial Sequence
<220> FEATURE:
<223> OTHER INFORMATION: sequencing result

<400> SEQUENCE: 76
gtgaacttgg gtcagctgtt aacatcagta cgttaatgtt tcctgatggt ccatgtcaag    60
tggcgtgaca c                                                          71

<210> SEQ ID NO 77
<211> LENGTH: 74
<212> TYPE: DNA
<213> ORGANISM: Artificial Sequence
<220> FEATURE:
<223> OTHER INFORMATION: sequencing result

<400> SEQUENCE: 77
gtgaacttgg gtcagctgtt aacatcagta cgttaatgtt tcctgatgca ctcgcctgtc    60
aagtggcgtg acac                                                       74

<210> SEQ ID NO 78
<211> LENGTH: 71
<212> TYPE: DNA
<213> ORGANISM: Artificial Sequence
<220> FEATURE:
<223> OTHER INFORMATION: sequencing result

<400> SEQUENCE: 78
gtgaacttgg gtcagctgtt aacatcagta cgttaatgtt tcctgatggt ccatgtcaag    60
tggcgtgaca c                                                          71

<210> SEQ ID NO 79
<211> LENGTH: 69
<212> TYPE: DNA
<213> ORGANISM: Artificial Sequence
<220> FEATURE:
<223> OTHER INFORMATION: sequencing result

<400> SEQUENCE: 79
gtgaacttgg gtcagctgtt aacatcagta cgttaatgtt tcctgctcgc ctgtcaagtg    60
gcgtgacac                                                             69

<210> SEQ ID NO 80
<211> LENGTH: 69
<212> TYPE: DNA
<213> ORGANISM: Artificial Sequence
<220> FEATURE:
<223> OTHER INFORMATION: sequencing result

<400> SEQUENCE: 80
```

-continued

```
gtgaacttgg gtcagctgtt aacatcagta cgttaatgtt tcctgcacgc ctgtcaagtg    60
gcgtgacac                                                            69

<210> SEQ ID NO 81
<211> LENGTH: 66
<212> TYPE: DNA
<213> ORGANISM: Artificial Sequence
<220> FEATURE:
<223> OTHER INFORMATION: sequencing result

<400> SEQUENCE: 81
gtgaacttgg gtcagctgtt aacatcagta cgttaatgtt tcctcgcctg tcaagtggcg    60
tgacac                                                               66

<210> SEQ ID NO 82
<211> LENGTH: 68
<212> TYPE: DNA
<213> ORGANISM: Artificial Sequence
<220> FEATURE:
<223> OTHER INFORMATION: sequencing result

<400> SEQUENCE: 82
gtgaacttgg gtcagctgtt aacatcagta cgttaatgtt tctactcgcc tgtcaagtgg    60
cgtgacac                                                             68

<210> SEQ ID NO 83
<211> LENGTH: 52
<212> TYPE: DNA
<213> ORGANISM: Artificial Sequence
<220> FEATURE:
<223> OTHER INFORMATION: sequencing result

<400> SEQUENCE: 83
gtgaacttgg gtcagctgtt aacatcagta cgttaatgtt tcctgatgac ac            52

<210> SEQ ID NO 84
<211> LENGTH: 37
<212> TYPE: DNA
<213> ORGANISM: Artificial Sequence
<220> FEATURE:
<223> OTHER INFORMATION: sequencing result

<400> SEQUENCE: 84
gtgaactggc agatggtcct gtcaagtggc gtgacac                             37

<210> SEQ ID NO 85
<211> LENGTH: 24
<212> TYPE: DNA
<213> ORGANISM: Artificial Sequence
<220> FEATURE:
<223> OTHER INFORMATION: sequencing result

<400> SEQUENCE: 85
caggcctgtc aagtggcgtg acac                                           24

<210> SEQ ID NO 86
<211> LENGTH: 48
<212> TYPE: DNA
<213> ORGANISM: Artificial Sequence
<220> FEATURE:
<223> OTHER INFORMATION: sequencing result

<400> SEQUENCE: 86
```

```
gtgaacttgg gtcagctgtt aacatcagta cgttaatgtt tcctgatg              48
```

<210> SEQ ID NO 87
<211> LENGTH: 86
<212> TYPE: DNA
<213> ORGANISM: Artificial Sequence
<220> FEATURE:
<223> OTHER INFORMATION: sequencing result

<400> SEQUENCE: 87

```
gtgaacttgg gtcagctgtt aacatcagta cgttaatgtt tcctgatggt ccatgtctgt   60
tactcgcctg tcaagtggcg tgacac                                        86
```

<210> SEQ ID NO 88
<211> LENGTH: 81
<212> TYPE: DNA
<213> ORGANISM: Artificial Sequence
<220> FEATURE:
<223> OTHER INFORMATION: sequencing result

<400> SEQUENCE: 88

```
gtgaacttgg gtcagctgtt aacatcagta cgttaatgtt tcctgatggt ccatgtactc   60
gcctgtcaag tggcgtgaca c                                             81
```

<210> SEQ ID NO 89
<211> LENGTH: 86
<212> TYPE: DNA
<213> ORGANISM: Artificial Sequence
<220> FEATURE:
<223> OTHER INFORMATION: sequencing result

<400> SEQUENCE: 89

```
gtgaacttgg gtcagctgtt aacatcagta cgttaatgtt tcctgatggt ccatgtctgt   60
tactcgcctg tcaagtggcg tgacac                                        86
```

<210> SEQ ID NO 90
<211> LENGTH: 81
<212> TYPE: DNA
<213> ORGANISM: Artificial Sequence
<220> FEATURE:
<223> OTHER INFORMATION: sequencing result

<400> SEQUENCE: 90

```
gtgaacttgg gtcagctgtt aacatcagta cgttaatgtt tcctgatggt ccatgtactc   60
gcctgtcaag tggcgtgaca c                                             81
```

<210> SEQ ID NO 91
<211> LENGTH: 86
<212> TYPE: DNA
<213> ORGANISM: Artificial Sequence
<220> FEATURE:
<223> OTHER INFORMATION: sequencing result

<400> SEQUENCE: 91

```
gtgaacttgg gtcagctgtt aacatcagta cgttaatgtt tcctgatggt ccatgtctgt   60
tactcgcctg tcaagtggcg tgacac                                        86
```

<210> SEQ ID NO 92
<211> LENGTH: 80
<212> TYPE: DNA
<213> ORGANISM: Artificial Sequence
<220> FEATURE:
<223> OTHER INFORMATION: sequencing result

<400> SEQUENCE: 92
gtgaacttgg gtcagctgtt aacatcagta cgttaatgtt tcctgatggt ccatgactcg    60
cctgtcaagt ggcgtgacac                                                80

<210> SEQ ID NO 93
<211> LENGTH: 78
<212> TYPE: DNA
<213> ORGANISM: Artificial Sequence
<220> FEATURE:
<223> OTHER INFORMATION: sequencing result

<400> SEQUENCE: 93
gtgaacttgg gtcagctgtt aacatcagta cgttaatgtt tcctgatggt ccatgtcgcc    60
tgtcaagtgg cgtgacac                                                  78

<210> SEQ ID NO 94
<211> LENGTH: 69
<212> TYPE: DNA
<213> ORGANISM: Artificial Sequence
<220> FEATURE:
<223> OTHER INFORMATION: sequencing result

<400> SEQUENCE: 94
gtgaacttgg gtcagctgtt aacatcagta cgttaatgtt tcctgatggt ccaacaagtg    60
gcgtgacac                                                            69

<210> SEQ ID NO 95
<211> LENGTH: 89
<212> TYPE: DNA
<213> ORGANISM: Artificial Sequence
<220> FEATURE:
<223> OTHER INFORMATION: sequencing result

<400> SEQUENCE: 95
gggctggccc tggggccgtt tccctcactc ctgctcggtg aatttggctc agcaggcacc    60
tgcctcagct gctcacttga gcctctggg                                      89

<210> SEQ ID NO 96
<211> LENGTH: 51
<212> TYPE: DNA
<213> ORGANISM: Artificial Sequence
<220> FEATURE:
<223> OTHER INFORMATION: sequencing result

<400> SEQUENCE: 96
gggctggccc tggggccgtt tccctcactc ctgctcactt gagcctctgg g              51

<210> SEQ ID NO 97
<211> LENGTH: 87
<212> TYPE: DNA
<213> ORGANISM: Artificial Sequence
<220> FEATURE:
<223> OTHER INFORMATION: sequencing result

<400> SEQUENCE: 97
gggctggccc tggggccgtt tccctcactc ctgctctgaa tttggctcag caggcacctg    60
cctcagctgc tcacttgagc ctctggg                                        87

<210> SEQ ID NO 98
<211> LENGTH: 89
<212> TYPE: DNA

<213> ORGANISM: Artificial Sequence
<220> FEATURE:
<223> OTHER INFORMATION: sequencing result

<400> SEQUENCE: 98
gggctggccc tggggccgtt ccctcactc ctgctcggtg aatttggctc agcaggcacc    60
tgcctcagct gctcacttga gcctctggg                                     89

<210> SEQ ID NO 99
<211> LENGTH: 89
<212> TYPE: DNA
<213> ORGANISM: Artificial Sequence
<220> FEATURE:
<223> OTHER INFORMATION: sequencing result

<400> SEQUENCE: 99
gggctggccc tggggccgtt ccctcactc ctgctcggtg aatttggctc agcaggcacc    60
tgcctcagct gctcacttga gcctctggg                                     89

<210> SEQ ID NO 100
<211> LENGTH: 89
<212> TYPE: DNA
<213> ORGANISM: Artificial Sequence
<220> FEATURE:
<223> OTHER INFORMATION: sequencing result

<400> SEQUENCE: 100
gggctggccc tggggccgtt ccctcactc ctgctcggtg aatttggctc agcaggcacc    60
tgcctcagct gctcacttga gcctctggg                                     89

<210> SEQ ID NO 101
<211> LENGTH: 66
<212> TYPE: DNA
<213> ORGANISM: Artificial Sequence
<220> FEATURE:
<223> OTHER INFORMATION: sequencing result

<400> SEQUENCE: 101
gggctggccc tggggccgtt ccctcactc aggcacctgc ctcagctgct cacttgagcc    60
tctggg                                                              66

<210> SEQ ID NO 102
<211> LENGTH: 82
<212> TYPE: DNA
<213> ORGANISM: Artificial Sequence
<220> FEATURE:
<223> OTHER INFORMATION: sequencing result

<400> SEQUENCE: 102
gggctggccc tggggccgtt ccctcactc ctgcatttgg ctcagcaggc acctgcctca    60
gctgctcact tgagcctctg gg                                            82

<210> SEQ ID NO 103
<211> LENGTH: 85
<212> TYPE: DNA
<213> ORGANISM: Artificial Sequence
<220> FEATURE:
<223> OTHER INFORMATION: sequencing result

<400> SEQUENCE: 103
gggctggccc tggggccgtt ccctcactc ctgctcgatt tggctcagca ggcacctgcc    60
tcagctgctc acttgagcct ctggg                                         85

<210> SEQ ID NO 104
<211> LENGTH: 88
<212> TYPE: DNA
<213> ORGANISM: Artificial Sequence
<220> FEATURE:
<223> OTHER INFORMATION: sequencing result

<400> SEQUENCE: 104
gggctggccc tggggccgtt ccctcactc ctgctcggtg atttggctca gcaggcacct    60
gcctcagctg ctcacttgag cctctggg                                      88

<210> SEQ ID NO 105
<211> LENGTH: 63
<212> TYPE: DNA
<213> ORGANISM: Artificial Sequence
<220> FEATURE:
<223> OTHER INFORMATION: sequencing result

<400> SEQUENCE: 105
gggctggccc tggggccgtt ccctcactc ctgctccctc agctgctcac ttgagcctct    60
ggg                                                                 63

<210> SEQ ID NO 106
<211> LENGTH: 84
<212> TYPE: DNA
<213> ORGANISM: Artificial Sequence
<220> FEATURE:
<223> OTHER INFORMATION: sequencing result

<400> SEQUENCE: 106
gggctggccc tggggccgtt ccctcactc ctgctcggtt ggctcagcag gcacctgcct    60
cagctgctca cttgagcctc tggg                                          84

<210> SEQ ID NO 107
<211> LENGTH: 79
<212> TYPE: DNA
<213> ORGANISM: Artificial Sequence
<220> FEATURE:
<223> OTHER INFORMATION: sequencing result

<400> SEQUENCE: 107
gggctggccc tggggccgtt ccctcactc ctgctcactc agcaggcacc tgcctcagct    60
gctcacttga gcctctggg                                                79

<210> SEQ ID NO 108
<211> LENGTH: 73
<212> TYPE: DNA
<213> ORGANISM: Artificial Sequence
<220> FEATURE:
<223> OTHER INFORMATION: sequencing result

<400> SEQUENCE: 108
gggctggccc tggggccgtt ccctcactc ctgcgcctca cacctgcctc agctgctcac    60
ttgagcctct ggg                                                      73

<210> SEQ ID NO 109
<211> LENGTH: 89
<212> TYPE: DNA
<213> ORGANISM: Artificial Sequence
<220> FEATURE:
<223> OTHER INFORMATION: sequencing result

<400> SEQUENCE: 109
gggctggccc tggggccgtt tccctcactc ctgctcggtg aatttggctc agcaggcacc    60
tgcctcagct gctcacttga gcctctggg                                      89

<210> SEQ ID NO 110
<211> LENGTH: 88
<212> TYPE: DNA
<213> ORGANISM: Artificial Sequence
<220> FEATURE:
<223> OTHER INFORMATION: sequencing result

<400> SEQUENCE: 110
gggctggccc tggggccgtt tccctcactc ctgctcggtg aattggctca gcaggcacct    60
gcctcagctg ctcacttgag cctctggg                                       88

<210> SEQ ID NO 111
<211> LENGTH: 80
<212> TYPE: DNA
<213> ORGANISM: Artificial Sequence
<220> FEATURE:
<223> OTHER INFORMATION: sequencing result

<400> SEQUENCE: 111
gggctggccc tggggccgtt tccctcactc ctgctcggct cagcaggcac ctgcctcagc    60
tgctcacttg agcctctggg                                                80

<210> SEQ ID NO 112
<211> LENGTH: 45
<212> TYPE: DNA
<213> ORGANISM: Artificial Sequence
<220> FEATURE:
<223> OTHER INFORMATION: sequencing result

<400> SEQUENCE: 112
gggctggccc tggggccgtt tccctcactc ctgctcgcct ctggg                    45

<210> SEQ ID NO 113
<211> LENGTH: 75
<212> TYPE: DNA
<213> ORGANISM: Artificial Sequence
<220> FEATURE:
<223> OTHER INFORMATION: sequencing result

<400> SEQUENCE: 113
gggctggccc tggggccgtt tccctcactc ctgctcagca ggcacctgcc tcagctgctc    60
acttgagcct ctggg                                                     75

<210> SEQ ID NO 114
<211> LENGTH: 85
<212> TYPE: DNA
<213> ORGANISM: Artificial Sequence
<220> FEATURE:
<223> OTHER INFORMATION: sequencing result

<400> SEQUENCE: 114
gggctggccc tggggccgtt tccctcactc ctgctgaatt tggctcagca ggcacctgcc    60
tcagctgctc acttgagcct ctggg                                          85

<210> SEQ ID NO 115
<211> LENGTH: 89
<212> TYPE: DNA
<213> ORGANISM: Artificial Sequence

```
<220> FEATURE:
<223> OTHER INFORMATION: sequencing result

<400> SEQUENCE: 115
gggctggccc tggggccgtt ccctcactc ctgctcggtg aatttggctc agcaggcacc    60
tgcctcagct gctcacttga gcctctggg                                     89

<210> SEQ ID NO 116
<211> LENGTH: 87
<212> TYPE: DNA
<213> ORGANISM: Artificial Sequence
<220> FEATURE:
<223> OTHER INFORMATION: sequencing result

<400> SEQUENCE: 116
gggctggccc tggggccgtt ccctcactc ctgctcggtg aatggctcag caggcacctg    60
cctcagctgc tcacttgagc ctctggg                                       87

<210> SEQ ID NO 117
<211> LENGTH: 89
<212> TYPE: DNA
<213> ORGANISM: Artificial Sequence
<220> FEATURE:
<223> OTHER INFORMATION: sequencing result

<400> SEQUENCE: 117
gggctggccc tggggccgtt ccctcactc ctgctcggtg aatttggctc agcaggcacc    60
tgcctcagct gctcacttga gcctctggg                                     89

<210> SEQ ID NO 118
<211> LENGTH: 60
<212> TYPE: DNA
<213> ORGANISM: Artificial Sequence
<220> FEATURE:
<223> OTHER INFORMATION: sequencing result

<400> SEQUENCE: 118
gggctggccc tggggccgtt ccctcactc ctgcctcagc tgctcacttg agcctctggg    60

<210> SEQ ID NO 119
<211> LENGTH: 89
<212> TYPE: DNA
<213> ORGANISM: Artificial Sequence
<220> FEATURE:
<223> OTHER INFORMATION: sequencing result

<400> SEQUENCE: 119
gggctggccc tggggccgtt ccctcactc ctgctcggtg aatttggctc agcaggcacc    60
tgcctcagct gctcacttga gcctctggg                                     89

<210> SEQ ID NO 120
<211> LENGTH: 88
<212> TYPE: DNA
<213> ORGANISM: Artificial Sequence
<220> FEATURE:
<223> OTHER INFORMATION: sequencing result

<400> SEQUENCE: 120
gggctggccc tggggccgtt ccctcactc ctgctcggtg aattggctca gcaggcacct    60
gcctcagctg ctcacttgag cctctggg                                      88

<210> SEQ ID NO 121
```

```
<211> LENGTH: 89
<212> TYPE: DNA
<213> ORGANISM: Artificial Sequence
<220> FEATURE:
<223> OTHER INFORMATION: sequencing result

<400> SEQUENCE: 121
aaccctctgg ggaccgtttg aggagtgttc agtctccgtg aacgttccct tagcactctg    60
ccacttattg ggtcagctgt taacatcag                                      89

<210> SEQ ID NO 122
<211> LENGTH: 89
<212> TYPE: DNA
<213> ORGANISM: Artificial Sequence
<220> FEATURE:
<223> OTHER INFORMATION: sequencing result

<400> SEQUENCE: 122
aaccctctgg ggaccgtttg aggagtgttc agtctccgtg aacgttccct tagcactctg    60
ccacttattg ggtcagctgt taacatcag                                      89

<210> SEQ ID NO 123
<211> LENGTH: 89
<212> TYPE: DNA
<213> ORGANISM: Artificial Sequence
<220> FEATURE:
<223> OTHER INFORMATION: sequencing result

<400> SEQUENCE: 123
aaccctctgg ggaccgtttg aggagtgttc agtctccgtg aacgttccct tagcactctg    60
ccacttattg ggtcagctgt taacatcag                                      89

<210> SEQ ID NO 124
<211> LENGTH: 89
<212> TYPE: DNA
<213> ORGANISM: Artificial Sequence
<220> FEATURE:
<223> OTHER INFORMATION: sequencing result

<400> SEQUENCE: 124
aaccctctgg ggaccgtttg aggagtgttc agtctccgtg aacgttccct tagcactctg    60
ccacttattg ggtcagctgt taacatcag                                      89

<210> SEQ ID NO 125
<211> LENGTH: 89
<212> TYPE: DNA
<213> ORGANISM: Artificial Sequence
<220> FEATURE:
<223> OTHER INFORMATION: sequencing result

<400> SEQUENCE: 125
aaccctctgg ggaccgtttg aggagtgttc agtctccgtg aacgttccct tagcactctg    60
ccacttattg ggtcagctgt taacatcag                                      89

<210> SEQ ID NO 126
<211> LENGTH: 89
<212> TYPE: DNA
<213> ORGANISM: Artificial Sequence
<220> FEATURE:
<223> OTHER INFORMATION: sequencing result

<400> SEQUENCE: 126
aaccctctgg ggaccgtttg aggagtgttc agtctccgtg aacgttccct tagcactctg    60
```
ccacttattg ggtcagctgt taacatcag          89

<210> SEQ ID NO 127
<211> LENGTH: 89
<212> TYPE: DNA
<213> ORGANISM: Artificial Sequence
<220> FEATURE:
<223> OTHER INFORMATION: sequencing result

<400> SEQUENCE: 127
aaccctctgg ggaccgtttg aggagtgttc agtctccgtg agcgttccct tagcactctg          60
ccacttattg ggtcagctgt taacatcag          89

<210> SEQ ID NO 128
<211> LENGTH: 87
<212> TYPE: DNA
<213> ORGANISM: Artificial Sequence
<220> FEATURE:
<223> OTHER INFORMATION: sequencing result

<400> SEQUENCE: 128
aaccctctgg ggaccgtttg aggagtgttc agtctccgtg agttcccctta gcactctgcc          60 acttattggg tcagctgtta acatcag          87

<210> SEQ ID NO 129
<211> LENGTH: 83
<212> TYPE: DNA
<213> ORGANISM: Artificial Sequence
<220> FEATURE:
<223> OTHER INFORMATION: sequencing result

<400> SEQUENCE: 129
aaccctctgg ggaccgtttg aggagtgttc agtctccgtt cccttagcac tctgccactt          60
attgggtcag ctgttaacat cag          83

<210> SEQ ID NO 130
<211> LENGTH: 79
<212> TYPE: DNA
<213> ORGANISM: Artificial Sequence
<220> FEATURE:
<223> OTHER INFORMATION: sequencing result

<400> SEQUENCE: 130
aaccctctgg ggaccgtttg aggagtgttc agtgttccct tagcactctg ccacttattg          60
ggtcagctgt taacatcag          79

<210> SEQ ID NO 131
<211> LENGTH: 89
<212> TYPE: DNA
<213> ORGANISM: Artificial Sequence
<220> FEATURE:
<223> OTHER INFORMATION: sequencing result

<400> SEQUENCE: 131
aaccctctgg ggaccgtttg aggagtgttc agtctccgtg aacgttccct tagcactctg          60
ccacttattg ggtcagctgt taacatcag          89

<210> SEQ ID NO 132
<211> LENGTH: 87
<212> TYPE: DNA
<213> ORGANISM: Artificial Sequence
<220> FEATURE:

<223> OTHER INFORMATION: sequencing result

<400> SEQUENCE: 132
aaccctctgg ggaccgtttg aggagtgttc agtctccgtg agttcccttgca gcactctgcc    60 acttattggg tcagctgtta acatcag    87

<210> SEQ ID NO 133
<211> LENGTH: 83
<212> TYPE: DNA
<213> ORGANISM: Artificial Sequence
<220> FEATURE:
<223> OTHER INFORMATION: sequencing result

<400> SEQUENCE: 133
aaccctctgg ggaccgtttg aggagtgttc agtctccgtt cccttagcac tctgccactt    60
attgggtcag ctgttaacat cag    83

<210> SEQ ID NO 134
<211> LENGTH: 79
<212> TYPE: DNA
<213> ORGANISM: Artificial Sequence
<220> FEATURE:
<223> OTHER INFORMATION: sequencing result

<400> SEQUENCE: 134
aaccctctgg ggaccgtttg aggagtgttc agtgttccct tagcactctg ccacttattg    60
ggtcagctgt taacatcag    79

<210> SEQ ID NO 135
<211> LENGTH: 89
<212> TYPE: DNA
<213> ORGANISM: Artificial Sequence
<220> FEATURE:
<223> OTHER INFORMATION: sequencing result

<400> SEQUENCE: 135
aaccctctgg ggaccgtttg aggagtgttc agtctccgtg aacgttccct tagcactctg    60
ccacttattg ggtcagctgt taacatcag    89

<210> SEQ ID NO 136
<211> LENGTH: 88
<212> TYPE: DNA
<213> ORGANISM: Artificial Sequence
<220> FEATURE:
<223> OTHER INFORMATION: sequencing result

<400> SEQUENCE: 136
aaccctctgg ggaccgtttg aggagtgttc agtctccgtc acgttccctt agcactctgc    60
cacttattgg gtcagctgtt aacatcag    88

<210> SEQ ID NO 137
<211> LENGTH: 89
<212> TYPE: DNA
<213> ORGANISM: Artificial Sequence
<220> FEATURE:
<223> OTHER INFORMATION: sequencing result

<400> SEQUENCE: 137
aaccctctgg ggaccgtttg aggagtgttc agtctccgtg aacgttccct tagcactctg    60
ccacttattg ggtcagctgt taacatcag    89

-continued

```
<210> SEQ ID NO 138
<211> LENGTH: 55
<212> TYPE: DNA
<213> ORGANISM: Artificial Sequence
<220> FEATURE:
<223> OTHER INFORMATION: sequencing result

<400> SEQUENCE: 138
aaccctctgg ggaccgtttg aggagtgttc ttattgggtc agctgttaac atcag      55

<210> SEQ ID NO 139
<211> LENGTH: 74
<212> TYPE: DNA
<213> ORGANISM: Artificial Sequence
<220> FEATURE:
<223> OTHER INFORMATION: sequencing result

<400> SEQUENCE: 139
gtggaaaact ccctttgtga aatggtgcg tcctaggtgt tcaccaggtc gtggccgcct  60
ctactccctt tctc                                                   74

<210> SEQ ID NO 140
<211> LENGTH: 69
<212> TYPE: DNA
<213> ORGANISM: Artificial Sequence
<220> FEATURE:
<223> OTHER INFORMATION: sequencing result

<400> SEQUENCE: 140
gtggaaaact cccctttgtga aatggtgcg ggtgttcacc aggtcgtggc cgcctctact  60
cccttttctc                                                        69

<210> SEQ ID NO 141
<211> LENGTH: 77
<212> TYPE: DNA
<213> ORGANISM: Artificial Sequence
<220> FEATURE:
<223> OTHER INFORMATION: sequencing result

<400> SEQUENCE: 141
gtggaaaact cccctttgtga aatggtgcg tccctatagg tgttcaccag gtcgtggccg  60
cctctactcc ctttctc                                                77

<210> SEQ ID NO 142
<211> LENGTH: 73
<212> TYPE: DNA
<213> ORGANISM: Artificial Sequence
<220> FEATURE:
<223> OTHER INFORMATION: sequencing result

<400> SEQUENCE: 142
gtggaaaact cccctttgtga aatggtgcg tctaggtgtt caccaggtcg tggccgcctc  60
tactcccttt ctc                                                    73

<210> SEQ ID NO 143
<211> LENGTH: 74
<212> TYPE: DNA
<213> ORGANISM: Artificial Sequence
<220> FEATURE:
<223> OTHER INFORMATION: sequencing result

<400> SEQUENCE: 143
gtggaaaact cccctttgtga aatggtgcg cacaccccca tttccaggtc gtggccgcct  60
```
ctactcccTT TCTC 74

<210> SEQ ID NO 144
<211> LENGTH: 77
<212> TYPE: DNA
<213> ORGANISM: Artificial Sequence
<220> FEATURE:
<223> OTHER INFORMATION: sequencing result

<400> SEQUENCE: 144
gtggaaaact ccctttgtga aatggtgcg tcctaggtgt tcaccaggtc gtggccgcct    60
ctactcccTT TCTCTTT 77

<210> SEQ ID NO 145
<211> LENGTH: 75
<212> TYPE: DNA
<213> ORGANISM: Artificial Sequence
<220> FEATURE:
<223> OTHER INFORMATION: sequencing result

<400> SEQUENCE: 145
gtggaaaact ccctttgtga aatggtgcg tccggtgttc accaggtcgt ggccgcctct    60
actccctttc tctt    75

<210> SEQ ID NO 146
<211> LENGTH: 48
<212> TYPE: DNA
<213> ORGANISM: Artificial Sequence
<220> FEATURE:
<223> OTHER INFORMATION: sequencing result

<400> SEQUENCE: 146
gtggaaaact ccctttgtga aatggtgcg tctactccct ttctcttt    48

<210> SEQ ID NO 147
<211> LENGTH: 77
<212> TYPE: DNA
<213> ORGANISM: Artificial Sequence
<220> FEATURE:
<223> OTHER INFORMATION: sequencing result

<400> SEQUENCE: 147
tgcgtcctag gtgttcacca ggtcgtggcc gcctctactc cctttctctt tctccatcct    60
tctttccTTA AAGAGTC 77

<210> SEQ ID NO 148
<211> LENGTH: 76
<212> TYPE: DNA
<213> ORGANISM: Artificial Sequence
<220> FEATURE:
<223> OTHER INFORMATION: sequencing result

<400> SEQUENCE: 148
tgcgtcctag gtgttcacca ggtcgtggcc gcctctactc ctttctcttt ctccatcctt    60
ctttccTTAA AGAGTC 76

<210> SEQ ID NO 149
<211> LENGTH: 75
<212> TYPE: DNA
<213> ORGANISM: Artificial Sequence
<220> FEATURE:
<223> OTHER INFORMATION: sequencing result

<400> SEQUENCE: 149

```
tgcgtcctag gtgttcacca ggtcgtggcc gcctactccc tttctctttc tccatccttc    60
tttccttaaa gagtc                                                     75

<210> SEQ ID NO 150
<211> LENGTH: 72
<212> TYPE: DNA
<213> ORGANISM: Artificial Sequence
<220> FEATURE:
<223> OTHER INFORMATION: sequencing result

<400> SEQUENCE: 150
tgcgtcctag gtgttcacca ggtcgtggcc gcctcccttt ctctttctcc atccttcttt    60
ccttaaagag tc                                                        72

<210> SEQ ID NO 151
<211> LENGTH: 49
<212> TYPE: DNA
<213> ORGANISM: Artificial Sequence
<220> FEATURE:
<223> OTHER INFORMATION: sequencing result

<400> SEQUENCE: 151 aggaggggg tgtccgtgtg gaaaactccc tttgtgagaa tggtgcgtc                 49

<210> SEQ ID NO 152
<211> LENGTH: 77
<212> TYPE: DNA
<213> ORGANISM: Artificial Sequence
<220> FEATURE:
<223> OTHER INFORMATION: sequencing result

<400> SEQUENCE: 152 aggaggggg tgtccgtgtg gaaaactccc ttttgttcgc cagttaatag tttgcgcaac    60
ggtgagaatg gtgcgtc                                                   77

<210> SEQ ID NO 153
<211> LENGTH: 47
<212> TYPE: DNA
<213> ORGANISM: Artificial Sequence
<220> FEATURE:
<223> OTHER INFORMATION: sequencing result

<400> SEQUENCE: 153 aggaggggg tgtccgtgtg gaaaactccc tttgagaatg gtgcgtc                   47

<210> SEQ ID NO 154
<211> LENGTH: 40
<212> TYPE: DNA
<213> ORGANISM: Artificial Sequence
<220> FEATURE:
<223> OTHER INFORMATION: sequencing result

<400> SEQUENCE: 154 aggaggggg tgtccgtgtg gaaaactaca atggtgcgtc                           40

<210> SEQ ID NO 155
<211> LENGTH: 75
<212> TYPE: DNA
<213> ORGANISM: Artificial Sequence
<220> FEATURE:
<223> OTHER INFORMATION: sequencing result

<400> SEQUENCE: 155
```

-continued

```
ggcgctcagg cttccctgtc cccttcctc gtccaccatc tcatgcccct ggctctcctg    60 cccttccct acagg                                                     75

<210> SEQ ID NO 156
<211> LENGTH: 77
<212> TYPE: DNA
<213> ORGANISM: Artificial Sequence
<220> FEATURE:
<223> OTHER INFORMATION: sequencing result

<400> SEQUENCE: 156
ggcgctcagg cttccctgtc cccttcctc gtccaccaca tctcatgccc ctggctctcc    60
tgccccttcc ctacagg                                                  77

<210> SEQ ID NO 157
<211> LENGTH: 63
<212> TYPE: DNA
<213> ORGANISM: Artificial Sequence
<220> FEATURE:
<223> OTHER INFORMATION: sequencing result

<400> SEQUENCE: 157
ggcgctcagg cttccctgtc cccttcctc atgccctgg ctctcctgcc ccttccctac     60
agg                                                                 63

<210> SEQ ID NO 158
<211> LENGTH: 63
<212> TYPE: DNA
<213> ORGANISM: Artificial Sequence
<220> FEATURE:
<223> OTHER INFORMATION: sequencing result

<400> SEQUENCE: 158
ggcgctcagg cttccctgtc cccttcctc gtgcccctgg ctctcctgcc ccttccctac    60
agg                                                                 63

<210> SEQ ID NO 159
<211> LENGTH: 77
<212> TYPE: DNA
<213> ORGANISM: Artificial Sequence
<220> FEATURE:
<223> OTHER INFORMATION: sequencing result

<400> SEQUENCE: 159
tccgtgtgga aaactccctt tgtgagaatg gtgcgtccta ggtgttcacc aggtcgtggc    60
cgcctctact cccttttc                                                  77

<210> SEQ ID NO 160
<211> LENGTH: 70
<212> TYPE: DNA
<213> ORGANISM: Artificial Sequence
<220> FEATURE:
<223> OTHER INFORMATION: sequencing result

<400> SEQUENCE: 160
tccgtgtgga aaactccctt tgtgagaatg ctaggtgttc accaggtcgt ggccgcctct    60
actcccttc                                                            70

<210> SEQ ID NO 161
<211> LENGTH: 65
<212> TYPE: DNA
<213> ORGANISM: Artificial Sequence
```

-continued

```
<220> FEATURE:
<223> OTHER INFORMATION: sequencing result

<400> SEQUENCE: 161
tccgtgtgga aaactccctt gcgtcctagg tgttcaccag gtcgtggccg cctctactcc    60
ctttc                                                                65

<210> SEQ ID NO 162
<211> LENGTH: 64
<212> TYPE: DNA
<213> ORGANISM: Artificial Sequence
<220> FEATURE:
<223> OTHER INFORMATION: sequencing result

<400> SEQUENCE: 162
tccgtgtgga aaactccctt tgtgagaacg gttcaccagg tcgtggccgc ctctactccc    60
tttc                                                                 64

<210> SEQ ID NO 163
<211> LENGTH: 75
<212> TYPE: DNA
<213> ORGANISM: Artificial Sequence
<220> FEATURE:
<223> OTHER INFORMATION: sequencing result

<400> SEQUENCE: 163
tccgtgtgga aaactccctt tgtgagaatt gcgtcctagg tgttcaccag gtcgtggccg    60
cctctactcc ctttc                                                     75

<210> SEQ ID NO 164
<211> LENGTH: 59
<212> TYPE: DNA
<213> ORGANISM: Artificial Sequence
<220> FEATURE:
<223> OTHER INFORMATION: sequencing result

<400> SEQUENCE: 164
tccgtgtgga aaactccctt tgtgagttca ccaggtcgtg gccgcctcta ctcccttt     59

<210> SEQ ID NO 165
<211> LENGTH: 76
<212> TYPE: DNA
<213> ORGANISM: Artificial Sequence
<220> FEATURE:
<223> OTHER INFORMATION: sequencing result

<400> SEQUENCE: 165
ctctcctgcc ccttccctac aggggttcct ggctctgctc ttcagactga gccccgttcc    60
cctgcatccc cgttcc                                                    76

<210> SEQ ID NO 166
<211> LENGTH: 77
<212> TYPE: DNA
<213> ORGANISM: Artificial Sequence
<220> FEATURE:
<223> OTHER INFORMATION: sequencing result

<400> SEQUENCE: 166
ctctcctgcc ccttccctac aggggttcct ggcttctgct cttcagactg agccccgttc    60
ccctgcatcc ccgttcc                                                   77

<210> SEQ ID NO 167
```

```
<211> LENGTH: 63
<212> TYPE: DNA
<213> ORGANISM: Artificial Sequence
<220> FEATURE:
<223> OTHER INFORMATION: sequencing result

<400> SEQUENCE: 167
ctctcctgcc ccttccctac aggggttcct ggactgagcc ccgttcccct gcatcccgt      60 tcc                                                                    63

<210> SEQ ID NO 168
<211> LENGTH: 70
<212> TYPE: DNA
<213> ORGANISM: Artificial Sequence
<220> FEATURE:
<223> OTHER INFORMATION: sequencing result

<400> SEQUENCE: 168
ctctcctgcc ccttccctac aggggttcct gctcttcaga ctgagcccg ttcccctgca      60 tccccgttcc                                                             70

<210> SEQ ID NO 169
<211> LENGTH: 70
<212> TYPE: DNA
<213> ORGANISM: Artificial Sequence
<220> FEATURE:
<223> OTHER INFORMATION: sequencing result

<400> SEQUENCE: 169
ctctcctgcc ccttccctac aggggttcct gagcttcaga ctgagcccg ttcccctgca      60 tccccgttcc                                                             70

<210> SEQ ID NO 170
<211> LENGTH: 77
<212> TYPE: DNA
<213> ORGANISM: Artificial Sequence
<220> FEATURE:
<223> OTHER INFORMATION: sequencing result

<400> SEQUENCE: 170
atgaagtcca gcatgcccca ttagatctta cccagggttc tcaggctgct cccagcaaac     60
tggaaggaga gatttct                                                    77

<210> SEQ ID NO 171
<211> LENGTH: 67
<212> TYPE: DNA
<213> ORGANISM: Artificial Sequence
<220> FEATURE:
<223> OTHER INFORMATION: sequencing result

<400> SEQUENCE: 171
atgaagtcca gcatgcccca ttagatctta ccaggctgct cccagcaaac tggaaggaga     60
gatttct                                                                67

<210> SEQ ID NO 172
<211> LENGTH: 51
<212> TYPE: DNA
<213> ORGANISM: Artificial Sequence
<220> FEATURE:
<223> OTHER INFORMATION: sequencing result

<400> SEQUENCE: 172
atgaagtcca gcatgcccca ttagatcagc aaactggaag gagagatttc t              51
```

<210> SEQ ID NO 173
<211> LENGTH: 68
<212> TYPE: DNA
<213> ORGANISM: Artificial Sequence
<220> FEATURE:
<223> OTHER INFORMATION: sequencing result

<400> SEQUENCE: 173
ccagcaaact ggaaggagag atttctcggg tcagcacagc tgatgtcaaa gccacagcga    60
tgtccatg    68

<210> SEQ ID NO 174
<211> LENGTH: 70
<212> TYPE: DNA
<213> ORGANISM: Artificial Sequence
<220> FEATURE:
<223> OTHER INFORMATION: sequencing result

<400> SEQUENCE: 174
ccagcaaact ggaaggagag atttctcggg tcagggctca gctgatgtca aagccacagc    60
gatgtccatg    70

<210> SEQ ID NO 175
<211> LENGTH: 72
<212> TYPE: DNA
<213> ORGANISM: Artificial Sequence
<220> FEATURE:
<223> OTHER INFORMATION: sequencing result

<400> SEQUENCE: 175
ccagcaaact ggaaggagag atttctcggg tcaactggct cagctgatgt caaagccaca    60
gcgatgtcca tg    72

<210> SEQ ID NO 176
<211> LENGTH: 71
<212> TYPE: DNA
<213> ORGANISM: Artificial Sequence
<220> FEATURE:
<223> OTHER INFORMATION: sequencing result

<400> SEQUENCE: 176
ccagcaaact ggaaggagag atttctcggg gtctcggctc agctgatgtc aaagccacag    60
cgatgtccat g    71

<210> SEQ ID NO 177
<211> LENGTH: 62
<212> TYPE: DNA
<213> ORGANISM: Artificial Sequence
<220> FEATURE:
<223> OTHER INFORMATION: sequencing result

<400> SEQUENCE: 177
ccagcaaact ggaaggagag atttctcggg tcagcaatgt caaagccaca gcgatgtcca    60
tg    62

<210> SEQ ID NO 178
<211> LENGTH: 66
<212> TYPE: DNA
<213> ORGANISM: Artificial Sequence
<220> FEATURE:
<223> OTHER INFORMATION: sequencing result

```
<400> SEQUENCE: 178
ccagcaaact ggaaggagag atttctcggg tcagcaactg atgtcaaagc cacagcgatg    60
tccatg                                                               66

<210> SEQ ID NO 179
<211> LENGTH: 77
<212> TYPE: DNA
<213> ORGANISM: Artificial Sequence
<220> FEATURE:
<223> OTHER INFORMATION: sequencing result

<400> SEQUENCE: 179
ccagcaaact ggaaggagag atttctcggg tcagcatcac tggctcagct gatgtcaaag    60
ccacagcgat gtccatg                                                   77

<210> SEQ ID NO 180
<211> LENGTH: 3
<212> TYPE: DNA
<213> ORGANISM: Artificial Sequence
<220> FEATURE:
<223> OTHER INFORMATION: sequencing result

<400> SEQUENCE: 180 cca                                                                   3

<210> SEQ ID NO 181
<211> LENGTH: 63
<212> TYPE: DNA
<213> ORGANISM: Artificial Sequence
<220> FEATURE:
<223> OTHER INFORMATION: sequencing result

<400> SEQUENCE: 181
gatgtccatg ccggttacac aggccagtat gtaattctac gccgccaatg gtggagagga    60
gga                                                                  63

<210> SEQ ID NO 182
<211> LENGTH: 72
<212> TYPE: DNA
<213> ORGANISM: Artificial Sequence
<220> FEATURE:
<223> OTHER INFORMATION: sequencing result

<400> SEQUENCE: 182
gatgtccatg ccggttacac aggccggtac ctcccccatg taattctacg ccgccaatgg    60
tggagaggag ga                                                        72

<210> SEQ ID NO 183
<211> LENGTH: 72
<212> TYPE: DNA
<213> ORGANISM: Artificial Sequence
<220> FEATURE:
<223> OTHER INFORMATION: sequencing result

<400> SEQUENCE: 183
gatgtccatg ccggttacac aggccagtac ctcccccatg taattctacg ccgccaatgg    60
tggagaggag ga                                                        72

<210> SEQ ID NO 184
<211> LENGTH: 77
<212> TYPE: DNA
<213> ORGANISM: Artificial Sequence
```

```
<220> FEATURE:
<223> OTHER INFORMATION: sequencing result

<400> SEQUENCE: 184
gatgtccatg ccggttacac aggccagtgc ctcttctccc ccatgtaatt ctacgccgcc    60
aatggtggag aggagga                                                   77

<210> SEQ ID NO 185
<211> LENGTH: 77
<212> TYPE: DNA
<213> ORGANISM: Artificial Sequence
<220> FEATURE:
<223> OTHER INFORMATION: sequencing result

<400> SEQUENCE: 185
gatgtccatg ccggttacac aggccagtac ctcttctccc ccatgtaatt ctacgccgcc    60
aatggtggag aggagga                                                   77

<210> SEQ ID NO 186
<211> LENGTH: 76
<212> TYPE: DNA
<213> ORGANISM: Artificial Sequence
<220> FEATURE:
<223> OTHER INFORMATION: sequencing result

<400> SEQUENCE: 186
gagccactac aaccttcagc ccaccattct gcagagccag cagaggcagg caaagcagaa    60
acatcagaaa gctcag                                                    76

<210> SEQ ID NO 187
<211> LENGTH: 77
<212> TYPE: DNA
<213> ORGANISM: Artificial Sequence
<220> FEATURE:
<223> OTHER INFORMATION: sequencing result

<400> SEQUENCE: 187
gagccactac aaccttcagc ccaccattct gcaagagcca gcagaggcag gcaaagcaga    60
aacatcagaa agctcag                                                   77

<210> SEQ ID NO 188
<211> LENGTH: 77
<212> TYPE: DNA
<213> ORGANISM: Artificial Sequence
<220> FEATURE:
<223> OTHER INFORMATION: sequencing result

<400> SEQUENCE: 188
tgagccacta caaccttcag cccaccattc tgcagagcca gcagaggcag gcaaagcaga    60
aacatcagaa agctcag                                                   77

<210> SEQ ID NO 189
<211> LENGTH: 73
<212> TYPE: DNA
<213> ORGANISM: Artificial Sequence
<220> FEATURE:
<223> OTHER INFORMATION: sequencing result

<400> SEQUENCE: 189
tgagccacta caaccttcag cccaccattc tgcagagcca gcagaggcaa agcagaaaca    60
tcagaaagct cag                                                       73
```

```
<210> SEQ ID NO 190
<211> LENGTH: 77
<212> TYPE: DNA
<213> ORGANISM: Artificial Sequence
<220> FEATURE:
<223> OTHER INFORMATION: sequencing result

<400> SEQUENCE: 190
gcaggcaaag cagaaacatc agaaagctca ggctctgccc cagcagtgcc agaagcctcg      60
gcttccccca aacagcg                                                    77

<210> SEQ ID NO 191
<211> LENGTH: 74
<212> TYPE: DNA
<213> ORGANISM: Artificial Sequence
<220> FEATURE:
<223> OTHER INFORMATION: sequencing result

<400> SEQUENCE: 191
gcaggcaaag cagaaacatc agaaagctca ggctctgccc cagcagcaga agcctcggct      60
tcccccaaac agcg                                                       74

<210> SEQ ID NO 192
<211> LENGTH: 57
<212> TYPE: DNA
<213> ORGANISM: Artificial Sequence
<220> FEATURE:
<223> OTHER INFORMATION: sequencing result

<400> SEQUENCE: 192
gcaggcaaag cagaaacatc agaaagctca agaagcctcg gcttccccca aacagcg        57

<210> SEQ ID NO 193
<211> LENGTH: 47
<212> TYPE: DNA
<213> ORGANISM: Artificial Sequence
<220> FEATURE:
<223> OTHER INFORMATION: sequencing result

<400> SEQUENCE: 193
gcaggcaaag cagaaacatc agaaagctcg gcttccccca aacagcg                   47

<210> SEQ ID NO 194
<211> LENGTH: 66
<212> TYPE: DNA
<213> ORGANISM: Artificial Sequence
<220> FEATURE:
<223> OTHER INFORMATION: sequencing result

<400> SEQUENCE: 194
atccgtgacc ggggacctat gtatgatgac cccaccttgc ctgaaggttg gacacgaaag      60
cttaaa                                                                66

<210> SEQ ID NO 195
<211> LENGTH: 39
<212> TYPE: DNA
<213> ORGANISM: Artificial Sequence
<220> FEATURE:
<223> OTHER INFORMATION: sequencing result

<400> SEQUENCE: 195
atccgtgacc ggggacgatg ttggacacga aagcttaaa                            39
```

-continued

```
<210> SEQ ID NO 196
<211> LENGTH: 43
<212> TYPE: DNA
<213> ORGANISM: Artificial Sequence
<220> FEATURE:
<223> OTHER INFORMATION: sequencing result

<400> SEQUENCE: 196
atccgtgacc ggggacctat gtatgatgac acgaaagctt aaa                        43

<210> SEQ ID NO 197
<211> LENGTH: 77
<212> TYPE: DNA
<213> ORGANISM: Artificial Sequence
<220> FEATURE:
<223> OTHER INFORMATION: sequencing result

<400> SEQUENCE: 197
atccgtgacc ggggataata agctttcgtg aaggttggat aataagcttt cgtgaaggtt      60
ggacacgaaa gcttaaa                                                     77

<210> SEQ ID NO 198
<211> LENGTH: 77
<212> TYPE: DNA
<213> ORGANISM: Artificial Sequence
<220> FEATURE:
<223> OTHER INFORMATION: sequencing result

<400> SEQUENCE: 198
gagccactac aaccttcagc ccaccattct gcagagccag cagaggcagg caaagcagaa      60
acatcagaaa gctcagg                                                     77

<210> SEQ ID NO 199
<211> LENGTH: 61
<212> TYPE: DNA
<213> ORGANISM: Artificial Sequence
<220> FEATURE:
<223> OTHER INFORMATION: sequencing result

<400> SEQUENCE: 199
gagccactac aaccttcagc ccaccagagg caggcaaagc agaaacatca gaaagctcag      60
g                                                                      61

<210> SEQ ID NO 200
<211> LENGTH: 52
<212> TYPE: DNA
<213> ORGANISM: Artificial Sequence
<220> FEATURE:
<223> OTHER INFORMATION: sequencing result

<400> SEQUENCE: 200
gagccaaaga gccagcagag gcaggcaaag cagaaacatc agaaagctca gg              52

<210> SEQ ID NO 201
<211> LENGTH: 61
<212> TYPE: DNA
<213> ORGANISM: Artificial Sequence
<220> FEATURE:
<223> OTHER INFORMATION: sequencing result

<400> SEQUENCE: 201
gagccactac aaccttcagc ccagcagagg caggcaaagc agaaacatca gaaagctcag      60
g                                                                      61
```

-continued

<210> SEQ ID NO 202
<211> LENGTH: 77
<212> TYPE: DNA
<213> ORGANISM: Artificial Sequence
<220> FEATURE:
<223> OTHER INFORMATION: sequencing result

<400> SEQUENCE: 202
gcaggcaaag cagaaacatc agaaagctca ggctctgccc cagcagtgcc agaagcctcg    60 gcttcccca aacagcg                                                    77

<210> SEQ ID NO 203
<211> LENGTH: 74
<212> TYPE: DNA
<213> ORGANISM: Artificial Sequence
<220> FEATURE:
<223> OTHER INFORMATION: sequencing result

<400> SEQUENCE: 203
gcaggcaaag cagaaacatc agaaagctca ggcttttga caacatagag agcctcggct      60
tcccccaaac agcg                                                      74

<210> SEQ ID NO 204
<211> LENGTH: 73
<212> TYPE: DNA
<213> ORGANISM: Artificial Sequence
<220> FEATURE:
<223> OTHER INFORMATION: sequencing result

<400> SEQUENCE: 204
gcaggcaaag cagaaacatc agaaagctca ggctctgccc cagcagttaa gcctcggctt    60
cccccaaaca gcg                                                       73

<210> SEQ ID NO 205
<211> LENGTH: 71
<212> TYPE: DNA
<213> ORGANISM: Artificial Sequence
<220> FEATURE:
<223> OTHER INFORMATION: sequencing result

<400> SEQUENCE: 205
gcaggcaaag cagaaacatc agaaagctca ggctctgccc cagcagaagc ctcggcttcc    60
cccaaacagc g                                                         71

<210> SEQ ID NO 206
<211> LENGTH: 70
<212> TYPE: DNA
<213> ORGANISM: Artificial Sequence
<220> FEATURE:
<223> OTHER INFORMATION: sequencing result

<400> SEQUENCE: 206
gcaggcaaag cagaaacatc agaaagctca ggctctgccc cagcgaagcc tcggcttccc    60
ccaaacagcg                                                           70

<210> SEQ ID NO 207
<211> LENGTH: 65
<212> TYPE: DNA
<213> ORGANISM: Artificial Sequence
<220> FEATURE:
<223> OTHER INFORMATION: sequencing result

<400> SEQUENCE: 207

```
gcaggcaaag cagaaacatc agaaagctca ggctctgccc cagcctcggc ttcccccaaa    60
cagcg                                                                65

<210> SEQ ID NO 208
<211> LENGTH: 62
<212> TYPE: DNA
<213> ORGANISM: Artificial Sequence
<220> FEATURE:
<223> OTHER INFORMATION: sequencing result

<400> SEQUENCE: 208
gcaggcaaag cagaaacatc agaaagctca ggctcagaag cctcggcttc cccaaacag     60 cg                                                                   62

<210> SEQ ID NO 209
<211> LENGTH: 77
<212> TYPE: DNA
<213> ORGANISM: Artificial Sequence
<220> FEATURE:
<223> OTHER INFORMATION: sequencing result

<400> SEQUENCE: 209
atccgtgacc ggggacctat gtatgatgac cccaccttgc ctgaaggttg gacacgaaag    60
cttaaacaaa ggaagtc                                                   77

<210> SEQ ID NO 210
<211> LENGTH: 55
<212> TYPE: DNA
<213> ORGANISM: Artificial Sequence
<220> FEATURE:
<223> OTHER INFORMATION: sequencing result

<400> SEQUENCE: 210
atccgtgacc ggggacctat gtatgatgac cacgaaagct taaacaaagg aagtc         55

<210> SEQ ID NO 211
<211> LENGTH: 77
<212> TYPE: DNA
<213> ORGANISM: Artificial Sequence
<220> FEATURE:
<223> OTHER INFORMATION: sequencing result

<400> SEQUENCE: 211
gagccactac aaccttcagc ccaccattct gcagagccag cagaggcagg caaagcagaa    60
acatcagaaa gctcagg                                                   77

<210> SEQ ID NO 212
<211> LENGTH: 73
<212> TYPE: DNA
<213> ORGANISM: Artificial Sequence
<220> FEATURE:
<223> OTHER INFORMATION: sequencing result

<400> SEQUENCE: 212
gagccactac aaccttcagc ccatctgcag agccagcaga ggcaggcaaa gcagaaacat    60
cagaaagctc agg                                                       73

<210> SEQ ID NO 213
<211> LENGTH: 56
<212> TYPE: DNA
<213> ORGANISM: Artificial Sequence
<220> FEATURE:
```

<223> OTHER INFORMATION: sequencing result

<400> SEQUENCE: 213

```
gagccactac aaccttcagc agaggcaggc aaagcagaaa catcagaaag ctcagg      56
```

<210> SEQ ID NO 214
<211> LENGTH: 77
<212> TYPE: DNA
<213> ORGANISM: Artificial Sequence
<220> FEATURE:
<223> OTHER INFORMATION: sequencing result

<400> SEQUENCE: 214

```
tgagccacta caaccttcag cccaccattc tgcagagcca gcagaggcag gcaaagcaga   60
aacatcagaa agctcag                                                 77
```

<210> SEQ ID NO 215
<211> LENGTH: 62
<212> TYPE: DNA
<213> ORGANISM: Artificial Sequence
<220> FEATURE:
<223> OTHER INFORMATION: sequencing result

<400> SEQUENCE: 215

```
tgagccacta caaccttcag cccaccattc tgcagagcca gcagaaacat cagaaagctc   60
ag                                                                 62
```

<210> SEQ ID NO 216
<211> LENGTH: 61
<212> TYPE: DNA
<213> ORGANISM: Artificial Sequence
<220> FEATURE:
<223> OTHER INFORMATION: sequencing result

<400> SEQUENCE: 216

```
catcagaaag ctcaggctct gccccagcag tgccagaagc ctcggcttcc cccaaacagc   60
g                                                                  61
```

<210> SEQ ID NO 217
<211> LENGTH: 77
<212> TYPE: DNA
<213> ORGANISM: Artificial Sequence
<220> FEATURE:
<223> OTHER INFORMATION: sequencing result

<400> SEQUENCE: 217

```
catcagaaag ctcaggctct gccccacgca cacacacatt gtacacattg cactgcctcg   60 gcttcccccca aacagcg                                                77
```

<210> SEQ ID NO 218
<211> LENGTH: 57
<212> TYPE: DNA
<213> ORGANISM: Artificial Sequence
<220> FEATURE:
<223> OTHER INFORMATION: sequencing result

<400> SEQUENCE: 218

```
catcagaaag ctcaggctct gccccagcac agaagcctcg gcttccccca aacagcg      57
```

<210> SEQ ID NO 219
<211> LENGTH: 77
<212> TYPE: DNA
<213> ORGANISM: Artificial Sequence

```
<220> FEATURE:
<223> OTHER INFORMATION: sequencing result

<400> SEQUENCE: 219
atccgtgacc ggggacctat gtatgatgac cccaccttgc ctgaaggttg gacacgaaag      60
cttaaacaaa ggaagtc                                                    77

<210> SEQ ID NO 220
<211> LENGTH: 53
<212> TYPE: DNA
<213> ORGANISM: Artificial Sequence
<220> FEATURE:
<223> OTHER INFORMATION: sequencing result

<400> SEQUENCE: 220
atccgtgacc gggggcctga aggttggaca cgaaagctta acaaaggaa gtc             53

<210> SEQ ID NO 221
<211> LENGTH: 72
<212> TYPE: DNA
<213> ORGANISM: Artificial Sequence
<220> FEATURE:
<223> OTHER INFORMATION: sequencing result

<400> SEQUENCE: 221
atccgtgacc ggggacctat gtatgatgac cctgcctgaa ggttggacac gaaagcttaa     60
acaaaggaag tc                                                        72

<210> SEQ ID NO 222
<211> LENGTH: 57
<212> TYPE: DNA
<213> ORGANISM: Artificial Sequence
<220> FEATURE:
<223> OTHER INFORMATION: sequencing result

<400> SEQUENCE: 222
atccgtgacc ggggacctat gtatgggttg gacacgaaag cttaaacaaa ggaagtc       57

<210> SEQ ID NO 223
<211> LENGTH: 77
<212> TYPE: DNA
<213> ORGANISM: Artificial Sequence
<220> FEATURE:
<223> OTHER INFORMATION: sequencing result

<400> SEQUENCE: 223
gagccactac aaccttcagc ccaccattct gcagagccag cagaggcagg caaagcagaa     60
acatcagaaa gctcagg                                                    77

<210> SEQ ID NO 224
<211> LENGTH: 68
<212> TYPE: DNA
<213> ORGANISM: Artificial Sequence
<220> FEATURE:
<223> OTHER INFORMATION: sequencing result

<400> SEQUENCE: 224
gagccactac aaccttcagc ccaccattca gcagaggcag gcaaagcaga acatcagaa      60 agctcagg                                                              68

<210> SEQ ID NO 225
<211> LENGTH: 77
<212> TYPE: DNA
```

```
<213> ORGANISM: Artificial Sequence
<220> FEATURE:
<223> OTHER INFORMATION: sequencing result

<400> SEQUENCE: 225
tgagccacta caaccttcag cccaccattc tgcagagcca gcagaggcag gcaaagcaga    60
aacatcagaa agctcag                                                  77

<210> SEQ ID NO 226
<211> LENGTH: 71
<212> TYPE: DNA
<213> ORGANISM: Artificial Sequence
<220> FEATURE:
<223> OTHER INFORMATION: sequencing result

<400> SEQUENCE: 226
tgagccacta caaccttcag cccaccattc tgcagagcca gcagaggcag cagaaacatc    60
agaaagctca g                                                        71

<210> SEQ ID NO 227
<211> LENGTH: 77
<212> TYPE: DNA
<213> ORGANISM: Artificial Sequence
<220> FEATURE:
<223> OTHER INFORMATION: sequencing result

<400> SEQUENCE: 227
atccgtgacc ggggacctat gtatgatgac cccaccttgc ctgaaggttg gacacgaaag    60
cttaaacaaa ggaagtc                                                  77

<210> SEQ ID NO 228
<211> LENGTH: 71
<212> TYPE: DNA
<213> ORGANISM: Artificial Sequence
<220> FEATURE:
<223> OTHER INFORMATION: sequencing result

<400> SEQUENCE: 228
atccgtgacc ggggacctat gtatgatgcc cccccgaag gttggacacg aaagcttaaa    60
caaaggaagt c                                                        71

<210> SEQ ID NO 229
<211> LENGTH: 23
<212> TYPE: DNA
<213> ORGANISM: Artificial Sequence
<220> FEATURE:
<223> OTHER INFORMATION: Human Dnmt1 Target site 1

<400> SEQUENCE: 229
cctcactcct gctcggtgaa ttt                                           23

<210> SEQ ID NO 230
<211> LENGTH: 23
<212> TYPE: DNA
<213> ORGANISM: Artificial Sequence
<220> FEATURE:
<223> OTHER INFORMATION: Human Dnmt1 Target site 2

<400> SEQUENCE: 230
aggagtgttc agtctccgtg aac                                           23

<210> SEQ ID NO 231
<211> LENGTH: 23
```

```
<212> TYPE: DNA
<213> ORGANISM: Artificial Sequence
<220> FEATURE:
<223> OTHER INFORMATION: Human Dnmt1 Target site 3

<400> SEQUENCE: 231
ctgatggtcc atgtctgtta ctc                                              23

<210> SEQ ID NO 232
<211> LENGTH: 23
<212> TYPE: DNA
<213> ORGANISM: Artificial Sequence
<220> FEATURE:
<223> OTHER INFORMATION: Mouse MeCP2 Target site 1

<400> SEQUENCE: 232
cctgcctctg ctggctctgc aga                                              23

<210> SEQ ID NO 233
<211> LENGTH: 23
<212> TYPE: DNA
<213> ORGANISM: Artificial Sequence
<220> FEATURE:
<223> OTHER INFORMATION: Mouse MeCP2 Target site 2

<400> SEQUENCE: 233
tgatgtttct gctttgcctg cct                                              23

<210> SEQ ID NO 234
<211> LENGTH: 23
<212> TYPE: DNA
<213> ORGANISM: Artificial Sequence
<220> FEATURE:
<223> OTHER INFORMATION: Mouse MeCP2 Target site 3

<400> SEQUENCE: 234
ggggaagccg aggcttctgg cac                                              23

<210> SEQ ID NO 235
<211> LENGTH: 23
<212> TYPE: DNA
<213> ORGANISM: Artificial Sequence
<220> FEATURE:
<223> OTHER INFORMATION: Mouse MeCP2 Target site 4

<400> SEQUENCE: 235
gtgtccaacc ttcaggcaag gtg                                              23

<210> SEQ ID NO 236
<211> LENGTH: 23
<212> TYPE: DNA
<213> ORGANISM: Artificial Sequence
<220> FEATURE:
<223> OTHER INFORMATION: Mouse MeCP2 Target site 5

<400> SEQUENCE: 236
gcctgcctct gctggctctg cag                                              23

<210> SEQ ID NO 237
<211> LENGTH: 23
<212> TYPE: DNA
<213> ORGANISM: Artificial Sequence
<220> FEATURE:
<223> OTHER INFORMATION: Mouse MeCP2 Target site 6

<400> SEQUENCE: 237
```

```
ctgatgtttc tgctttgcct gcc                                             23
```

<210> SEQ ID NO 238
<211> LENGTH: 23
<212> TYPE: DNA
<213> ORGANISM: Artificial Sequence
<220> FEATURE:
<223> OTHER INFORMATION: Mouse MeCP2 Target site 7

<400> SEQUENCE: 238

```
gggggaagcc gaggcttctg gca                                             23
```

<210> SEQ ID NO 239
<211> LENGTH: 23
<212> TYPE: DNA
<213> ORGANISM: Artificial Sequence
<220> FEATURE:
<223> OTHER INFORMATION: Mouse MeCP2 Target site 8

<400> SEQUENCE: 239

```
cgtgtccaac cttcaggcaa ggt                                             23
```

<210> SEQ ID NO 240
<211> LENGTH: 23
<212> TYPE: DNA
<213> ORGANISM: Artificial Sequence
<220> FEATURE:
<223> OTHER INFORMATION: Mouse Tet1 Target site 1

<400> SEQUENCE: 240

```
tcgggtcagc atcactggct cag                                             23
```

<210> SEQ ID NO 241
<211> LENGTH: 23
<212> TYPE: DNA
<213> ORGANISM: Artificial Sequence
<220> FEATURE:
<223> OTHER INFORMATION: Mouse Tet1 Target site 2

<400> SEQUENCE: 241

```
ctgggagcag cctgagaacc ctg                                             23
```

<210> SEQ ID NO 242
<211> LENGTH: 23
<212> TYPE: DNA
<213> ORGANISM: Artificial Sequence
<220> FEATURE:
<223> OTHER INFORMATION: Mouse Tet1 Target site 3

<400> SEQUENCE: 242

```
acatcagctg agccagtgat gct                                             23
```

<210> SEQ ID NO 243
<211> LENGTH: 23
<212> TYPE: DNA
<213> ORGANISM: Artificial Sequence
<220> FEATURE:
<223> OTHER INFORMATION: Mouse Tet1 Target site 4

<400> SEQUENCE: 243

```
gattcttgca gtaggtgcac tcc                                             23
```

<210> SEQ ID NO 244
<211> LENGTH: 23
<212> TYPE: DNA
<213> ORGANISM: Artificial Sequence

```
<220> FEATURE:
<223> OTHER INFORMATION: Mouse Tet1 Target site 5

<400> SEQUENCE: 244
ctcttcttac agatctggtg gct                                              23

<210> SEQ ID NO 245
<211> LENGTH: 23
<212> TYPE: DNA
<213> ORGANISM: Artificial Sequence
<220> FEATURE:
<223> OTHER INFORMATION: Mouse Tet1 Target site 6

<400> SEQUENCE: 245
ctcgggtcag catcactggc tca                                              23

<210> SEQ ID NO 246
<211> LENGTH: 23
<212> TYPE: DNA
<213> ORGANISM: Artificial Sequence
<220> FEATURE:
<223> OTHER INFORMATION: Mouse Tet1 Target site 7

<400> SEQUENCE: 246
cacaggccag tacctcttct ccc                                              23

<210> SEQ ID NO 247
<211> LENGTH: 23
<212> TYPE: DNA
<213> ORGANISM: Artificial Sequence
<220> FEATURE:
<223> OTHER INFORMATION: Mouse Tet1 Target site 8

<400> SEQUENCE: 247
cgattcttgc agtaggtgca ctc                                              23

<210> SEQ ID NO 248
<211> LENGTH: 23
<212> TYPE: DNA
<213> ORGANISM: Artificial Sequence
<220> FEATURE:
<223> OTHER INFORMATION: Human AAVS1 Target site 1

<400> SEQUENCE: 248
tgagaatggt gcgtcctagg tgt                                              23

<210> SEQ ID NO 249
<211> LENGTH: 23
<212> TYPE: DNA
<213> ORGANISM: Artificial Sequence
<220> FEATURE:
<223> OTHER INFORMATION: Human AAVS1 Target site 2

<400> SEQUENCE: 249
gtgagaatgg tgcgtcctag gtg                                              23

<210> SEQ ID NO 250
<211> LENGTH: 23
<212> TYPE: DNA
<213> ORGANISM: Artificial Sequence
<220> FEATURE:
<223> OTHER INFORMATION: Human AAVS1 Target site 3

<400> SEQUENCE: 250
accaggtcgt ggccgcctct act                                              23
```

```
<210> SEQ ID NO 251
<211> LENGTH: 23
<212> TYPE: DNA
<213> ORGANISM: Artificial Sequence
<220> FEATURE:
<223> OTHER INFORMATION: Human AAVS1 Target site 4

<400> SEQUENCE: 251
tgtggaaaac tccctttgtg aga                                            23

<210> SEQ ID NO 252
<211> LENGTH: 23
<212> TYPE: DNA
<213> ORGANISM: Artificial Sequence
<220> FEATURE:
<223> OTHER INFORMATION: Human AAVS1 Target site 5

<400> SEQUENCE: 252
ctactcccTT tctctttctc cat                                            23

<210> SEQ ID NO 253
<211> LENGTH: 23
<212> TYPE: DNA
<213> ORGANISM: Artificial Sequence
<220> FEATURE:
<223> OTHER INFORMATION: Human AAVS1 Target site 6

<400> SEQUENCE: 253
tgtccccctt cctcgtccac cat                                            23

<210> SEQ ID NO 254
<211> LENGTH: 23
<212> TYPE: DNA
<213> ORGANISM: Artificial Sequence
<220> FEATURE:
<223> OTHER INFORMATION: Human AAVS1 Target site 7

<400> SEQUENCE: 254
cctttgtgag aatggtgcgt cct                                            23

<210> SEQ ID NO 255
<211> LENGTH: 23
<212> TYPE: DNA
<213> ORGANISM: Artificial Sequence
<220> FEATURE:
<223> OTHER INFORMATION: Human AAVS1 Target site 8

<400> SEQUENCE: 255
ctacaggggt tcctggctct gct                                            23

<210> SEQ ID NO 256
<211> LENGTH: 23
<212> TYPE: DNA
<213> ORGANISM: Artificial Sequence
<220> FEATURE:
<223> OTHER INFORMATION: Mouse Apob Target site 12

<400> SEQUENCE: 256
gtgggcccat ggcggatgga tgg                                            23

<210> SEQ ID NO 257
<211> LENGTH: 23
<212> TYPE: DNA
<213> ORGANISM: Artificial Sequence
<220> FEATURE:
<223> OTHER INFORMATION: Mouse Nrl Target site 1
```

```
<400> SEQUENCE: 257
cctcccagtc ccttggctat gga                                              23

<210> SEQ ID NO 258
<211> LENGTH: 23
<212> TYPE: DNA
<213> ORGANISM: Artificial Sequence
<220> FEATURE:
<223> OTHER INFORMATION: Mouse Nrl Target site 7

<400> SEQUENCE: 258
ggctccacac catacagctc ggt                                              23
```

SYSTEM AND METHOD FOR GENOME EDITING

CROSS-REFERENCE TO RELATED APPLICATIONS

This application is a U.S. National Phase application of International Application No. PCT/CN2018/082446, filed Apr. 10, 2018, which claims priority to Chinese Application No. 201710228595.X filed Apr. 10, 2017, each of which are incorporated herein by reference in their entireties.

SEQUENCE LISTING DISCLOSURE

This application includes as part of its disclosure a biological sequence listing which is being concurrently submitted through EFS-Web. Said biological sequence listing is contained in a file named "11584980001401.txt" which was created on Jan. 9, 2023, and has a size of 234,496 bytes, and is hereby incorporated by reference in its entirety.

TECHNICAL FIELD

The invention relates to the field of genetic engineering. In particular, the present invention relates to a novel eukaryotic genome editing system and method. More specifically, the present invention relates to a CRISPR-Cpf1 system capable of efficiently editing a genome of a eukaryotic cell and the use thereof.

BACKGROUND

The CRISPR (Clustered regular interspaced short palindromic repeats) system is an immune system that is generated during the evolution of bacteria to protect against foreign gene invasion. Among them, the type II CRISPR-Cas9 system is a system for DNA cleavage by a Cas9 protein mediated by two small RNAs (crRNA and tracrRNA) or an artificially synthetized small RNA (sgRNA), and is the simplest one of the three first discovered (Type I, II, III) CRISPR systems. Due to its ease of operation, the system was successfully engineered in 2013 and successfully achieved eukaryotic genome editing. The CRISPR/Cas9 system quickly became the most popular technology in life sciences.

In 2015, Zhang et al. discovered a new gene editing system through sequence alignment and systematic analysis, the CRISPR-Cpf1 system, which is different from the CRISPR-Cas9 system. The system requires only one small RNA (crRNA) to mediate genome editing. There are thousands of CRISPR systems in nature, but only a few can successfully implement eukaryotic genome editing.

There is still a need in the art for a CRISPR-Cpf1 system that enables efficient eukaryotic genome editing.

SUMMARY OF THE INVENTION

In one aspect, the present invention provides a genome editing system for site-directed modification of a target sequence in the genome of a cell, comprising at least one of the following i) to v):

i) a Cpf1 protein, and a guide RNA;
ii) an expression construct comprising a nucleotide sequence encoding a Cpf1 protein, and a guide RNA;
iii) a Cpf1 protein, and an expression construct comprising a nucleotide sequence encoding a guide RNA;
iv) an expression construct comprising a nucleotide sequence encoding a Cpf1 protein, and an expression construct comprising a nucleotide sequence encoding a guide RNA;
v) an expression construct comprising a nucleotide sequence encoding a Cpf1 protein and a nucleotide sequence encoding a guide RNA;

wherein the Cpf1 protein comprises an amino acid sequence of SEQ ID NOs: 1-12 or an amino acid sequence having at least 80% sequence identity to one of SEQ ID NOs: 1-12, the guide RNA capable of targeting the Cpf1 protein to a target sequence in the genome of the cell.

In a second aspect, the present invention provides a method of modifying a target sequence in the genome of a cell, comprising introducing the genome editing system of the invention into the cell, whereby the guide RNA targets the Cpf1 protein to the target sequence in the genome of the cell, resulting in substitution, deletion and/or addition of one or more nucleotides in the target sequence.

In a third aspect, the invention provides a method of treating a disease in a subject in need thereof, comprising delivering to the subject an effective amount of the genome editing system of the invention to modify a gene related with the disease.

In a fourth aspect, the invention provides the use of the genome editing system of the invention for the preparation of a pharmaceutical composition for treating a disease in a subject in need thereof, wherein the genome editing system is for modifying a gene related with the disease.

In a fifth aspect, the invention provides a pharmaceutical composition for treating a disease in a subject in need thereof, comprising the genome editing system of the invention and a pharmaceutically acceptable carrier, wherein the genome editing system is for modifying a gene related with the disease.

In a sixth aspect, the invention provides a crRNA, comprises a crRNA scaffold sequence corresponding to any one of SEQ ID NOs: 25-33 or the coding sequence of which comprises a sequence set forth in any one of SEQ ID NOs: 25-33.

DESCRIPTION OF THE DRAWINGS

FIG. 6. In vitro assay of PAM sequences of BsCpf1. A: *E. coli* expression and purification of BsCpf1 protein. B-E: Targeting BsCpf1 using 5'-TTN PAM.

FIG. 8. shows the ability of HkCpf1 to edit 8 sites of the human AAVS1 gene. A: The results of T7EI assay. B: Sequencing results show that HkCpf1 was able to generate mutations at seven sites, and the PAM sequence is 5'-YYN, which is consistent with the results in FIG. 7.

FIGS. 9, 10 and 11 show that the four Cpf1 proteins edited the mouse genome in EpiSC cells.

FIGS. 13-14 illustrate the optimization of the crRNA scaffold sequence.

DETAILED DESCRIPTION OF THE INVENTION

1. Definition

Figure 1:
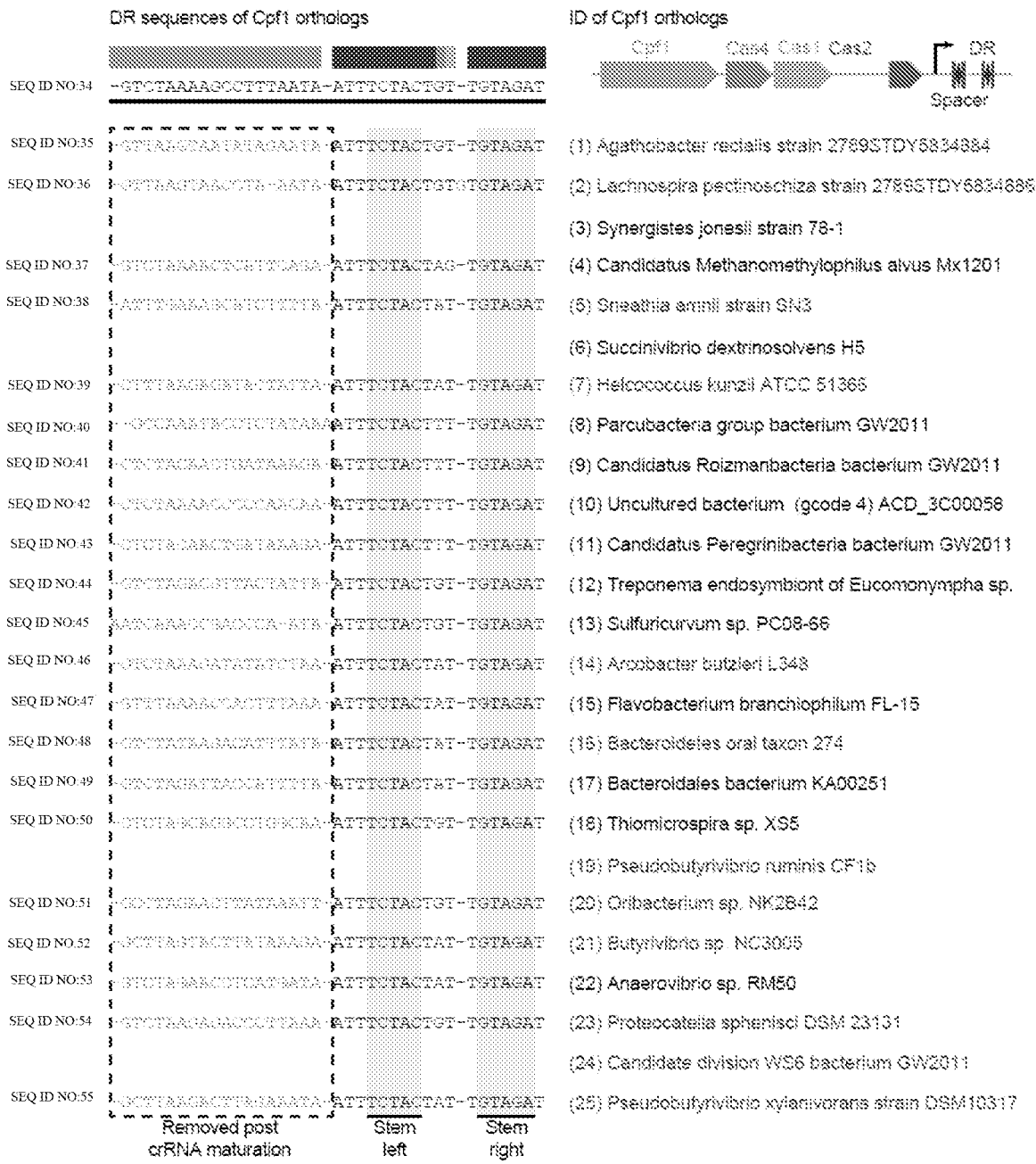
FIG. 1. Alignment of direct repeat sequences (DR) from 25 new Cpf1 family proteins. The stem duplexes of the 21 mature crRNAs with DR sequences are extremely conserved.

In the present invention, the scientific and technical terms used herein have the meaning as commonly understood by a person skilled in the art unless otherwise specified. Also, the protein and nucleic acid chemistry, molecular biology, cell and tissue culture, microbiology, immunology related terms, and laboratory procedures used herein are terms and routine steps that are widely used in the corresponding field. For example, standard recombinant DNA and molecular cloning techniques used in the present invention are well known to those skilled in the art and are more fully described in the following document: Sambrook, J., Fritsch, E. F. and Maniatis, T., Molecular Cloning: A Laboratory Manual; Cold Spring Harbor Laboratory Press: Cold Spring Harbor, 1989 (hereinafter referred to as "Sambrook"). In the meantime, in order to better understand the present invention, definitions and explanations of related terms are provided below.

"Cpf1 nuclease", "Cpf1 protein" and "Cpf1" are used interchangeably herein and refer to an RNA-directed nuclease comprising a Cpf1 protein or a fragment thereof. Cpf1 is a component of the CRISPR-Cpf1 genome editing system that targets and cleaves DNA target sequences to form DNA double-strand breaks (DSBs) under the guidance of a guide RNA (crRNA). DSB can activate the intrinsic repair mechanism in the living cell, non-homologous end joining (NHEJ) and homologous recombination (HR), to repair DNA damage in the cell, during which site-directed editing is achieved to the specific DNA sequence.

"guide RNA" and "gRNA" can be used interchangeably herein. The guide RNA of the CRISPR-Cpf1 genome editing system is typically composed only of crRNA molecules, wherein the crRNA comprises a sequence that is sufficiently identical to the target sequence to hybridize to the complement of the target sequence and direct the complex (Cpf1+crRNA) to sequence-specifically bind to the target sequence.

"Genome" as used herein encompasses not only chromosomal DNA present in the nucleus, but also organellar DNA present in the subcellular components (e.g., mitochondria, plastids) of the cell.

As used herein, "organism" includes any organism that is suitable for genomic editing, eukaryotes are preferred. Examples of organisms include, but are not limited to, mammals such as human, mouse, rat, monkey, dog, pig, sheep, cattle, cat; poultry such as chicken, duck, goose; plants including monocots and dicots such as rice, corn, wheat, sorghum, barley, soybean, peanut, *arabidopsis* and the like.

A "genetically modified organism" or "genetically modified cell" includes an organism or a cell which comprises within its genome an exogenous polynucleotide or a modified gene or expression regulatory sequence. For example, the exogenous polynucleotide is stably integrated within the genome of the organism or the cell such that the polynucleotide is passed on to successive generations. The exogenous polynucleotide may be integrated into the genome alone or as part of a recombinant DNA construct. The modified gene or expression regulatory sequence means that, in the organism genome or the cell genome, said sequence comprises one or more nucleotide substitution, deletion, or addition.

"Exogenous" in reference to a sequence means a sequence from a foreign species, or refers to a sequence in which significant changes in composition and/or locus occur from its native form through deliberate human intervention if from the same species.

"Polynucleotide", "nucleic acid sequence", "nucleotide sequence" or "nucleic acid fragment" are used interchangeably and are single-stranded or double-stranded RNA or DNA polymers, optionally containing synthetic, non-natural or altered nucleotide bases. Nucleotides are referred to by their single letter names as follows: "A" is adenosine or deoxyadenosine (corresponding to RNA or DNA, respectively), "C" means cytidine or deoxycytidine, "G" means guanosine or deoxyguanosine, "U" represents uridine, "T" means deoxythymidine, "R" means purine (A or G), "Y" means pyrimidine (C or T), "K" means G or T, "H" means A or C or T, "I" means inosine, and "N" means any nucleotide.

"Polypeptide," "peptide," and "protein" are used interchangeably in the present invention to refer to a polymer of amino acid residues. The terms apply to an amino acid polymer in which one or more amino acid residues is artificial chemical analogue of corresponding naturally occurring amino acid(s), as well as to a naturally occurring amino acid polymer. The terms "polypeptide," "peptide," "amino acid sequence," and "protein" may also include modified forms including, but not limited to, glycosylation, lipid ligation, sulfation, γ carboxylation of glutamic acid residues, and ADP-ribosylation.

Sequence "identity" has recognized meaning in the art, and the percentage of sequence identity between two nucleic acids or polypeptide molecules or regions can be calculated using the disclosed techniques. Sequence identity can be measured along the entire length of a polynucleotide or polypeptide or along a region of the molecule. (See, for example, *Computational Molecular Biology*, Lesk, A. M., ed., Oxford University Press, New York, 1988; *Biocomputing: Informatics and Genome Projects*, Smith, D. W., ed., Academic Press, New York, 1993; *Computer Analysis of Sequence Data*, Part I, Griffin, A. M., and Griffin, H. G., eds., Humana Press, New Jersey, 1994; *Sequence Analysis in Molecular Biology*, von Heinje, G., Academic Press, 1987; and Sequence Analysis Primer, Gribskov, M. and Devereux, J., eds., M Stockton Press, New York, 1991). Although there are many methods for measuring the identity between two polynucleotides or polypeptides, the term "identity" is well known to the skilled person (Carrillo, H. & Lipman, D., *SIAM J Applied Math* 48: 1073 (1988)).

Suitable conserved amino acid replacements in peptides or proteins are known to those skilled in the art and can generally be carried out without altering the biological activity of the resulting molecule. In general, one skilled in the art recognizes that a single amino acid replacement in a non-essential region of a polypeptide does not substantially alter biological activity (See, for example, Watson et al., *Molecular Biology of the Gene*, 4th Edition, 1987, The Benjamin/Cummings Pub. co., p. 224).

As used in the present invention, "expression construct" refers to a vector such as a recombinant vector that is suitable for expression of a nucleotide sequence of interest in an organism. "Expression" refers to the production of a functional product. For example, expression of a nucleotide sequence may refer to the transcription of a nucleotide sequence (e.g., transcription to produce mRNA or functional RNA) and/or the translation of an RNA into a precursor or mature protein.

The "expression construct" of the present invention may be a linear nucleic acid fragment, a circular plasmid, a viral vector or, in some embodiments, an RNA that is capable of translation (such as mRNA).

The "expression construct" of the present invention may comprise regulatory sequences and nucleotide sequences of interest from different origins, or regulatory sequences and nucleotide sequences of interest from the same source but arranged in a manner different from that normally occurring in nature.

"Regulatory sequence" and "regulatory element" are used interchangeably to refer to a nucleotide sequence that is located upstream (5 'non-coding sequence), middle or downstream (3' non-coding sequence) of a coding sequence and affects the transcription, RNA processing or stability or translation of the relevant coding sequence. Regulatory sequences may include, but are not limited to, promoters, translation leaders, introns and polyadenylation recognition sequences.

"Promoter" refers to a nucleic acid fragment capable of controlling the transcription of another nucleic acid fragment. In some embodiments of the present invention, the promoter is a promoter capable of controlling the transcription of a gene in a cell, whether or not it is derived from the cell. The promoter may be a constitutive promoter or tissue-specific promoter or developmentally-regulated promoter or inducible promoter.

"Constitutive promoter" refers to a promoter that may in general cause the gene to be expressed in most cases in most cell types. "Tissue-specific promoter" and "tissue-preferred promoter" are used interchangeably and mean that they are expressed primarily but not necessarily exclusively in one tissue or organ, but also in a specific cell or cell type. "Developmentally-regulated promoter" refers to a promoter whose activity is dictated by developmental events. "Inducible promoter" selectively express operably linked DNA sequences in response to an endogenous or exogenous stimulus (environment, hormones, chemical signals, etc.).

As used herein, the term "operably linked" refers to the linkage of a regulatory element (e.g., but not limited to, a promoter sequence, a transcription termination sequence, etc.) to a nucleic acid sequence (e.g., a coding sequence or an open reading frame) such that transcription of the nucleotide sequence is controlled and regulated by the transcriptional regulatory element. Techniques for operably linking regulatory element regions to nucleic acid molecules are known in the art.

"Introduction" of a nucleic acid molecule (e.g., plasmid, linear nucleic acid fragment, RNA, etc.) or protein into an organism means that the nucleic acid or protein is used to transform an organism cell such that the nucleic acid or protein is capable of functioning in the cell. As used in the present invention, "transformation" includes both stable and transient transformations.

"Stable transformation" refers to the introduction of exogenous nucleotide sequences into the genome, resulting in the stable inheritance of foreign genes. Once stably transformed, the exogenous nucleic acid sequence is stably integrated into the genome of the organism and any of its successive generations.

"Transient transformation" refers to the introduction of a nucleic acid molecule or protein into a cell, performing a function without the stable inheritance of an exogenous gene. In transient transformation, the exogenous nucleic acid sequences are not integrated into the genome.

2. Efficient Genome Editing System

In one aspect, the invention provides the use of the Cpf1 protein comprises an amino acid sequences having at least 80%, at least 85%, at least 90%, at least 95%, at least 96%, at least 97%, at least 98%, at least 99%, even 100% sequence identity to one of SEQ ID NOs: 1-12 in eukaryotic genome editing.

In another aspect, the present invention provides a genome editing system for site-directed modification of a target sequence in the genome of a cell, comprising at least one of the following i) to v):

i) a Cpf1 protein, and a guide RNA;

ii) an expression construct comprising a nucleotide sequence encoding a Cpf1 protein, and a guide RNA;

iii) a Cpf1 protein, and an expression construct comprising a nucleotide sequence encoding a guide RNA;

iv) an expression construct comprising a nucleotide sequence encoding a Cpf1 protein, and an expression construct comprising a nucleotide sequence encoding a guide RNA;

v) an expression construct comprising a nucleotide sequence encoding a Cpf1 protein and a nucleotide sequence encoding a guide RNA;

wherein the Cpf1 protein comprises an amino acid sequence of SEQ ID NOs: 1-12 or an amino acid sequence having at least 80% sequence identity to one of SEQ ID NOs: 1-12, the guide RNA capable of targeting the Cpf1 protein to a target sequence in the genome of the cell.

In some embodiments of the methods of the invention, the guide RNA is a crRNA. In some embodiments, the coding sequence of the crRNA comprises a crRNA scaffold sequence set forth in any one of SEQ ID NOs: 25-33. In some preferred embodiments, the crRNA scaffold sequence is SEQ ID NO:30. In some embodiments, the coding sequence of the cRNA further comprises a sequence that specifically hybridizes to the complement of the target sequence (i.e., a spacer sequence) at 3' of the cRNA scaffold sequence.

In some embodiments, the crRNA is encoded by a nucleotide sequence selected from the group consisting of:

```
i)
5'-ATTTCTACtgttGTAGAT(SEQ ID NO: 25)-N_x-3';

ii)
5'-ATTTCTACtattGTAGAT(SEQ ID NO: 26)-N_x-3';
```

```
iii)
5'-ATTTCTACtactGTAGAT(SEQ ID NO: 27)-N_x-3';

iv)
5'-ATTTCTACtttgGTAGAT(SEQ ID NO: 28)-N_x-3';

v)
5'-ATTTCTACtagttGTAGAT(SEQ ID NO: 29)-N_x-3';

vi)
5'-ATTTCTACTATGGTAGAT(SEQ ID NO: 30)-N_x-3';

vii)
5'-ATTTCTACTGTCGTAGAT(SEQ ID NO: 31)-N_x-3';

viii)
5'-ATTTCTACTTGTGTAGAT(SEQ ID NO: 32)-N_x-3';
and ix)
5'-ATTTCTACTGTGGTAGAT(SEQ ID NO: 33)-N_x-3',
``` wherein Nx represents nucleotide sequence that consists of x consecutive nucleotides, N is independently selected from A, G, C and T; x is an integer of 18≤x≤35, preferably, x=23. In some embodiments, the sequence Nx (spacer sequence) is capable of specifically hybridizing to the complement of the target sequence.

In some embodiments of the methods of the invention, the cell is a eukaryotic cell, preferably a mammalian cell.

In some embodiments of the methods of the invention, the Cpf1 protein comprises an amino acid sequence having at least 80%, at least 85%, at least 90%, at least 95%, at least 96%, at least 97% of at least 98%, at least 99%, or even 100% sequence identity to one of SEQ ID NOs: 1-12. The Cpf1 protein is capable of targeting and/or cleaving target sequences in the genome of the cell through a crRNA.

In some embodiments of the methods of the invention, the Cpf1 protein comprises an amino acid sequence having one or more amino acid residue substitution, deletion or addition relative to one of SEQ ID NOs: 1-12. For example, the Cpf1 protein comprises an amino acid sequence having 1, 2, 3, 4, 5, 6, 7, 8, 9, 10 amino acid residues substitution, deletion or addition relative to one of SEQ ID NOs: 1-12. In some embodiments, the amino acid substitution is a conservative substitution. The Cpf1 protein is capable of targeting and/or cleaving target sequences in the cell genome through a crRNA.

The Cpf1 protein of the invention may be derived from a species selected from: *Agathobacter rectalis, Lachnospira pectinoschiza, Sneathia amnii, Helcococcus kunzii, Arcobacter butzleri, Bacteroidetes oral, Oribacterium* sp., *Butyrivibrio* sp., *Proteocatella sphenisci, Candidatus Dojkabacteria, Pseudobutyrivibrio xylanivorans, Pseudobutyrivibrio ruminis*.

In some preferred embodiments of the invention, the Cpf1 protein is derived from *Agathobacter rectalis* (ArCpf1), *Butyrivibrio* sp. (BsCpf1), *Helcococcus kunzii* (HkCpf1), *Lachnospira pectinoschiza* (LpCpf1), *Pseudobutyrivibrio ruminis* (PrCpf1) or *Pseudobutyrivibrio xylanivorans* (PxCpf1). In some preferred embodiments of the invention, the Cpf1 protein comprises an amino acid sequence selected from SEQ ID NO: 1, SEQ ID NO: 2, SEQ ID NO: 4, SEQ ID NO: 8, SEQ ID NO: 11, SEQ ID NO: 12.

In some embodiments of the present invention, the Cpf1 protein of the present invention further comprises a nuclear localization sequence (NLS). In general, one or more NLSs in the Cpf1 protein should have sufficient strength to drive the Cpf1 protein in the nucleus of the cell to accumulate to an amount for achieving genome editing. In general, the intensity of nuclear localization activity is determined by the number, location of the NLS, one or more specific NLSs used in the Cpf1 protein, or a combination of these factors.

In some embodiments of the present invention, the NLS of the Cpf1 protein of the present invention may be located at the N-terminus and/or C-terminus. In some embodiments, the Cpf1 protein comprises about 1, 2, 3, 4, 5, 6, 7, 8, 9, 10 or more NLSs. In some embodiments, the Cpf1 protein comprises about 1, 2, 3, 4, 5, 6, 7, 8, 9, 10 or more NLS at or near the N-terminus. In some embodiments, the Cpf1 protein comprises about 1, 2, 3, 4, 5, 6, 7, 8, 9, 10 or more NLSs at or near the C-terminus. In some embodiments, the Cpf1 protein comprises a combination of these, such as comprises one or more NLSs at the N-terminus and one or more NLSs at the C-terminus. When there is more than one NLS, each can be selected to be independent of other NLSs. In some preferred embodiments of the present invention, the Cpf1 protein comprises two NLSs, for example, the two NLSs are located at the N-terminus and the C-terminus, respectively.

In general, NLS consists of one or more short sequences of positively charged lysine or arginine exposed on the surface of the protein, but other types of NLS are also known. Non-limiting examples of NLS include: KKRKV (nucleotide sequence 5'-AAGAAGAGAAAGGTC-3'), PKKKRKV (nucleotide sequence 5'-CCAAGAAGAAGAGGAAGGTG-3' or CCAAAGAAGAAGAGGAAGGTT), or SGGSPKKKRKV (nucleotide sequence 5'-TCGGGGGGGAGCCCAAAGAAGAAGCGGAAGGTG-3').

Furthermore, depending on the location of the DNA to be edited, the Cpf1 proteins of the present invention may also include other localization sequences, such as cytoplasm localization sequences, chloroplast localization sequences, mitochondrial localization sequences, and the like.

To obtain efficient expression in the target cells, in some embodiments of the present invention, the nucleotide sequence encoding the Cpf1 protein is codon optimized for the organism from which the cell to be genome edited is derived.

Codon optimization refers to the replacement of at least one codon (e.g., about or more than about 1, 2, 3, 4, 5, 10, 15, 20, 25, 50 or more codons) of a native sequence by a codon that is used more frequently or most frequently in the gene of the host cell, modifying the nucleic acid sequence while maintaining the native amino acid sequence to enhance expression in the host cell of interest. Different species show specific preferences for certain codons of a particular amino acid. Codon preference (difference in codon usage between organisms) is often associated with the efficiency of translation of messenger RNA (mRNA), which is believed to depend on the nature of the translated codon and the availability of specific transfer RNA (tRNA) molecules. The advantages of selected tRNAs within cells generally reflect the most frequently used codons for peptide synthesis. Therefore, genes can be customized to be best gene expressed in a given organism based on codon optimization. The codon usage table can be easily obtained, for example, in the Codon Usage Database available at www.kazusa.orip/codon/, and these tables can be adjusted in different ways. See, Nakamura Y. et. al "Codon usage tabulated from the international DNA sequence databases: status for the year 2000 Nucl. Acids Res, 28: 292 (2000).

The organism from which the cell can be edited by the method of the present invention is derived preferably is eukaryote, including but not limited to mammals such as human, mouse, rat, monkey, dog, pig, sheep, cattle, cat; a poultry such as chicken, duck, goose; plants including monocots and dicots, such as rice, corn, wheat, sorghum, barley, soybean, peanut and *Arabidopsis thaliana* and so on.

In some embodiments of the invention, the nucleotide sequence encoding the Cpf1 protein is codon optimized for human. In some embodiments, the codon-optimized nucleotide sequence encoding the Cpf1 protein is selected from SEQ ID NOs: 13-24.

In some embodiments of the present invention, the nucleotide sequence encoding the Cpf1 protein and/or the nucleotide sequence encoding the guide RNA is operably linked to an expression regulatory element such as a promoter.

Examples of promoters that can be used in the present invention include, but are not limited to, the polymerase (pol) I, pol II or pol III promoters. Examples of the pol I promoter include the *gallus* RNA pol I promoter. Examples of the pol II promoters include, but are not limited to, the immediate-early cytomegalovirus (CMV) promoter, the Rous sarcoma virus long terminal repeat (RSV-LTR) promoter, and the immediate-early simian virus 40 (SV40) promoter. Examples of pol III promoters include the U6 and H1 promoters. An inducible promoter such as a metallothionein promoter can be used. Other examples of promoters include the T7 phage promoter, the T3 phage promoter, the β-galactosidase promoter, and the Sp6 phage promoter, and the like. Promoters that can be used in plants include, but are not limited to, cauliflower mosaic virus 35S promoter, maize Ubi-1 promoter, wheat U6 promoter, rice U3 promoter, maize U3 promoter, rice actin promoter.

In another aspect, the invention provides a crRNA, comprises a crRNA scaffold sequence corresponding to any one of SEQ ID NOs: 25-33. In some embodiments, the coding sequence of the crRNA comprises the crRNA scaffold sequence set forth in any one of SEQ ID NOs: 25-33. In some preferred embodiments, the crRNA scaffold sequence is SEQ ID NO:30. In some embodiments, the coding sequence of the cRNA further comprises a sequence that specifically hybridizes to the complement of the target sequence (i.e., a spacer sequence) at 3' of the cRNA scaffold sequence.

In some embodiments, the crRNA is encoded by a nucleotide sequence selected from the group consisting of:

```
i)
5'-ATTTCTACtgttGTAGAT(SEQ ID NO: 25)-N_x-3';

ii)
5'-ATTTCTACtattGTAGAT(SEQ ID NO: 26)-N_x-3';

iii)
5'-ATTTCTACtactGTAGAT(SEQ ID NO: 27)-N_x-3';

iv)
5'-ATTTCTACtttgGTAGAT(SEQ ID NO: 28)-N_x-3';

v)
5'-ATTTCTACtagttGTAGAT(SEQ ID NO: 29)-N_x-3';

vi)
5'-ATTTCTACTATGGTAGAT(SEQ ID NO: 30)-N_x-3';

vii)
5'-ATTTCTACTGTCGTAGAT(SEQ ID NO: 31)-N_x-3';

viii)
5'-ATTTCTACTTGTGTAGAT(SEQ ID NO: 32)-N_x-3';
and
```

```
-continued
ix)
5'-ATTTCTACTGTGGTAGAT(SEQ ID NO: 33)-N_x-3',
``` wherein Nx represents nucleotide sequence that consists of x consecutive nucleotides, N is independently selected from A, G, C and T; x is an integer of 18≤x≤35, preferably, x=23. In some embodiments, the sequence Nx (spacer sequence) is capable of specifically hybridizing to the complement of the target sequence.

In some embodiments, the crRNAs of the invention are particularly suitable for use in combination with the Cpf1 protein of the invention for genome editing, particularly for genome editing in eukaryotes such as mammals.

3. Method for Modifying a Target Sequence in the Genome of a Cell

In another aspect, the present invention provides a method of modifying a target sequence in the genome of a cell, comprising introducing the genome editing system of the present invention into the cell, whereby the guide RNA targets the Cpf1 protein to a target sequence in the genome of the cell, resulting in one or more nucleotide substitution, deletion and/or addition in the target sequence.

In another aspect, the present invention provides a method of producing a genetically modified cell, comprising introducing the genome editing system of the present invention into the cell, whereby the guide RNA targets the Cpf1 protein to a target sequence in the genome of the cell, resulting in one or more nucleotide substitution, deletion and/or addition in the target sequence.

In another aspect, the invention also provides a genetically modified organism comprising a genetically modified cell produced by the method of the invention or a progeny cell thereof.

The design of target sequences or crRNA coding sequences that can be recognized and targeted by the Cpf1 protein and guide RNA (i.e., crRNA) complex can be found, for example, in Zhang et al., Cell 163, 1-13, October 22, 2015. In general, the 5'-terminus of the target sequence targeted by the genome editing system of the present invention needs to include a protospacer adjacent motif (PAM) 5'-TTTN, 5'-TTN, 5'-CCN, 5'-TCCN, 5'-TCN or 5'-CTN, wherein N is independently selected from A, G, C and T.

For example, in some embodiments of the present invention, the target sequence has the following structure: 5'-TYYN-Nx-3' or 5'-YYN-Nx-3', wherein N is independently selected from A, G, C and T, Y is selected from C and T; x is an integer of 15≤x≤35; Nx represents x consecutive nucleotides.

In some embodiments, the coding sequence of the crRNA comprises a crRNA scaffold sequence set forth in any one of SEQ ID NOs: 25-33. In some preferred embodiments, the crRNA scaffold sequence is SEQ ID NO:30. In some embodiments, the coding sequence of the cRNA further comprises a sequence that specifically hybridizes to the complement of the target sequence (i.e., a spacer sequence) at 3' of the cRNA scaffold sequence.

In some embodiments, the crRNA is encoded by a nucleotide sequence selected from the group consisting of:

```
i)
5'-ATTTCTACtgttGTAGAT(SEQ ID NO: 25)-N_x-3';
``` ii)
5'-ATTTCTACtattGTAGAT(SEQ ID NO: 26)-N$_x$-3';

iii)
5'-ATTTCTACtactGTAGAT(SEQ ID NO: 27)-N$_x$-3';

iv)
5'-ATTTCTACtttgGTAGAT(SEQ ID NO: 28)-N$_x$-3';

v)
5'-ATTTCTACtagttGTAGAT(SEQ ID NO: 29)-N$_x$-3';

vi)
5'-ATTTCTACTATGGTAGAT(SEQ ID NO: 30)-N$_x$-3';

vii)
5'-ATTTCTACTGTCGTAGAT(SEQ ID NO: 31)-N$_x$-3';

viii)
5'-ATTTCTACTTGTGTAGAT(SEQ ID NO: 32)-N$_x$-3';
and ix)
5'-ATTTCTACTGTGGTAGAT(SEQ ID NO: 33)-N$_x$-3', wherein Nx represents nucleotide sequence that consists of x consecutive nucleotides, N is independently selected from A, G, C and T; x is an integer of 18≤x≤35, preferably, x=23. In some embodiments, the sequence Nx (spacer sequence) is capable of specifically hybridizing to the complement of the target sequence.

In the present invention, the target sequence to be modified may be located at any location in the genome, for example, in a functional gene such as a protein-encoding gene, or may be, for example, located in a gene expression regulatory region such as a promoter region or an enhancer region, thereby modification of gene functional or modification of gene expression can be achieved.

The substitution, deletion and/or addition in the target sequence of the cell can be detected by T7EI, PCR/RE or sequencing methods.

In the method of the present invention, the genome editing system can be introduced into the cell by a variety of methods well known to those skilled in the art.

Methods that can be used to introduce the genome editing system of the present invention into a cell include, but are not limited to, calcium phosphate transfection, protoplast fusion, electroporation, lipofection, microinjection, viral infection (e.g., baculovirus, vaccinia virus, adenovirus, adeno-associated virus, lentivirus and other viruses), gene gun method, PEG-mediated protoplast transformation, *Agrobacterium*-mediated transformation.

A cell edited by the method of the present invention can be a cell of mammals such as human, mouse, rat, monkey, dog, pig, sheep, cattle, cat; a cell of poultry such as chicken, duck, goose; a cell of plants including monocots and dicots, such as rice, corn, wheat, sorghum, barley, soybean, peanut and *Arabidopsis thaliana* and so on.

In some embodiments, the method of the invention are performed in vitro. For example, the cell is an isolated cell. In some embodiments, the cell is a CAR-T cell. In some embodiments, the cell is an induced embryonic stem cell.

In other embodiments, the method of the invention may also be performed in vivo. For example, the cell is a cell within an organism, and the system of the present invention can be introduced into the cell in vivo by, for example, a virus-mediated method. For example, the cell can be a tumor cell in a patient.

4. Therapeutic Applications

The invention also encompasses the use of the genome editing system of the invention in the treatment of diseases.

By modifying a disease-related gene by the genome editing system of the present invention, it is possible to achieve up-regulation, down-regulation, inactivation, activation, or mutation correction of the disease-related gene, thereby achieving disease prevention and/or treatment. For example, in the present invention, the target sequence may be located in a protein coding region of the disease-related gene, or may be, for example, located in a gene expression regulatory region such as a promoter region or an enhancer region, thereby enabling functional modification of the disease-related gene or expression modification of the disease-related gene.

A "disease-related" gene refers to any gene that produces a transcriptional or translational product at an abnormal level or in an abnormal form in a cell derived from a disease-affected tissue as compared to a non-disease control tissue or cell. When altered expression is related with the appearance and/or progression of a disease, it may be a gene that is expressed at an abnormally high level; or it may be a gene that is expressed at an abnormally low level. A disease-related gene also refers to a gene having one or more mutations or a genetic variation that is directly responsible for the disease or is genetic linkage with one or more genes responsible for the etiology of the disease. The transcribed or translated product may be known or unknown, and may be at normal or abnormal levels.

Accordingly, the invention also provides a method of treating a disease in a subject in need thereof, comprising delivering to the subject an effective amount of the genome editing system of the invention to modify a gene related with the disease.

The invention also provides the use of the genome editing system of the invention for the preparation of a pharmaceutical composition for treating a disease in a subject in need thereof, wherein the genome editing system is for modifying a gene related with the disease.

The invention also provides a pharmaceutical composition for treating a disease in a subject in need thereof, comprising the genome editing system of the invention and a pharmaceutically acceptable carrier, wherein the genome editing system is for modifying a gene related with the disease.

In some embodiments, the subject is a mammal, such as a human.

Examples of such diseases include, but are not limited to, tumors, inflammation, Parkinson's disease, cardiovascular disease, Alzheimer's disease, autism, drug addiction, age-related macular degeneration, schizophrenia, hereditary diseases, and the like.

Further examples of diseases and corresponding disease-related genes according to the invention can be found, for example, from Chinese patent application CN201480045703.4.

5. Kit

The scope of the invention also includes a kit for use in the method of the invention, comprising the genome editing system of the invention, and an instruction. The kit generally includes a label indicating the intended use and/or method for use of the contents of the kit. The term label includes any written or recorded material provided on or with the kit or otherwise provided with the kit.

Example

Material and Method
Cell Culture and Transfection

HEK293T, HeLa cells were cultured in DMEM medium (Gibco) supplemented with 10% FBS (Gibco) and 100 U/ml penicillin and 100 ug/ml streptomycin, and mouse EpiSC cells were cultured in N2B27 medium supplemented with bFGF. 12 h before transfection, the cells were seeded in a 12-well plate at the density of 500,000 per well. After 12 h, the density of the cells was about 60%-70%, and then 1.5 ug (Cpf1: crRNA=2:1) plasmid was transfected into the cells using Lipofectamine LTX and PLUS reagents (Invitrogen), and the medium was replaced with serum-free opti-MEM medium (Gibco) before transfection. After transfection, it was replaced with serum-added DMED medium at 8-12 h after transfection. 48 h after transfection, GFP positive cells were sorted by FACS for genotyping.

Genotype Analysis: T7EI Analysis and DNA Sequencing

GFP-positive cells were sorted by FACS, lysed with Buffer L+1/100V Protease K (Biotool) at 55° C. for 30 min, inactivated at 95° C. for 5 min, and directly used for PCR detection. Appropriate primers were designed near the Cpf1 targeting site, and the amplified product was purified using DNA Clean & Concentrator™-5 kit (ZYMO Research). 200 ng of purified PCR product was added into 1 uL of NEBuffer2 (NEB) and diluted to 10 uL with ddH$_2$O. Then, heterodimers were formed by re-annealing according to the previously reported method (Li, W., et al., Simultaneous generation and germline transmission of multiple gene mutations in rat using CRISPR-Cas systems. Nat Biotechnol, 2013. 31(8): p. 684-6). The reannealed product was added with 0.3 uL of T7EI endnucelease and 1/10 V NEBuffer2 (NEB), and digested at 37° C. for 1 h 30 min. Genotype analysis was performed by 3% TAE-Gel electrophoresis. Indels were calculated according to the method reported in the previous article (Cong, L., et al., Multiplex genome engineering using CRISPR/Cas systems. Science, 2013. 339(6121): p. 819-23).

The PCR product corresponding to the T7EI positive sample was ligated to the pEASY-T1 or pEASY-B (Transgen) vector, then transformed, plated, and incubated at 37° C. overnight. An appropriate amount of single colonies were picked for Sanger sequencing. Genotypes of mutants were determined by alignment with genotype of the wild-type.

Immunofluorescence Staining

The Cpf1 eukaryotic expression vector was transfected into HeLa cells for 48 hours and then fixed with 4% PFA for 10 min at room temperature; washed three times with PBST (PBS+0.3% Triton X100), blocked with 2% BSA (+0.3% Triton X100) for 15 min at room temperature, incubated with primary antibody Rat anti-HA (Roche, 1:1000) overnight, washed three times with PBST, and incubated with Cy3-labeled fluorescent secondary antibody (Jackson ImmunoResearch, 1:1000) for 2 h at room temperature. Nucleus were stained with DAPI (Sigma, 1:1000) for 10 min, and washed three times with PBST. The slides were mounted with Aqueous Mounting Medium (Abcam) and fixed. Zeiss LSM780 was used for observation.

Prokaryotic Expression and Purification of Cpf1 Protein

The Cpf1 encoding gene was cloned into the prokaryotic expression vector BPK2103/2104. The 10×His tag fused on C-terminal was used to purify the protein. The expression vector was transformed into BL21 (DE3) *E. coli* competent cells (Transgen). Clones in which IPTG induced high expression were selected and inoculated into 300 mL of CmR+LB medium, cultured at 37° C. with shaking to OD600~0.4. IPTG was added at a final concentration of 1 mM to induce expression at 16° C. for 16 h. The culture was centrifuged at 8000 rpm at 4° C. for 10 min, and the bacterial pellet was collected. The bacteria were lysed in 40 mL NPI-10 (+1×EDTA-free Protease Inhibitor Cocktail, Roche; +5% glycerol) on ice bath with ultrasonication crushing: total time 15 min, ultrasonication 2 s, pause 5 s, at the power of 100 W. After crushing, centrifugation was performed at 8000 rpm at 4° C. for 10 min, and the supernatant was collected. 2 mL of His60 Ni Superflow Resin (Takara) was added to the supernatant, shaked at 4° C. for 1 h, purified by Polypropylene Colums (Qiagen). Using gravity flow, the undesired proteins without the fused His10 tag was thoroughly washed away with 20 mL of NPI-20, 20 mL of NPI-40 and 10 mL of NPI-100, respectively. Finally, the Cpf1 protein with fused His10 tag was eluted from the Ni column with 6×0.5 mL NPI-500. The eluted protein of interest was dialyzed overnight against a dialysate (50 mM Tris-HCl, 300 mM KCl, 1 mM DTT, 20% Glycerol). The protein solution after dialysis was concentrated with 100 kDa Amicon Ultra-4, PLHK Ultracel-PL ultrafiltration tube (Millipore). Protein concentration was determined using a Micro BCA™ Protein Assay Kit (Thermo Scientific™).

RNA In Vitro Transcription

An in vitro transcriptional crRNA template with a T7 promoter was synthesized (BGI) and the crRNA was transcribed in vitro using the HiScribe™ T7 Quick High Yield RNA Synthesis Kit (NEB) according to the protocol. After the transcription was completed, crRNA was purified by Oligo Clean & Concentrator™ (ZYMO Research), and measured with NanoDrop (Thermo Scientific™) for the concentration, and stored at −80° C.

In Vitro Digestion Analysis

The target sequences with different 5'PAM sequences were synthesized and cloned into pUC19 or p11-LacY-wtx1 vector, amplified with primers and purified. 200 ng of purified PCR product was reacted with 400 ng of crRNA and 50 nM of Cpf1 protein in NEBUffer3 (NEB) reaction system for 1 h at 37° C., respectively. It was then analyzed by electrophoresis on a 12% Urea-TBE-PAGE gel or 2.5% agarose gel.

Target Sequence

The target sequences used in the experiment are shown in Table 1 below:

TABLE 1

| Target | Sequence (5'-3') | SEQ ID NO: | 5'PAM (5'-3') |
| --- | --- | --- | --- |
| Human Dnmt1 Target site 1 | CCTCACTCCTGCTCGGTGAATTT | 229 | TTTC |
| Human Dnmt1 Target site 2 | AGGAGTGTTCAGTCTCCGTGAAC | 230 | TTTG |
| Human Dnmt1 Target site 3 | CTGATGGTCCATGTCTGTTACTC | 231 | TTTC |

TABLE 1-continued

| Target | Sequence (5'-3') | SEQ ID NO: | 5'PAM (5'-3') |
|---|---|---|---|
| Mouse MeCP2 Target site 1 | CCTGCCTCTGCTGGCTCTGCAGA | 232 | TTTG |
| Mouse MeCP2 Target site 2 | TGATGTTTCTGCTTTGCCTGCCT | 233 | TTTC |
| Mouse MeCP2 Target site 3 | GGGGAAGCCGAGGCTTCTGGCAC | 234 | TTTG |
| Mouse MeCP2 Target site 4 | GTGTCCAACCTTCAGGCAAGGTG | 235 | TTTC |
| Mouse MeCP2 Target site 5 | GCCTGCCTCTGCTGGCTCTGCAG | 236 | TTT |
| Mouse MeCP2 Target site 6 | CTGATGTTTCTGCTTTGCCTGCC | 237 | TTT |
| Mouse MeCP2 Target site 7 | GGGGGAAGCCGAGGCTTCTGGCA | 238 | TTT |
| Mouse MeCP2 Target site 8 | CGTGTCCAACCTTCAGGCAAGGT | 239 | TTT |
| Mouse Tet1 Target site 1 | TCGGGTCAGCATCACTGGCTCAG | 240 | TTTC |
| Mouse Tet1 Target site 2 | CTGGGAGCAGCCTGAGAACCCTG | 241 | TTTG |
| Mouse Tet1 Target site 3 | ACATCAGCTGAGCCAGTGATGCT | 242 | TTTG |
| Mouse Tet1 Target site 4 | GATTCTTGCAGTAGGTGCACTCC | 243 | TTTC |
| Mouse Tet1 Target site 5 | CTCTTCTTACAGATCTGGTGGCT | 244 | TTTC |
| Mouse Tet1 Target site 6 | CTCGGGTCAGCATCACTGGCTCA | 245 | TTT |
| Mouse Tet1 Target site 7 | CACAGGCCAGTACCTCTTCTCCC | 246 | TTA |
| Mouse Tet1 Target site 8 | CGATTCTTGCAGTAGGTGCACTC | 247 | TTT |
| Human AAVS1 Target site 1 | TGAGAATGGTGCGTCCTAGGTGT | 248 | TTTG |
| Human AAVS1 Target site 2 | GTGAGAATGGTGCGTCCTAGGTG | 249 | TTT |
| Human AAVS1 Target site 3 | ACCAGGTCGTGGCCGCCTCTACT | 250 | TTC |
| Human AAVS1 Target site 4 | TGTGGAAAACTCCCTTTGTGAGA | 251 | CCG |
| Human AAVS1 Target site 5 | CTACTCCCTTTCTCTTTCTCCAT | 252 | CCT |
| Human AAVS1 Target site 6 | TGTCCCCCTTCCTCGTCCACCAT | 253 | CCC |
| Human AAVS1 Target site 7 | CCTTTGTGAGAATGGTGCGTCCT | 254 | CTC |
| Human AAVS1 Target site 8 | CTACAGGGGTTCCTGGCTCTGCT | 255 | TCC |
| Mouse Apob Target site 12 | GTGGGCCCATGGCGGATGGATGG | 256 | TTTC |
| Mouse Nrl Target site 1 | CCTCCCAGTCCCTTGGCTATGGA | 257 | TTTC |
| Mouse Nrl Target site 7 | GGCTCCACACCATACAGCTCGGT | 258 | TTG |

Example 1. Identification of Novel Cpf1 Proteins

CRISPR/Cpf1 (Clustered Regularly Interspaced Short Palindromic Repeats from *Prevotella* and *Francisella* 1) is an acquired immune mechanism found in *Prevotella* and *Francisella* and successfully engineered for DNA editing (Zetsche, B., et al., Cpf1 is a single RNA-guided endonuclease of a class 2 CRISPR-Cas system. Cell, 2015. 163(3): p. 759-71). Unlike CRISPR/Cas9, Cpf1 requires only one crRNA as a guide, no tracrRNA is required, and the Cpf1 protein uses a T-rich PAM sequence.

The present inventors performed a PSI-Blast search in the NCBI database using the already reported AsCpf1, LbCpf1 and FnCpf1, and selected 25 unreported Cpf1 proteins, of which 21 CpfA proteins possess a direct repeat (DR) sequence.

By sequence alignment, the sequences and the RNA secondary structures of the 21 DR from different Cpf1 proteins were found to be quite conserved (FIG. 1). Based on the hypothesis that besides the conserved crRNA, the PAM sequences of all Cpf1 proteins were also conserved (i.e., all using T-rich PAM sequences), 12 of the 25 Cpf1 proteins were selected as candidates. The specific information of the selected 12 candidate Cpf3 proteins is shown in Table 2 below:

TABLE 2

Candidate Cpf1 Proteins

| Name | Bacteria Source | GenBank ID | Amino Acid Sequence (SEQ ID NO) | Codon optimization (human) nucleotide sequence (SEQ ID NO) |
|---|---|---|---|---|
| ArCpf1 | *Agathobacter rectalis* strain 2789STDY5834884 | CZAJ01000001.1 | 1 | 13 |
| LpCpf1 | *Lachnospira pectinoschiza* strain 2789STDY5834886 | CZAK01000004.1 | 2 | 14 |
| SaCpf1 | *Sneathia amnii* strain SN3 | CP011280.1 | 3 | 15 |
| HkCpf1 | *Helcococcus kunzii* ATCC 51366 | JH601088.1/ AGEI01000022.1 | 4 | 16 |
| AbCpf1 | *Arcobacter butzleri* L348 | JAIQ01000039.1 | 5 | 17 |
| BoCpf1 | *Bacteroidetes* oral taxon 274 | NZ_GG774890.1 | 6 | 18 |
| OsCpf1 | *Oribacterium* sp. NK2B42 | NZ_KE384190.1 | 7 | 19 |
| BsCpf1 | *Butyrivibrio* sp. NC30 | NZ_AUKC01000013.1 | 8 | 20 |
| PsCpf1 | *Proteocatella sphenisci* DSM 23131 | NZ_KE384028.1 | 9 | 21 |
| C6Cpf1 | *Candidatus Dojkabacteria* | LBTH01000007.1 | 10 | 22 |
| PxCpf1 | *Pseudobutyrivibrio xylanivorans* strain DSM 10317 | FMWK01000002.1 | 11 | 23 |
| PrCpf1 | *Pseudobutyrivibrio ruminis* | NZ_KE384121.1 | 12 | 24 |

Example 2. Verification of the Ability of the Cpf1 Proteins to Edit Human Genome Codon optimization was performed for expression in humans and 12 selected protein coding sequences were synthesized (BGI), cloned into eukaryotic expression vectors (pCAG-2AeGFP-SV40 and pCAG-2AeGFP-SV40_v4) and prokaryotic expression vectors (BPK2103-ccdB and BPK2014-ccdB).

Figure 2:
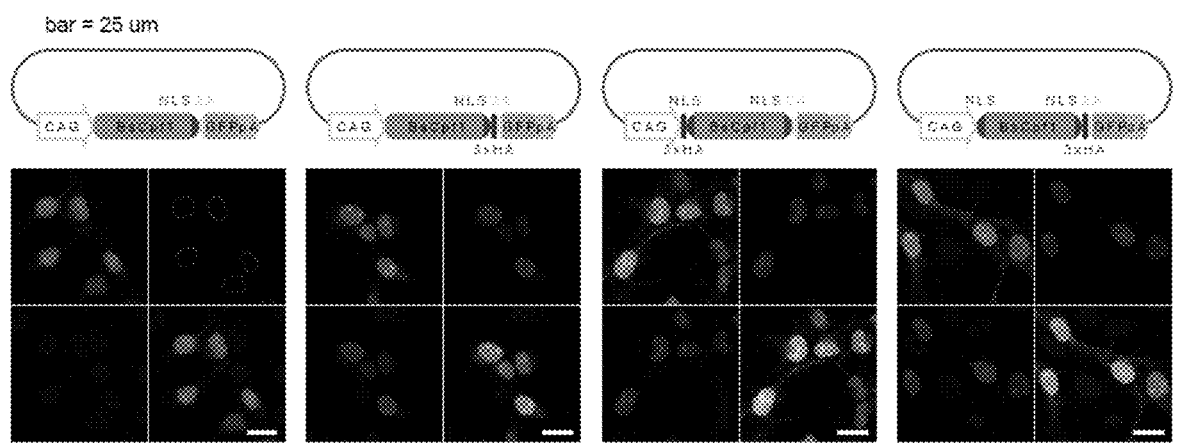
FIG. 2. Immunofluorescence showing that the Cpf1 proteins were localized in the nucleus.

Through HeLa cell transfection experiments, we can find that the selected Cpf1 proteins can be clearly expressed in the nucleus (FIG. 2).

Figure 3:
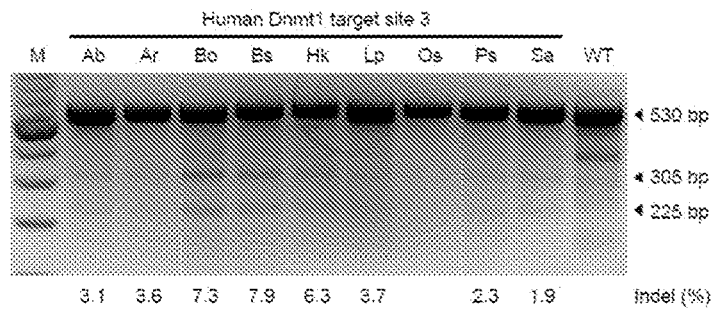
FIG. 3. shows the ability of the Cpf1 proteins to edit human Dnmt1 site 3. A: T7EI assay shows that 8 of the 9 selected Cpf1 proteins were able to achieve insertion/deletion (indel) at human Dnmt1 site 3 in 293T cells; B: sequencing results show representative indel in human Dnmt1 site 3.

Next, by co-transfection with crRNA targeting human Dnmt1 gene into 293T cells and identification by PCR and T7EI digestion, 8 Cpf1 proteins (Ab, Ar, Bo, Bs, Hk, Lp, Ps, Sa) were found to induce mutation at site 3 of the Dnmt1 gene in 293T cells (FIG. 3A). DNA sequencing further confirmed that the gene site did produce a genetic mutation (FIG. 3B).

Figure 4:
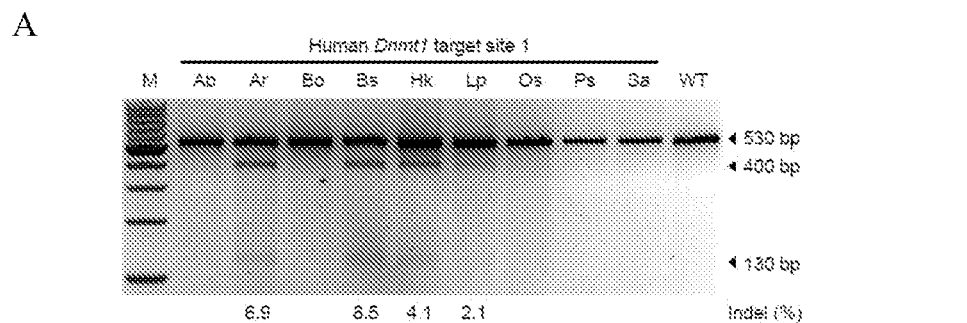
FIG. 4. shows the ability of the Cpf1 proteins to edit human Dnmt1 site 1. A: The T7EI assay shows that four Cpf1 proteins were clearly targeted to human Dnmt1 site 1. B: Sequencing results show representative indels in human Dnmt1 site 1, wherein 6 Cpf1 proteins were capable of producing indels, although PsCpf1 and SaCpf1 had no significant bands in the enzyme digestion assay.
Figure 5:
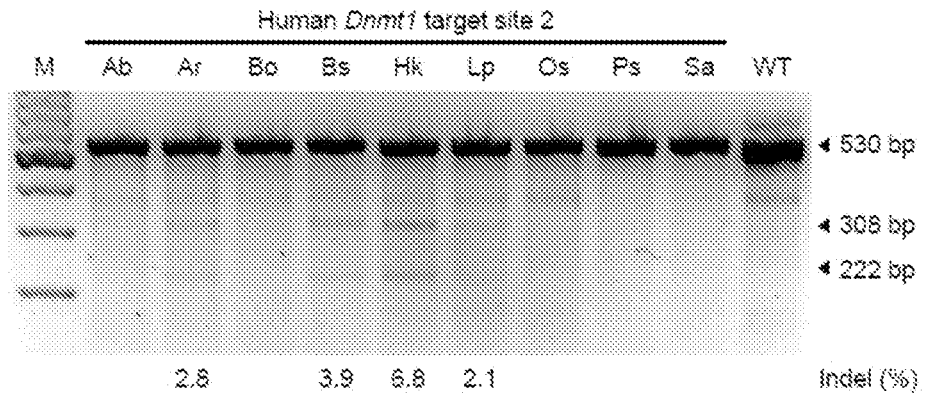
FIG. 5. shows the ability of the Cpf1 proteins to edit human Dnmt1 site 2. A: The T7EI assay shows that four Cpf1 proteins were clearly targeted to human Dnmt1 site 2. B: Sequencing results show representative indels in human Dnmt1 site 2, wherein 5 Cpf1 were capable of producing indels, although PsCpf1 had no significant bands in the enzyme digestion assay.

To further demonstrate that the identified Cpf1 proteins can induce mutations in the mammalian genome, the above experiments were repeated using sites 1 and 2 of the Dnmt1 gene. T7EI digestion results revealed that four proteins, ArCpf1, BsCpf1, HkCpf1 and LpCpf1, produced significant indels at both sites (FIGS. 4A and 5A). DNA sequencing results showed that besides the above four proteins, PsCpf1 and SaCpf1 also caused mutations in the gene (FIGS. 4B and 5B).

Example 3. Identification of PAM Sequences

To determine the PAM sequence of the identified Cpf1 proteins, first, the BsCpf1 protein was selected for detailed study.

BsCpf1 was expressed in *E. coli* and purified by His tag (FIG. 6A). The purified BsCpf1 protein and the corresponding crRNA and dsDNA fragment (human Dnmt1 target site 2) were incubated at 37° C. for 1 h, and then subjected to TBE denaturing PAGE gel electrophoresis, which proved that the PAM sequence of BsCpf1 was 5'(T)TTN- (FIG. 6B-E).

Figure 7:
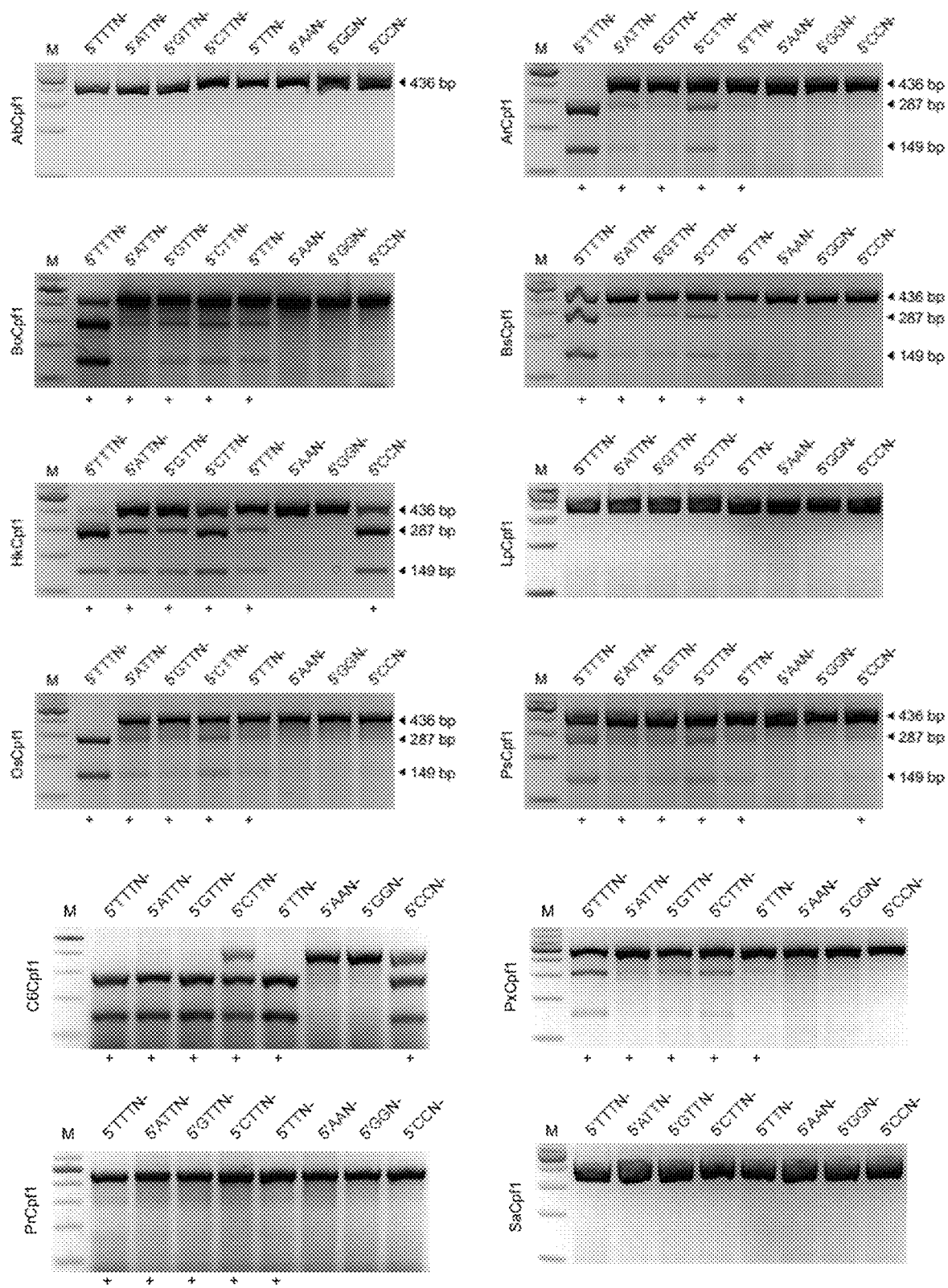
FIG. 7. In vitro assay of PAM sequences of each Cpf1. "+" indicates in vitro digestion activity.

Then, the PAM sequences of the remaining Cpf1 proteins were identified by a similar method, and the results are shown in FIG. 7. The experimental results show that the selected Cpf1 proteins all have in vitro enzymatic activity. The PAM sequence of 9 of the Cpf1 proteins is 5'(T)TTN-. The PAM sequences of C6Cpf1, HkCpf1 and PsCpf1 are 5'(T)YYN-.

Figure 8:
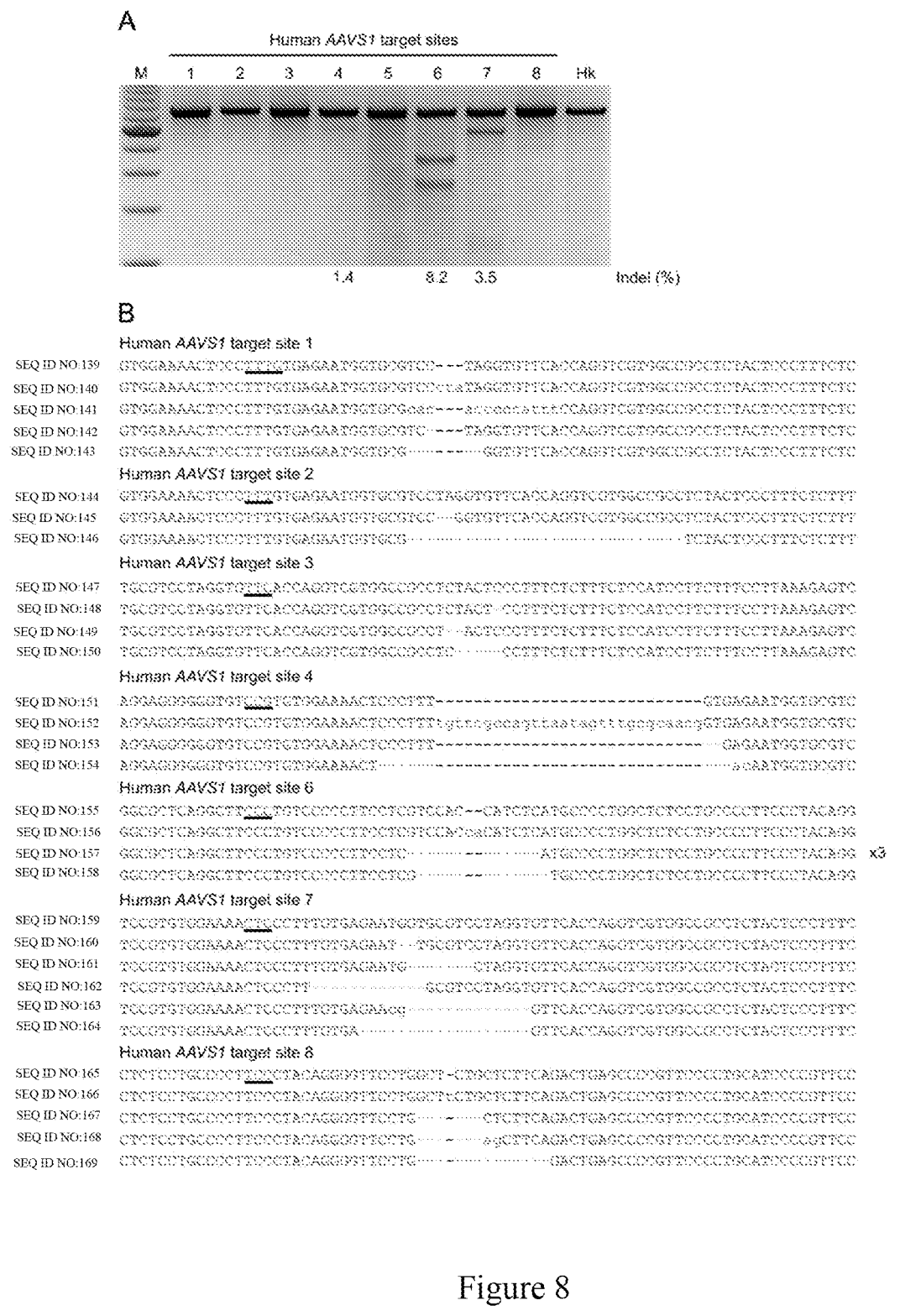

To confirm that the PAM sequence for in vivo editing of HkCpf1 is 5'(T)YYN-, the HkCpf1 vector was transfected into 293T cells with the targeted crRNA vector at 8 sites on the human AAVS1 gene, respectively. The experimental results show that (FIG. 8), HkCpf1 can edit 7 of the sites and generate mutations, and the PAM sequence is 5'(T)YYN- (underlined portion of FIG. 8B).

Example 4. Genome Editing in Mouse

To extend the applicability of these Cpf1 proteins, a number of transfection experiments were performed in mouse EpiSC cell lines.

Figure 9:
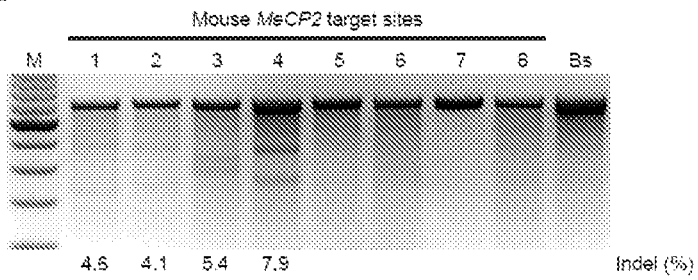

First, we transfected EpiSC cells with the BsCpf1 vector and the crRNA vectors (pUC19-crRNA) targeting eight sites on the mouse Tet1 gene, respectively. It was confirmed by T7EI digestion and DNA sequencing that BsCpf1 caused gene mutations at sites 2, 3 and 7 (FIG. 9A). The PAM sequence of site 7 was 5'TTA-, and the result was in agreement with the conclusion of Example 3. This indicates that the BsCpf1 protein uses the 5' TTN-PAM sequence.

Figure 11:
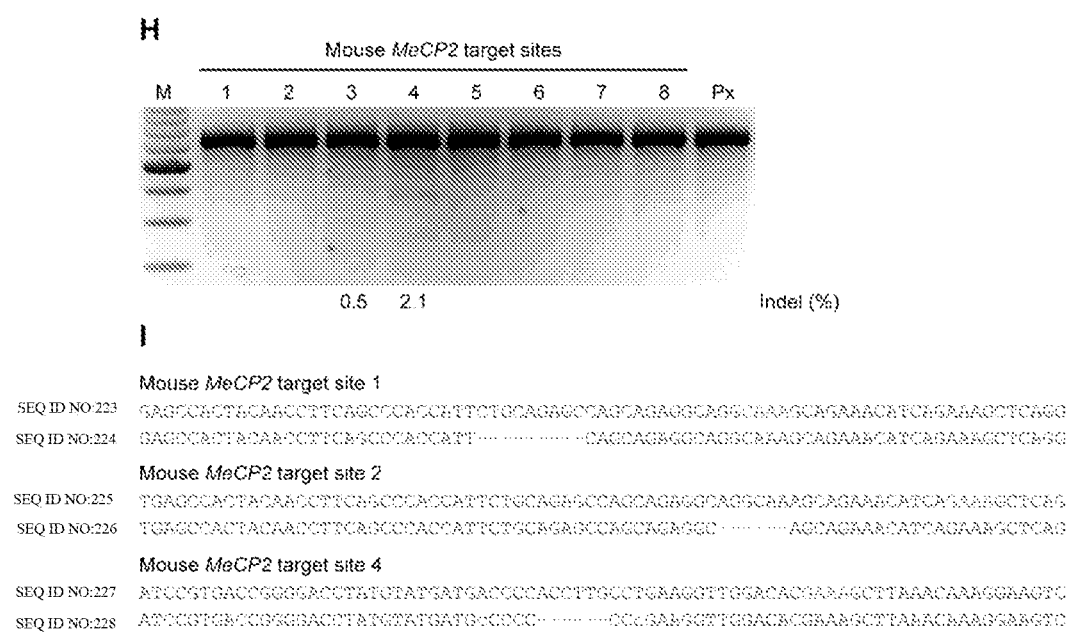

Next, the DNA editing ability of ArCpf1, BsCpf1, HkCpf1, and PxCpf1 was repeatedly verified. Co-transfection was carried out with the crRNA vectors (pUC19-crRNA) targeting eight sites on the mouse MeCP2 gene. Using T7EI digestion and DNA sequencing, it was demonstrated that ArCpf1 (FIG. 10 D, E), BsCpf1 (FIG. 9B, C), HkCpf1 (FIG. 10 F, G) and PxCpf1 (FIG. 11 H, I) can target and edit the genome of mouse.

Figure 12:
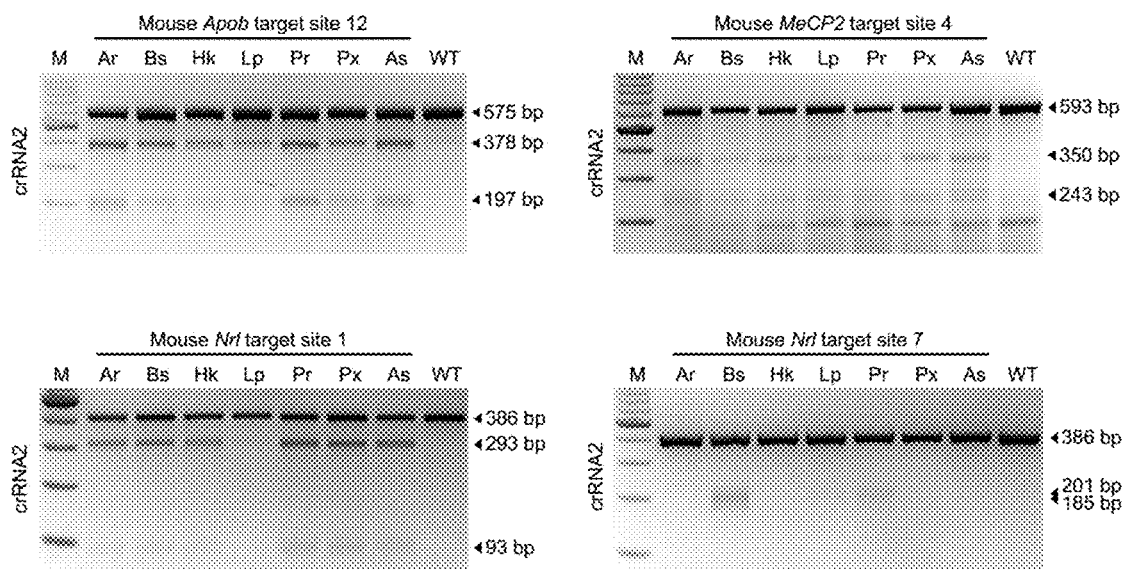
FIG. 12. Further validation of the editing ability of ArCpf1, BsCpf1, HkCpf1, LpCpf1, PrCpf1 and PxCpf1 for different targets in mice.

In addition, the editing ability of ArCpf1, BsCpf1, HkCpf1, LpCpf1, PrCpf1 and PxCpf1 was further verified by target site 12 of mouse Apob, target site 4 of mouse MeCP2, target site 1 of mouse Nrl and target site 7 of mouse Nrl. The results are shown in FIG. 12, and all six proteins can edit the genome. The PAM sequence of site Nrl-7 is 5'TTG, indicating that the PAM sequence of BsCpf1 and PrCpf1 is 5'TTN-.

The above experimental results demonstrate that the 12 Cpf1 proteins found in the present invention all have DNA editing ability, wherein ArCpf1 (SEQ ID NO: 1), BsCpf1 (SEQ ID NO: 8), HkCpf1 (SEQ ID NO: 4), PxCpf1 (SEQ ID NO: 11), LpCpf1 (SEQ ID NO: 2) and PrCpf1 (SEQ ID NO: 12) enable efficient mammalian genome editing.

Example 5. Optimizing the crRNA Scaffolds to Improve Editing Efficiency

This example optimizes the cRNA scaffolds of the newly identified Cpf1 proteins that can be used for mammalian genome editing so as to improve the genome editing efficiency of each Cpf1 protein (Table 3).

The experimental results are shown in FIG. 13. FIG. 13A shows that cells were transfected with each Cpf1 proteins and different crRNA plasmids, and by PCR and T7EI analysis, it demonstrated that different crRNA scaffolds affect the editing efficiency of Cpf1 proteins.

The inventors then established a library of crRNA mutants, transfected with BsCpf1 or PrCpf1, respectively. Through PCR and T7EI analysis, crRNA mutants that enable Cpf1 to efficiently edit mammalian genome were screened.

The editing efficiency of the crRNA31 mutant was significantly higher than that of the wild-type crRNA scaffold (crRNA2) derived from the genome of the strain. The cells were transfected with Cpf1, crRNA31, and crRNA2 plasmids, and it was confirmed by PCR and T7EI analysis that crRNA31 can increase the editing efficiency of five Cpf1 s of ArCpf1, BsCpf1, HkCpf1, PrCpf1, and PxCpf1 at the site MeCP2-4 by two folds (FIG. 13B).

Figure 14:
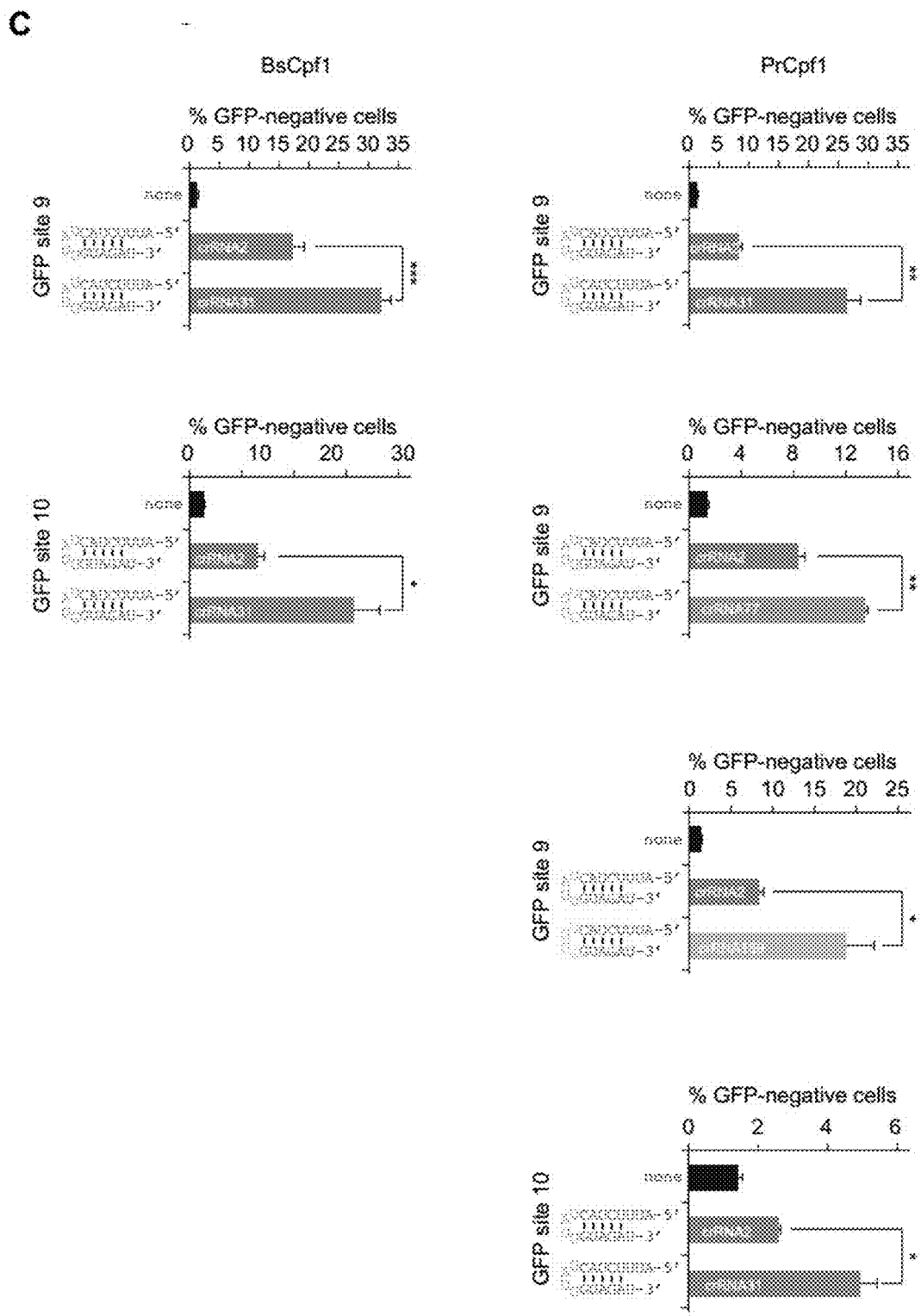
Figure 15:
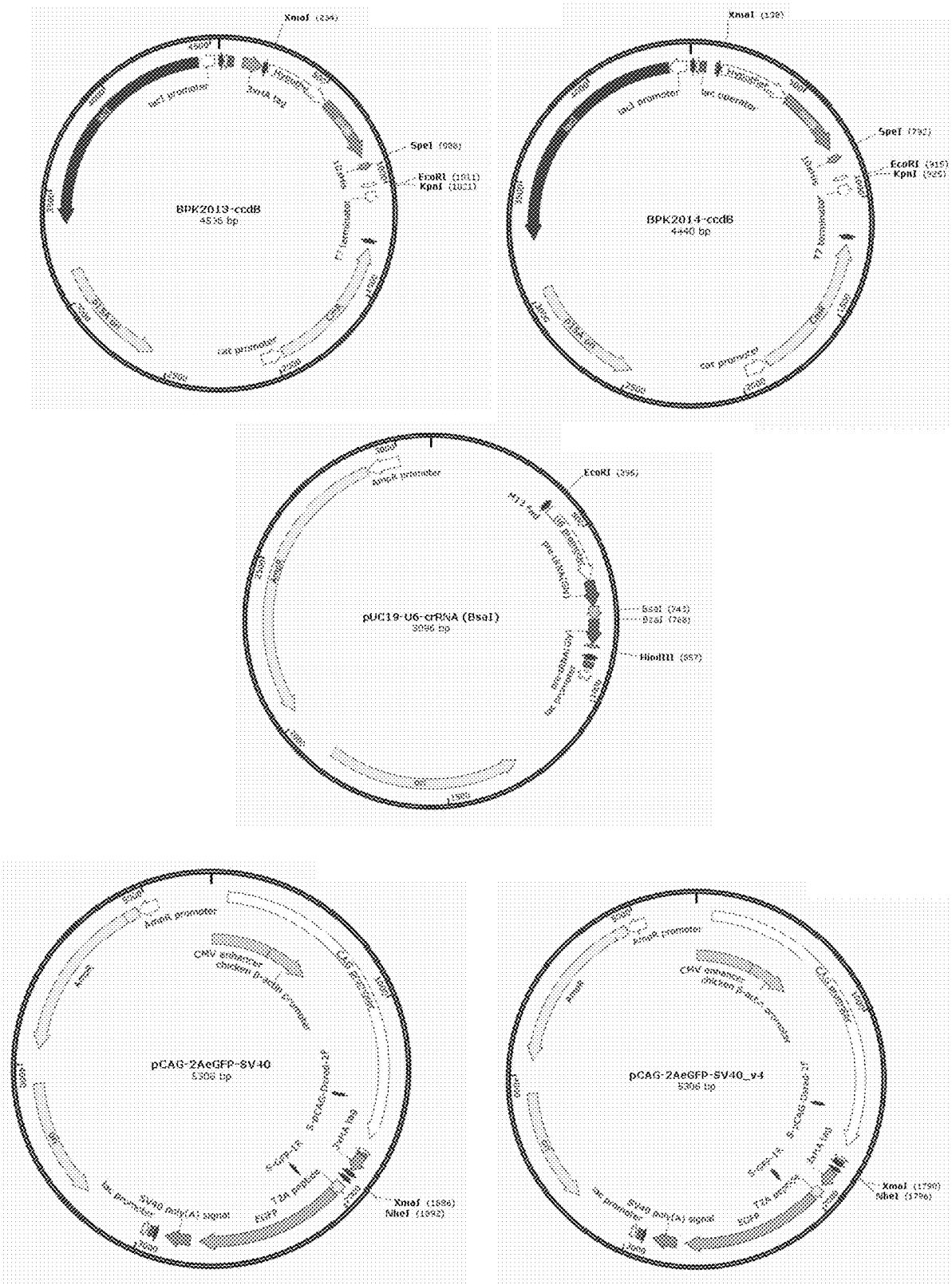
FIG. 15. shows the various vector maps as used.

FIGS. 14A and B show that analysis of different target sites by T7EI confirms that the screened cRNA scaffolds can improve the editing efficiency of BsCpf1 and PrCpf1. For PrCpf1, in addition to crRNA31 scaffold, crRNA77, crRNA129 and crRNA159 scaffolds can also significantly improve the editing efficiency at the site Nrl-1.

FIG. 14C shows analysis of intracellular GFP editing efficiency by flow cytometry. crRNA31 scaffold can improve the editing efficiency of BsCpf1 and PrCpf1, and crRNA77 and crRNA159 can also significantly improve the editing efficiency of PrCpf1.

TABLE 3

Identified cRNA Scaffold

| cRNA Scafflod | crRNA Scafflod Sequence (5'-3') | SEQ ID NO |
|---|---|---|
| crRNA1 | ATTTCTACtgttGTAGAT | 25 |
| crRNA2 | ATTTCTACtattGTAGAT | 26 |
| crRNA3 | ATTTCTACtactGTAGAT | 27 |
| crRNA4 | ATTTCTACtttgGTAGAT | 28 |
| crRNA5 | ATTTCTACtagttGTAGAT | 29 |
| crRNA31 | ATTTCTACTATGGTAGAT | 30 |
| crRNA77 | ATTTCTACTGTCGTAGAT | 31 |
| crRNA129 | ATTTCTACTTGTGTAGAT | 32 |
| crRNA159 | ATTTCTACTGTGGTAGAT | 33 |

The invention claimed is:

1. A genome editing system for site-directed modification of a target sequence in the genome of a cell, comprising at least one of the following i) to v):
   i) a Cpf1 protein, and a guide RNA;
   ii) an expression construct comprising a nucleotide sequence encoding a Cpf1 protein, and a guide RNA;
   iii) a Cpf1 protein, and an expression construct comprising a nucleotide sequence encoding a guide RNA;
   iv) an expression construct comprising a nucleotide sequence encoding a Cpf1 protein, and an expression construct comprising a nucleotide sequence encoding a guide RNA;
   v) an expression construct comprising a nucleotide sequence encoding a Cpf1 protein and a nucleotide sequence encoding a guide RNA;
   wherein the Cpf1 protein comprises an amino acid sequence of SEQ ID NOs: 1-12 or an amino acid sequence having at least 80% sequence identity to one of SEQ ID NOs: 1-12, the guide RNA capable of targeting the Cpf1 protein to a target sequence in the genome of the cell;
   wherein the guide RNA is a crRNA; and
   wherein the coding sequence of the crRNA comprises a crRNA scaffold sequence set forth in any one of SEQ ID NOs: 25-31 and 33.

2. The system of claim 1, wherein the Cpf1 protein comprises an amino acid sequences having at least 85%, at least 90%, at least 95%, at least 96%, at least 97%, at least 98%, at least 99%, or 100% sequence identity to any one of SEQ ID NOs: 1-12.

3. The system of claim 1, wherein the Cpf1 protein is derived from a species selected from: *Agathobacter rectalis*, *Lachnospira pectinoschiza*, *Sneathia amnii*, *Helcococcus kunzii*, *Arcobacter butzleri*, *Bacteroidetes oral*, *Oribacterium* sp., *Butyrivibrio* sp., *Proteocatella sphenisci*, *Candidatus Dojkabacteria*, *Pseudobutyrivibrio xylanivorans*, and *Pseudobutyrivibrio ruminis*.

4. The system of claim 1, wherein the Cpf1 protein comprises an amino acid sequence selected from SEQ ID NO: 1, SEQ ID NO: 2, SEQ ID NO: 4, SEQ ID NO: 8, SEQ ID NO: 11, and SEQ ID NO: 12.

5. The system of claim 1, wherein the nucleotide sequence encoding the Cpf1 protein is codon optimized for the organism from which the cell to be genome edited is derived.

6. The system of claim 1, wherein the nucleotide sequence encoding the Cpf1 protein is selected from any one of SEQ ID Nos: 13-24.

7. The system of claim 1, wherein the target sequence has the following structure: 5'-TYYN-Nx-3' or 5'-YYN-Nx-3', further wherein N is independently selected from A, G, C and T, Y is selected from C and T; x is an integer of 15≤x≤35; and Nx represents x consecutive nucleotides.

8. A method of modifying a target sequence in the genome of a cell, comprising introducing the genome editing system of claim 1 into the cell, whereby the guide RNA targets the Cpf1 protein to the target sequence in the genome of the cell, resulting in one or more nucleotide substitutions, deletions or additions in the target sequence.

9. The method of claim 8, wherein the cell is from a human, mouse, rat, monkey, dog, pig, sheep, cattle, cat; a poultry, or a monocot or dicot plant.

10. The method of claim 8, wherein the system is introduced into the cell by one or more of the following methods: calcium phosphate transfection, protoplast fusion, electroporation, lipofection, microinjection, viral infection, gene gun method, PEG-mediated protoplast transformation, or *Agrobacterium*-mediated transformation.

11. A method of treating a disease in a subject in need thereof, comprising delivering to the subject an effective amount of the genome editing system of claim 1 to modify a gene related with the disease in the subject.

12. The method of claim 11, wherein the subject is a human.

13. The method of claim 11, wherein the disease is selected from tumors, inflammation, Parkinson's disease, cardiovascular disease, Alzheimer's disease, autism, drug addiction, age-related macular degeneration, schizophrenia, and hereditary diseases.

14. A pharmaceutical composition for treating a disease in a subject in need thereof, comprising the genome editing system of claim 1 and a pharmaceutically acceptable carrier, wherein the genome editing system is for modifying a gene related with the disease.

15. The pharmaceutical composition of claim 14, wherein the subject is a human.

16. The pharmaceutical composition of claim 14, wherein the disease is selected from tumors, inflammation, Parkinson's disease, cardiovascular disease, Alzheimer's disease, autism, drug addiction, age-related macular degeneration, schizophrenia, and hereditary diseases.

17. A crRNA, wherein
   I.) said crRNA comprises a crRNA scaffold sequence corresponding to any one of SEQ ID NOs: 25-31 and 33, or
   II.) the coding sequence of said crRNA comprises a sequence set forth in any one of SEQ ID NOs: 25-31 and 33, or III.) said crRNA is encoded by a nucleotide sequence selected from:

i)
5'-ATTTCTACtgttGTAGAT(SEQ ID NO: 25)-N$_x$-3';

ii)
5'-ATTTCTACtattGTAGAT(SEQ ID NO: 26)-N$_x$-3';

iii)
5'-ATTTCTACtactGTAGAT(SEQ ID NO: 27)-N$_x$-3';

iv)
5'-ATTTCTACtttgGTAGAT(SEQ ID NO: 28)-N$_x$-3';

v)
5'-ATTTCTACtagttGTAGAT(SEQ ID NO: 29)-N$_x$-3';

vi)
5'-ATTTCTACTATGGTAGAT(SEQ ID NO: 30)-N$_x$-3';

vii)
5'-ATTTCTACTGTCGTAGAT(SEQ ID NO: 31)-N$_x$-3';
and viii)
5'-ATTTCTACTGTGGTAGAT(SEQ ID NO: 33)-N$_x$-3', wherein Nx represents nucleotide sequence that consists of x consecutive nucleotides, N is independently selected from A, G, C and T; and x is an integer of $18 \leq x \leq 35$.

18. The method of claim 8, wherein the cell is from a mammal.

19. The method of claim 8, wherein the cell is from a chicken, duck, or goose; or a plant selected from rice, corn, wheat, sorghum, barley, soybean, peanut and *Arabidopsis thaliana*.

* * * * *